(12) United States Patent
Glenn et al.

(10) Patent No.: US 7,655,419 B2
(45) Date of Patent: Feb. 2, 2010

(54) METHODS AND COMPOSITIONS FOR IDENTIFYING ANTI-HCV AGENTS

(75) Inventors: Jeffrey Glenn, Palo Alto, CA (US); Ella Sklan, Stanford, CA (US); Kirk A. Staschke, Indianapolis, IN (US); Tina Myers Oakes, Indianapolis, IN (US)

(73) Assignees: The Board of Trustees of the Leland Stanford Junior University, Palo Alto, CA (US); Eli Lily and Company, Indianapolis, IN (US)

( * ) Notice: Subject to any disclaimer, the term of this patent is extended or adjusted under 35 U.S.C. 154(b) by 0 days.

(21) Appl. No.: 11/844,993

(22) Filed: Aug. 24, 2007

(65) Prior Publication Data

US 2008/0261906 A1 Oct. 23, 2008

Related U.S. Application Data

(60) Provisional application No. 60/840,138, filed on Aug. 25, 2006.

(51) Int. Cl.
*G01N 33/53* (2006.01)
*A61K 39/29* (2006.01)

(52) U.S. Cl. ..................... 435/7.1; 424/228.1
(58) Field of Classification Search ........................ None
See application file for complete search history.

(56) References Cited

U.S. PATENT DOCUMENTS

| 2002/0147160 | A1 | 10/2002 | Bhat et al. |
| 2003/0087873 | A1 | 5/2003 | Stuyver et al. |
| 2004/0265792 | A1 | 12/2004 | Glenn et al. |
| 2006/0199174 | A1 | 9/2006 | Glenn et al. |

FOREIGN PATENT DOCUMENTS

| WO | WO9901582 A1 | 1/1999 |
| WO | WO02089731 A2 | 11/2002 |
| WO | 2006/073734 | 7/2006 |

OTHER PUBLICATIONS

Bartenschlager, R., et al. Replication of hepatitis C virus. Journal of General Virology. 2000, vol. 81, pp. 1631-1648.
Blight, K., et al. Efficient initiation of HCV RNA replication in cell culture. Science. 2000, vol. 290, pp. 1972-1974.
Egger, D., et al. Expression of hepatitis C virus proteins induces distinct membrane alternations including a candidate viral replication complex. Journal of Virology. 2002, vol. 76, No. 12, pp. 5974-5984.
Elazar, M., et al. Amphipathic helix-dependent localization of NS5I mediates hepatitis C virus RNA replication. Journal of Virology. 2003, vol. 77, No. 10, pp. 6055-6061.
Gorbalenya, A., et al. Viral proteins containing the purine NTP-binding sequence pattern. Nucleic Acids Research. 1989, vol. 17, No. 21, pp. 8413-8440.

HAAS, J., et al. Analysis of GTPase-activating proteins: Rab1 and Rab43 are key Rabs required to maintain a functional Golgi complex in human cells. Journal of Cell Science. 2007, vol. 120, pp. 2997-3010.
Hugle, T., et al. The hepatitis C virus nonstructural protein 4B is an integral endoplasmic reticulum membrane protein. Virology. 2001, vol. 284, pp. 70-81.
Lindenbach, B., et al. Unravelling hepatitis C virus replication from genome to function. Nature. 2005, vol. 436, pp. 933-938.
Machner, M., et al. Targeting of host Rab GTPase function by the intravacuolar pathogen Legionella pneumophila. Developmental Cell. 2006, vol. 11, pp. 47-56.
Mirzayan, C., et al. Genetic analysis of an NTP-binding motif in poliovirus polypeptide 2C. Virology. 1992, vol. 189, pp. 547-55.
Murata, T., et al. The Legionella pneumophila effector protein DrrA is a Rab1 guanine nucleotide-exchange factor. Nature Biology. 2006, vol. 8, No. 9, pp. 971-977.
Pawlotsky, J. Hepatitis C virus (HCV) NS5A protein: role in HCV replication and resistance to interferon-alpha. Journal of Viral Hepatitis. 1999, 6 Suppl 1:47-8.
Pawlotsky, J. Pathophysiology of hepatitis C virus infection and related liver disease. Trends in Microbiology. 2004, vol. 12, pp. 96-102.
Pfeffer, S., et al. Targeting Rab GTPases to distinct membrane compartments. Nature Reviews, Molecular Cell Biology. 2004, vol. 5, pp. 886-896.
Piccininni, S., et al. Modulation of the hepatitis C virus RNA-dependent RNA polymerase activity by the non-structural (NS) 3 helicase and NS4B membrane protein. Journal of Biological Chemistry. 2002, vol. 277, No. 47, pp. 45670-45679.
Reed, K. E., et al. Overview of hepatitis C virus genome structure, polyprotein processing, and protein properties. Current Topics in Microbiology and Immunology. 2000, vol. 242, pp. 55-84.
Rodriguez, P., et al. Poliovirus protein 2C has ATPase and GTPase activities. Journal of Biological Chemistry. 1993, vol. 268, No. 11, pp. 8105-8110.
Stone, M., et al. Participation of Rab5, an early endosome protein in hepatitis C virus RNA replication machinery. Journal of Virology. 2007, vol. 81, No. 9, pp. 4551-4563.
Vonderheit, A., et al. Rab7 associates with early endosomes to mediate sorting and transport of semliki forest virus to late endosomes. PLoS Biology. 2005, vol. 3, pp. 1225-1238.
Sklan, Ella H.; et al., "A Rab-GAP TBC Domain Protein Binds Hepatitis C Virus NS5A and Mediates Viral Replication", Journal of Virology, Oct. 2007, 81(20):11096-11105.
Sklan, Ella H.; et al., "TBC1D20 Is a Rab1 GTPase-activating Protein That Mediates Hepatitis C Virus Replication", The Journal of Biological Chemistry, Dec. 14, 2007, 282(50):36354-36361.

*Primary Examiner*—Stacy B Chen
(74) *Attorney, Agent, or Firm*—Carol L. Francis; Bozicevic, Field & Francis, LLP

(57) ABSTRACT

The invention features methods and compositions for screening for agents that modulate replication of a virus, particularly Flaviviridae virus (particularly hepatitis C virus (HCV)), where the methods provide for detection of agents that modulate the binding of TBC and NS5A, the inhibition of TBC activity, inhibition of Rab1 activity, and/or the expression of the TBC protein and/or Rab1 protein. The invention also features methods of controlling viral replication, and agents useful in such methods.

15 Claims, 15 Drawing Sheets

|  | NS5A | Δ4-27 | mAH | m1 1-236 | m2 1-100 | m3 237-447 | m4 237-302 | m5 303-447 |
|---|---|---|---|---|---|---|---|---|
| TBC1D20 | V | V | V | V | V | V | V |  |
| m1 1-363 |  | V |  |  |  | V | V |  |
| m2 1-269 |  | V |  |  |  | V | V |  |
| m3 1-200 |  | V |  |  |  | V | V |  |
| m4 200-403 | V | V | V | V |  | V | V |  |
| m5 269-403 | V | V | V | V | V | V | V |  |
| m6 63-269 |  | V |  |  |  | V | V |  |
| NS5A | V | V | V | V | V | V | V |  |

Glo siRNA3 siRNA1

CLTC

GIPSS LRGRA WQYLS GSKXX LEQNP GKFEE LXXXP GDPKW
LDVIE KDLHR QFPFH EMFVX RGGHG QQDLX RVLKA YTXYR
PEEGY CQAQA PIAAV LLMHM FAEQA FWCLV QICEK YLPGY
YSXGL EAIQL DGEIX FXLLR KVSPV AHKHL XRQXI DPVLY
MTEWF MCXFS RTLPW XSVLR VWDMF FCEGV KXIFR VALVL
L (SEQ ID NO:4)

B

GIPXS LRXXA WQXLS XXKXX XXQNP GKXXE XXXXX XDXXX
XXXIE XDLHR QFPFH EMFXX XGGXG QQDLX XXLXA YXXYX
XXXGY CQAQA PXAAV LLMHM FAEQA FWCXV XXCXX YLXGY
XSXXL EAIQX DGXXX XXLLX XXSXX AXXHL XXXXX XPXLY
MTEWF MCXFX RTLXW XXVLR XWDMF FCEGX KXIFR XXLVX
L (SEQ ID NO:5)

MALRSAQGDGPTSGHWDGGAEKADFNAKRKKKVAEIHQALNSDPT
DVAALRRMAISEGGLLTDEIRRKVWPKLLNVNANDPPPISGKNLR
QMSKDYQQVLLDVRRSLRRFPPGMPEEQREGLQEELIDIILLILE
RNPQLHYYQGYHDIVVTFLLVVGERLATSLVEKLSTHHLRDFMDP
TMDNTKHILNYLMPIIDQVNPELHDFMQSAEVGTIFALSWLITWF
GHVLSDFRHVVRLYDFFLACHPLMPIYFAAVIVLYREQEVLDCDC
DMASVHHLLSQIPQDLPYETLISRAGDLFVQFPPSELAREAAAQQ
QAERTAASTFKDFELASAQQRPDMVLRQRFRGLLRPEDRTKDVLT
KPRTNRFVKLAVMGLTVALGAAALAVVKSALEWAPKFQLQLFP
(SEQ ID NO:7)

FIG. 13

```
   1 ccgatgccga gcgggtgcta cgtcccgcgg tcggagccgc gtcttctccc ggctccgcca
  61 ccagccgggg ctcgggtggg ggcccggggc ccgggggcat ggccctccgg agtgcgcagg
 121 gcgacggccc cacctccggc cactgggacg gcggcgcgga gaaggcagac tttaacgcca
 181 aaaggaaaaa gaaagtggca gagatacacc aggctctgaa cagtgatccc actgatgtgg
 241 ctgcccttag acgcatggct atcagtgaag gagggctcct gactgatgag atcagacgaa
 301 aagtgtggcc caagctcctc aatgtcaatg ccaatgaccc acctcctata tcagggaaga
 361 acctacggca gatgagcaag gactaccaac aagtgttgct ggacgtccgg cggtcattgc
 421 ggcggttccc tcctggcatg ccagaggaac agagagaagg gctccaggaa gaactgattg
 481 acatcatcct cctcatcttg gagcgcaacc ctcagctgca ctactaccag ggctaccatg
 541 acattgtggt cacatttctg ctggtggtag gcgagaggct ggcaacatcc ctggtagaaa
 601 aattatctac ccaccacctc agggatttta tggatccaac aatggacaac accaagcata
 661 tattaaacta tctgatgccc atcattgacc aggtgaatcc agagctccat gacttcatgc
 721 agagtgctga ggtagggacc atctttgccc tcagctggct catcacctgg tttgggcatg
 781 tcctgtctga cttcaggcac gtcgtgcggt tatatgactt cttcctggcc tgccacccac
 841 tgatgccgat ttactttgca gccgtgattg tgttgtatcg cgagcaggaa gtcctggact
 901 gtgactgtga catggcctcg gtccaccacc tgttgtccca gatccctcag gacttgccct
 961 atgagacact gatcagcaga gcaggagacc tttttgttca gtttccccca tccgaacttg
1021 ctcgggaggc cgctgcccaa cagcaagctg agaggacggc agcctctact ttcaaagact
1081 ttgagctggc atcagcccag cagaggcctg atatggtgct gcggcagcgg tttcggggac
1141 ttctgcggcc tgaagatcga acaaaagatg tcctgaccaa gccaaggacc aaccgctttg
1201 tgaaattggc agtgatgggg ctgacagtgg cacttggagc ggctgcactg gctgtggtga
1261 aaagtgccct ggaatgggcc cctaagtttc agctgcagct gtttccctga aagccagaga
1321 agaccttcct cttacatcac attaaggcac ccactcacta ccttggcgtc gttttttggg
1381 tctgacttga ctcgtcaact gctggtctct cccacctggt tggaaatgtc gttggaaact
1441 tgcaaagact ctccagacct tagggaacaa gaggcatcac tcagtccttc tgggacagct
1501 tccctgcctc agaaaacgga atctctgtct gtgaccttct cctgcccat ttcacttgct
1561 caacaccaga ctttaatctg actgtagctc ataagaccct cattccagag agggtgctgc
1621 cccataccccg gaaggaggaa cgctgcacag agaggccaag aagcatctgg acagacaggc
1681 cttgctgggt ttagaccta tgcttttgt ccagtttcat ctcaacacag ctgccatgct
1741 tcagccatgc ctatccaatg acgtctccat aaaaggccca ggaacacggg agcttctgaa
1801 gagctgaaca tgtggaggga ggggaacgag aacttgtcca tgtgccaaga gggtggcgca
1861 cccccactcc atggggacag aagctccagc atttgcccag gacccgtcca gacctcaccc
1921 tgtgtgtatc ttcatctggc tgtttactta tttgtatcct tttctaataa tgtttgtaat
1981 aaactggtaa acataaaaaa aaaaaaaaaa aaaaaaaaa
```

(SEQ ID NO:3)

FIG. 16
A.
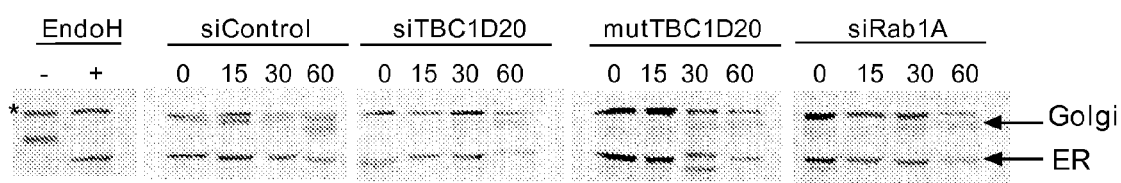
B.
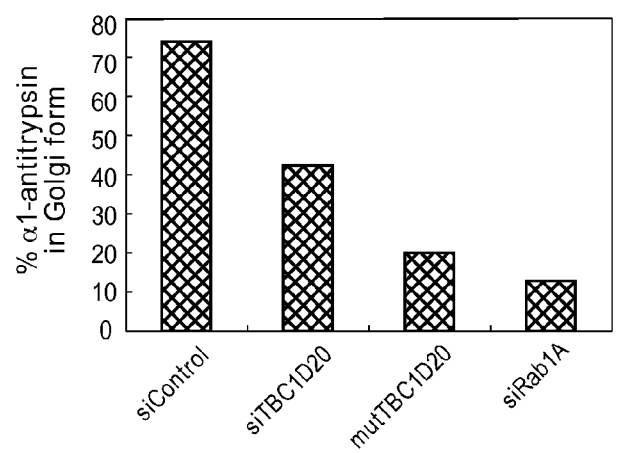

FIG. 17
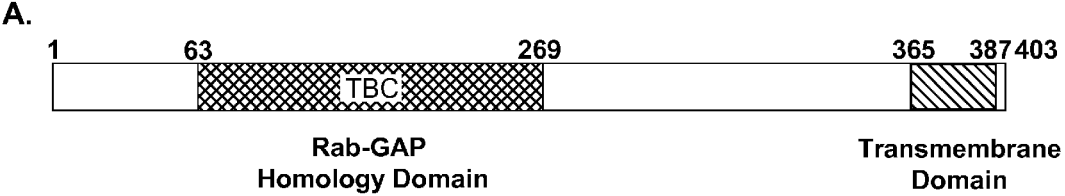
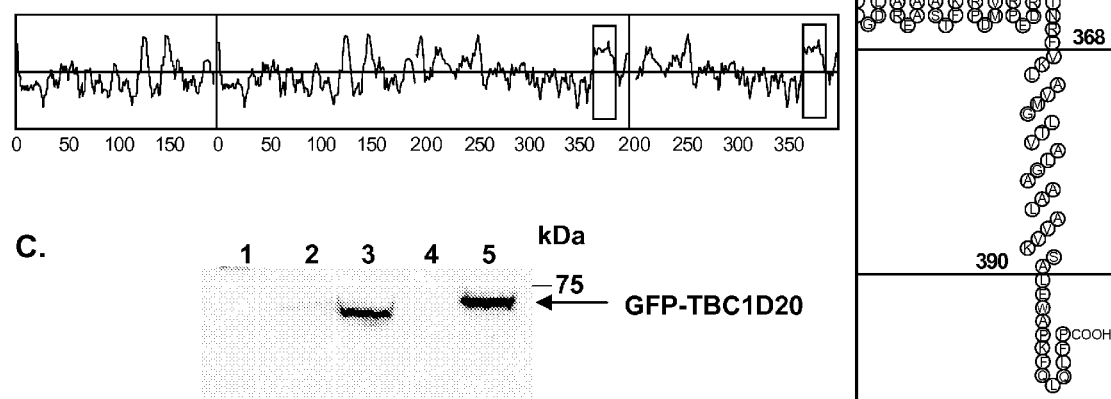
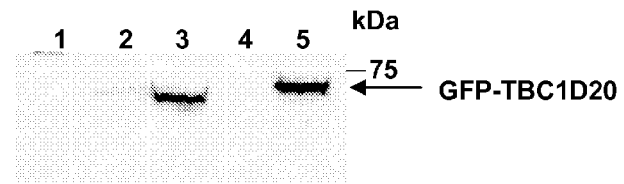

Effect of rab1 depletion on HCV replication

NS5A-mediated stimulation of TBC1D20 (rab1's GAP)

METHODS AND COMPOSITIONS FOR IDENTIFYING ANTI-HCV AGENTS

CROSS-REFERENCE TO RELATED APPLICATION

This application claims priority benefit of U.S. application Ser. No. 60/840,138, filed Aug. 25, 2006, which application is incorporated herein by reference in its entirety.

STATEMENT REGARDING FEDERALLY SPONSORED RESEARCH

This invention was made with Government support under Federal Grant No. RO1-DK064223 awarded by the National Institutes of Health. The Government has certain rights in this invention.

BACKGROUND

Hepatitis C virus (HCV), an example of a Flaviviridae virus, is the principal etiological agent of post-transfusion and community-acquired non-A non-B hepatitis worldwide. It is estimated that over 150 million people worldwide are infected by the virus. A high percentage of carriers become chronically infected with this pathogen and many patients progress to a state of chronic liver disease, so-called chronic hepatitis C. This group is in turn at high risk for serious liver disease such as liver cirrhosis, hepatocellular carcinoma and terminal liver disease leading to death.

HCV is an enveloped positive-strand RNA virus. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce structural and non-structural (NS) proteins, which are components of the mature virus and components involved in replication of the viral genome, respectively (Pawlotsky, 2004). In the case of HCV, the generation of mature nonstructural proteins (NS2, NS3, NS4A, NS4B, NS5A, and NS5B) is effected by two viral proteases. The first one is a metalloprotease located in NS2 that cleaves the NS2-NS3 junction in cis; the second one is a serine protease contained within the N-terminal region of NS3 (henceforth referred to as NS3 protease) and mediates all the subsequent cleavages downstream of NS3, both in cis, at the NS3-NS4A cleavage site, and in trans, at the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The non-structural protein 5A (NS5A) is part of the intracellular membrane-associated viral replication complex (Lindenbach et al., 2005). Mutations in NS5A affect the rate of HCV replication (Blight et al., 2000). NS5A has generated considerable interest because of a postulated role in determining the response to interferon (Pawlotsky, 1999).

Similar to other positive-strand RNA viruses, HCV replication occurs in intimate association with specific intracellular membrane structures, which for HCV has been termed the membranous web (Egger et al., 2002). What host machinery is exploited to establish these sites of viral replication is unknown.

Rab-GTPases are small GTP-binding proteins that regulate vesicular membrane trafficking pathways, behaving as membrane-associated molecular switches (Pfeffer et al., 2004). Rab proteins have been previously implicated in the life cycles of various enveloped viruses being utilized by these viruses for endocytosis, trafficking, and sorting of their proteins (see, e.g., Voderheit et al. 2005). Rab1 has previously been shown to be recruited to a replication complex of an intracellular pathogen (Machner et al. (2006) Developmental cell 11(1), 47; Murata et al. (2006) Nature cell biology 8(9), 971). There, a bacterial protein mimics a GTPase exchange factor that activates Rab1 and recruits it to an organelle that supports bacterial replication, thereby subverting membrane transport from the endoplasmic reticulum. We believe that a similar mechanism might apply for the NS5A-TBC1D20 interaction. Since in this case, the interaction is with a GAP which inactivates Rab 1, the mechanism might involve local inactivation of the Rab1, thereby preventing vesicle transport to the Golgi and promoting their redirection to viral replication sites.

The mechanism by which HCV establishes viral persistence and causes a high rate of chronic liver disease has not been elucidated. Antiviral interventions to date have focused upon, for example, ribavirin and interferon-alpha (IFN-α)-based monotherapy and combination therapy. However, many patients are either not responsive to these therapies, or suffer from relapse after an initial response.

Further methods for identifying anti-HCV agents are of interest in the field.

Literature of interest, including full citations for references above: Hugle et al, 2001, *Virol.* 284:70-81; Gorbalenya et al., 1989, *Nucleic Acids Res.* 17:8413-40; Bartenschlager et al., 2000, *Virol.* 81 Pt 7:1631-48; Reed et al., 2000, *Current Topics in Microbiol. and Immunol.* 242:55-84; Mirzayan et al, 1992, *Virol.* 189:547-55; Rodriguez et al., 1993, *J. Biol. Chem.* 268:8105-10; Piccininni, 2002, *J. Biol. Chem.* 277: 45670-9; Pawlotsky, 2004, *Trends in Microbiol.* 12:96-102; Lindenbach et al., 2005, *Nature* 436:933; Blight et al., 2000, *Science* 290:1972-4; Pawlotsky, 1999, *J. Viral Hepat.* 6 Supp 1:47-8; Egger et al., 2002, *J. Virol.* 76:5974-84; Pfeffer et al., 2004, *Nat. Rev. Mol. Cell Biol.* 5:886-96; Vonderheit et al., 2005, *PLoS Biol.* 3:e233; Elazar et al., 2003, *J. Virol.* 77:6055-61; Haas et al. (7 Aug. 2007) J. Cell Sci. 120, 2997-3010 (doi:10.1242/jcs.014225); Stone et al. (2007) *J. Virol.*, JVI.01366-01306; Machner et al. (2006) Developmental cell 11(1), 47; Murata et al. (2006) Nature cell biology 8(9), 971; US 2003/0087873; US2002/0147160, and WO 99/01582.

SUMMARY

The invention relates to methods and compositions for screening for agents that modulate replication of a virus, particularly Flaviviridae virus (particularly hepatitis C virus (HCV)), where the methods provide for detection of agents that modulate the binding of TBC and NS5A, the inhibition of TBC activity, the inhibition of Rab1 activity, and/or the expression of the TBC protein and/or Rab1 protein. The invention also features methods of controlling viral replication, and agents useful in such methods.

Accordingly, the disclosure provides methods of screening a test agent for activity in modulating the replication of a Flaviviridae virus comprising contacting a test agent with a NS5A polypeptide, a TBC1D20 polypeptide, and, optionally, a Rab1 polypeptide and/or an Arf1 polypeptide, said contacting being under a conditions suitable for TBC1D20 to activate a GTPase; and detecting the presence or absence of a change in an activity of at least one of the TBC1D20 polypeptide, the Rab1 polypeptide, and the Arf1 polypeptide; wherein the presence in a change in activity at least one of the TBC1D20 polypeptide, the Rab1 polypeptide, and the Arf1 polypeptide indicates the test agent has activity as an antiviral agent.

In related embodiments, the detecting step comprises detecting an effect of the test agent on binding between the TBC1D20 polypeptide and the NS5A polypeptide. In further related embodiments, the activity detected is Rab-GTPase activity of TBC1D20 and/or GTPase activity of a Rab1 polypeptide and/or a Arf1 polypeptide. In further related embodiments, the TBC1D20 polypeptide or NS5A polypeptide is attached to a detectable label, and said detecting step comprises detecting said detectable label. In embodiments of particular interest, the Flaviviridae virus is hepatitis C virus (HCV).

The disclosure also provides methods of screening a test agent for activity as an antiviral agent comprising contacting a test agent with a cell expressing NS5A and at least one of a TBC1D20 polypeptide, a Rab1 polypeptide, and an Arf1 polypeptide, said contacting being under conditions suitable for TBC1D20 to activate a GTPase; and detecting the presence or absence of a change in an activity of at least one of the TBC1D20 polypeptide, the Rab1 polypeptide, and the Arf1 polypeptide; wherein the presence in a change in activity at least one of the TBC1D20 polypeptide, the Rab1 polypeptide, and the Arf1 polypeptide indicates the test agent has activity as an antiviral agent.

In related embodiments, detecting comprises detecting an effect of the test agent on binding of TBC1D20 polypeptide to NS5A polypeptide. In further related embodiments, the detecting step comprises detecting an effect of the test agent on an activity of TBC1D20 polypeptide, e.g., activation of a GTPase (e.g., Rab1 or Arf1). In further related embodiments, detecting is by assessing expression of TBC1D20, Rab1, and/or Arf1.

In certain embodiments, the screening methods further comprises screening said agent for activity in reducing replication of a Flaviviridae virus in said cell-based assay.

The disclosure also provides methods of screening a test agent for activity as an antiviral agent comprising contacting a TBC1D20 polypeptide expression system and/or a Rab1 polypeptide expression system with a test agent, said contacting being under a condition suitable for expression of the TBC1D20 polypeptide and/or Rab1 polypeptide; and detecting the presence or absence of a change in expression of the TBC1D20 polypeptide and/or the Rab1 polypeptide; wherein the presence of a change in expression of the TBC1D20 polypeptide or the Rab1 polypeptide in the presence of the test agent relative to a level of expression of the TBC1D20 polypeptide or the Rab1 polypeptide in the absence of a test agent indicates the test agent has activity in modulating expression of TBC1D20 or Rab1 expression, which is indicative of antiviral activity against hepatitis C virus.

The disclosure also provides methods and compositions for identifying agents for treating infection by a virus that encodes a NS5A protein, or functional equivalent thereof, e.g., hepatitis C virus (HCV) or other members of the family Flaviviridae. In general, the methods involve contacting a NS5A protein, or functional equivalent thereof, and a TBC polypeptide with a test agent, and determining the effect of the test agent on binding between the NS5A protein, or functional equivalent thereof, and the TBC polypeptide, or contacting a test agent with a nucleic acid encoding TBC, and determining the effect of the test agent on expression of the TBC polypeptide. A test agent that inhibits NS5A polypeptide and TBC polypeptide binding to each other, or affects TBC-mediated activation of a host cell Rab-GTPase activity, or inhibits expression of the TBC polypeptide, is an anti-viral agent, e.g., an anti-HCV agent. The subject methods and compositions find use in a variety of therapeutic and screening applications.

The disclosure provides for a method of screening a test agent for activity in modulating the replication of a virus that encodes a NS5A polypeptide, or functional equivalent thereof, the method comprising contacting a TBC polypeptide and a NS5A polypeptide, or functional equivalent thereof, with a test agent, said contacting being under a condition suitable for binding between the TBC polypeptide and the NS5A polypeptide, or functional equivalent thereof; detecting the presence or absence of binding between the TBC polypeptide and the NS5A polypeptide, or functional equivalent thereof; wherein a decrease in binding between the TBC polypeptide and the NS5A polypeptide, or functional equivalent thereof, in the presence of the test agent relative to binding between the TBC1D20 polypeptide and the NS5A polypeptide, or functional equivalent thereof, in the absence of a test agent indicates the test agent has activity in modulating replication of the virus. The disclosure also features methods of modulating the replication of such a virus, and agents useful in such methods.

The disclosure provides for a method of screening a test agent for activity in modulating the replication of a Flaviviridae virus, the method comprising contacting a TBC1D20 polypeptide and a NS5A polypeptide with a test agent, said contacting being under a condition suitable for binding between the TBC1D20 polypeptide and the NS5A polypeptide, wherein said NS5A polypeptide is derived from a Flaviviridae virus; detecting the presence or absence of binding between the TBC1D20 polypeptide and the NS5A polypeptide; wherein a decrease in binding between the TBC1D20 polypeptide and the NS5A polypeptide in the presence of the test agent relative to binding between the TBC1D20 polypeptide and the NS5A polypeptide in the absence of a test agent indicates the test agent has activity in modulating replication of the Flaviviridae virus. The disclosure also features methods of modulating the replication of a Flaviviridae virus, and agents useful in such methods.

In some embodiments, the test agent reduces binding between the TBC1D20 polypeptide and the NS5A polypeptide. In some embodiments, the test agent binds to the TBC1D20 polypeptide. In some embodiments, the test agent binds to the NS5A polypeptide.

In some embodiments, the method comprises a detecting step comprises detecting an effect of the test agent on binding between the TBC1D20 polypeptide and the NS5A polypeptide in an in vitro assay. In some embodiments, the detecting step comprises detecting the formation of a TBC1D20 polypeptide-NS5A polypeptide complex. In some embodiments, the detecting step comprises detecting an effect of the test agent on binding between the TBC1D20 polypeptide or the NS5A polypeptide in a cell-based assay. In some embodiments, the effect is a biological activity caused by the formation of a TBC1D20 polypeptide-NS5A polypeptide complex. In some embodiments, the detecting step further comprises detecting the effect of the test agent in reducing replication of the Flaviviridae virus in said cell-based assay. In some embodiments, the TBC1D20 polypeptide or said NS5A polypeptide is attached to a detectable label, and said detecting step comprises detecting said detectable label.

The disclosure also provides for a method of screening a test agent for activity in modulating the expression of TBC1D20, the method comprising: contacting a TBC1D20 polypeptide expression system with a test agent, said contacting being under a condition suitable for expression of the TBC1D20 polypeptide; and detecting the presence or absence of a change in expression of the TBC1D20 polypeptide; wherein the presence of a change in expression of the TBC1D20 polypeptide in the presence of the test agent relative to a level of expression of the TBC1D20 polypeptide in the absence of a test agent indicates the test agent has activity in modulating TBC1D20 expression.

In some embodiments, the test agent reduces the expression of the TBC1D20 polypeptide. In some embodiments, the test agent reduces the translation of the TBC1D20 polypeptide. In some embodiments, the test agent binds to an mRNA encoding the TBC1D20 polypeptide or a Rab1-encoding nucleic acid. In some embodiments, the test agent is a small interfering nucleic acid (siNA). In some embodiments, the test agent is a siNA that is capable of sufficiently hybridizing with the mRNA encoding the TBC1D20 polypeptide or Rab1 polypeptide such that the translation is reduced.

The disclosure also provides for a method of screening a test agent for activity in modulating the enzymatic activity of a TBC polypeptide to activate a GTPase, the method comprising: contacting a TBC polypeptide with a test agent, said contacting being under a condition suitable for TBC to activate a GTPase; detecting the presence or absence of a change in the GTPase activity of the TBC polypeptide; wherein a decrease in the TBC polypeptide in the presence of the test agent relative to the TBC polypeptide in the absence of a test agent indicates the test agent has activity in modulating the enzymatic activity of a TBC polypeptide. In some embodiments, the test agent reduces enzymatic activity of a TBC polypeptide to activate the GTPase. In some embodiments, the test agent binds to the TBC polypeptide. In some embodiments, the detecting step comprises detecting an effect of the test agent on binding to the TBC polypeptide in an in vitro assay. In some embodiments, the detecting step comprises detecting an effect of the test agent on binding to the TBC polypeptide in a cell-based assay. In some embodiments, the effect is a biological activity caused by the activation of a GTPase. In some embodiments, the GTPase is Rab-GTPase. In some embodiments, the detecting step further comprises detecting the effect of the test agent in reducing replication of a Flaviviridae virus in said cell-based assay.

In some embodiments, the detecting comprises detecting an effect of the test agent on the expression of the TBC1D20 polypeptide in an in vitro assay. In some embodiments, the in vitro assay is a cell-free assay. In some embodiments, the in vitro assay comprises the use of cell extracts. In some embodiments, the detecting step comprises detecting the formation of an mRNA encoding said TBC1D20 polypeptide. In some embodiments, the detecting step comprises detecting the formation of a TBC1D20 polypeptide-NS5A polypeptide complex between said TBC1D20 polypeptide and a NS5A polypeptide, wherein said NS5A polypeptide is derived from a Flaviviridae virus. In some embodiments, the detecting step comprises detecting the formation the TBC1D20 polypeptide-NS5A polypeptide complex in a cell-based assay. In some embodiments, the detecting step comprises detecting a biological activity caused by the formation of the TBC1D20 polypeptide-NS5A polypeptide complex. In some embodiments, the biological activity is the replication of the Flaviviridae virus. In some embodiments, the TBC1D20 polypeptide is attached to a detectable label, and said detecting step comprises detecting said detectable label.

The disclosure also provides for a reaction mixture comprising: a TBC1D20 polypeptide; and a NS5A polypeptide; wherein either the TBC1D20 polypeptide or the NS5A polypeptide is recombinant or isolated.

In some embodiments, the TBC1D20 polypeptide or the NS5A polypeptide is detectably labeled. In some embodiments, the reaction mixture further comprises a test agent capable of reducing the binding between the TBC1D20 polypeptide and the NS5A polypeptide. In some embodiments, the test agent is an antibody, or a functional fragment thereof, capable of binding the TBC1D20 polypeptide or the NS5A polypeptide.

The disclosure also provides for a composition comprising: an isolated siNA, wherein the siNA comprises a sequence effective to reduce transcription or translation of a TBC1D20-encoding nucleic acid, and a pharmaceutically acceptable carrier. In some embodiments, the composition is a pharmaceutical composition.

The disclosure also provides for a method for inhibiting replication of a Flaviviridae virus in a subject in need of such treatment, comprising administering to the subject said composition, in an amount effective to inhibit Flaviviridae virus replication in the subject.

The disclosure also provides for a method for reducing viral load of a Flaviviridae virus in a subject in need of such treatment, the method comprising administering to the subject said composition, in an amount effective to reduce viral load in the subject.

Other aspects and features will be readily apparent to the ordinarily skilled artisan upon reading the present disclosure.

BRIEF DESCRIPTION OF THE DRAWINGS

The invention is best understood from the following detailed description of exemplary embodiments when read in conjunction with the accompanying drawings. It is emphasized that, according to common practice, the various features of the drawings are not necessarily to-scale. On the contrary, the dimensions of the various features are arbitrarily expanded or reduced for clarity. Included in the drawings are the following figures:

FIG. 11 depicts the amino acid sequences of SEQ ID NO:4-6, respectively of TBC1D20. "X" is any or no amino acid.

FIG. 12 depicts the amino acid sequence of TBC1D20 (SEQ ID NO:7).

FIG. 13 depicts the nucleotide sequence of the gene encoding TBC1D20 (SEQ ID NO:3).

FIG. 16 is a set of photos and a graph showing that TBC1D20 depletion blocks ER-to-Golgi transport of α1-antitrypsin. Panel A. Left panels. Untransfected cells were pulse labeled and the sensitivity of α1-antitrypsin to EndoH digestion was tested with no chase. The top band (asterisk) is a background band present in the precipitates. Huh7 cells were transfected with non-targeting siRNA control, TBC1D20 siRNA, or Rab1 siRNA, or a plasmid expressing a non-active mutant of TBC1D20 (R66A, R105A). Seventy two h after transfection, cells were labeled with [$^{35}$S]methionine for 15 min. After a chase in unlabeled methionine, cell lysates were prepared at different times. Immunoprecipitated α1-antitrypsin was digested with endo H overnight, and the resulting products were separated by SDS-10% PAGE and analyzed with a PhosphorImager. Arrows mark the Golgi and ER forms of α1-antitrypsin. Panel B. Quantitation of the appearance of a Golgi-modified α1-antitrypsin. Values represent the amount of Golgi form detected relative to the amount of the ER form for each condition, present at time zero.

FIG. 17 provides schematics and data showing TBC1D20 is a transmembrane protein. Panel A. Schematic diagram of TBC1D20. The predicted transmembrane domain is shown as hatched at the C-terminus (at the right); the TBC domain is indicated. Panel B. Left: Graphical output of the SOSUI analysis, with the 403 amino acid residues of TBC1D20 indicated along the x-axis. The plot describes the hydropathy profile of each segment. Panel B Right: a schematic diagram of the predicted transmembrane domain. Panel C. TBC1D20 membrane association is resistant to alkaline stripping. GFP-TBC1D20 membranes were then washed with 0.1M of sodium carbonate or buffer and pelleted by centrifugation. Equal amounts of cytosol (lane 1), released proteins and membranes, treated with buffer (lanes 2-3) or alkaline carbonate (lanes 4-5), respectively, were loaded and analyzed by SDS-PAGE and immunoblotting with anti-GFP antibodies.

DEFINITIONS

Figure 1:
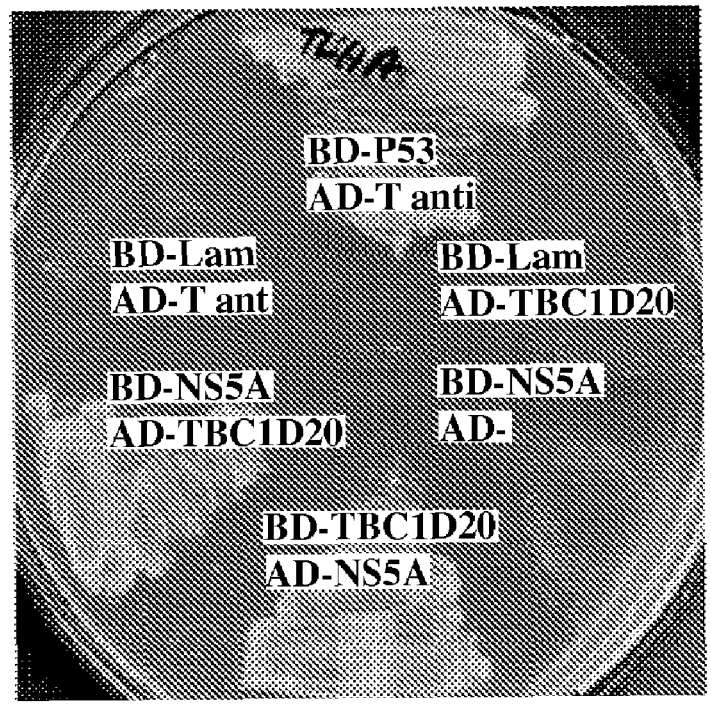
FIG. 1 depicts the growth or no growth of yeast in a GAL4-based yeast two-hybrid screen. "BD-P53, AD-T anti" is a positive control. "BD-Lam, AD-T anti" is a negative control. "BD-Lam, AD-TBC1D20" indicates that TBC1D20 alone does not self-activate. "BD-NS5A, AD-" indicates that NS5A alone does not self-activate. "BD-NS5A, AD-TBC1D20" and "BD-TBC1D20, AD-NS5A" indicates activation occurs when both NS5A and TBC1D20 are present.

By "TBC" or "TBC polypeptide" is meant a protein characterized by comprising a TBC/rabGAP consensus domain (Reczek et al., 2001, *J. Cell Biol.* 153(1):191-205); 2), or comprises the amino acid sequence of a TBC or TBC polypeptide comprises the amino acid sequence of SEQ ID NO:4, SEQ ID NO:5 or SEQ ID NO:6 (FIG. 11). Altenatively, a TBC or TBC polypeptide comprises one or more of the following amino acid sequences, DLHRQFPFHEMF (SEQ ID NO:12), GYCQAQAPXAAVLLMHMFAEQA FWC (SEQ ID NO:8), LYMTEWFMC (SEQ ID NO:9) and WDM-FFCEG (SEQ ID NO:10); wherein the TBC or TBC polypeptide is capable of activating Rab-GTPase. TBC are discussed in the following literature, e.g., Itoh et al., "Identification of EP164 as a GTPase-activating protein specific for Rab27A," 2006, *J. Biol. Chem. Aug.* 21; Itoh et al., 2006, *Genes Cells* 11(9):1023-37; Pan et al., 2006, *Nature* 442(7100):303-6; and Reczek et al., 2001, which are incorporated by reference herein in their entirety. In embodiments of particular interest, the TBC polypeptide is a mammalian TBC polypeptide, with human TBC polypeptide being of particular interest. An example of a TBC protein of particular interest is a TBC1D20 or TBC1D20 polypeptide. A "functional equivalent" of TBC or TBC polypeptide is a polypeptide that is capable of binding to NS5A or NS5A polypeptide (in particular NS5A of a Flaviviridae virus of HCV), or a functional equivalent thereof. The "functional equivalent" of TBC or TBC polypeptide may comprise one or more sequences selected form the group consisting of SEQ ID NO:4-10.

By "TBC1D20" or "TBC1D20 polypeptide" is meant a TBC1D20 protein. In embodiments of particular interest, the TBC1D20 polypeptide is a mammalian TBC1D20 polypeptide, with human TBC1D20 polypeptide being of particular interest. TBC1D20 is a TBC of particular interest. Where TBC1D20 is mentioned within this specification, the teaching can be equally applied to TBC.

"Rab1" refers to a small GTPase that controls vesicle traffic from the endoplasmic reticulum (ER) to the Golgi apparatus. Rab1 belongs to the Ras superfamily of GTPases that cycle between inactive GDP-bound and active GTP-bound forms. "Rab1" is meant to encompass Rab1 isoforms, Rab1a and Rab1b. Mammalian Rab1s, particularly human Rab1s, are of particular interest. Exemplary human Rab1 nucleotide and amino acid sequences are described at GenBank Accession Nos. DQ894084 (gi|123994816|gb|DQ894084.2| [123994816]); AM392684 (gi|117646893|emb|AM392684.1|[117646893]); BT019529 (gi|54695927|gb|BT019529.1|[54695927]); BT019528 (gi|54695925|gb|BT019528.1|[54695925]

"Arf1" refers to an ADP-ribosylation factors (ARF) that is a small guanine nucleotide-binding protein. ARFs are involved in vesicular transport and functioning as activators of phospholipase D. The functions of ARF proteins in membrane traffic and organelle integrity are intimately tied to their reversible association with membranes and specific interactions with membrane phospholipids. A common feature of these functions is their regulation by the binding and hydrolysis of GTP. Mammalian Arf1s, particularly human Arf1s are of interest. Exemplary human Arf1 nucleotide and amino acid sequences are described at GenBank Accession Nos. AM393712 (gi|117646241|emb|AM393712.1| [117646241]); AM393595 (gi|117646009|emb|AM393595.1|[117646009]); AM393462 (gi|117645743|emb|AM393462.1| [117645743]); and AM393261 (gi|117645345|emb|AM393261.1|[117645345]).

By "NS5A" or "NS5A polypeptide" is meant a NS5A protein. In embodiments of particular interest, the NS5A polypeptide is a NS5A polypeptide of a virus of the family Flaviviridae, with hepatitis C virus NS5A polypeptide being of particular interest, where the HCV NS5A can be an NS5A of any genotype, with genotype 1 and subgenotypes thereof (e.g., 1a, 1b, 1c, etc.) being of particular interest. HCV NS5A, including the aforementioned primary structures, is reviewed in the following literature: Reyes, 2002, *J. Biomed. Sci.* 9:187-97 and Macdonald et al., 2004, *J. Gen. Virol.* 85:2485-502, incorporated herein by reference. A "functional equivalent" of NS5A or NS5A polypeptide is a polypeptide that is capable of binding to TBC or TBC polypeptide (in pasticular a mammalian TBC 1D20 or human TBC1D20), or a functional equivalent thereof. The "functional equivalent" of NS5A or NS5A polypeptide is characterized by at least one of the following structures: a AH region, Class I polyproline motif (KLLPRLP (SEQ ID NO:8)), hyperphosphorylaton cluster, interferon sensitivity determining region (ISDR), polyproline cluster, and the Class II motifs (PLPPPR-X2-PVPPPR (SEQ ID NO:11; "X2" is any two amino acids).

By "Flaviviridae virus" or "flavivirus" is meant any virus from the Flaviviridae family, including those viruses that infect humans and non-human animals. The polynucleotide and polypeptides sequences encoding these viruses are well known in the art, and may be found at NCBI's GenBank database, e.g., as Genbank Accession nos. NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety. In general the term "flavivirus" includes any member of the family Flaviviridae, including, but not limited to, Dengue virus, including Dengue virus 1, Dengue virus 2, Dengue virus 3, Dengue virus 4 (see, e.g., GenBank Accession Nos. M23027, M19197, A34774, and M14931); Yellow Fever Virus; West Nile Virus; Japanese Encephalitis Virus; St. Louis Encephalitis Virus; Bovine Viral Diarrhea Virus (BVDV); and Hepatitis C Virus (HCV); and any serotype, strain, genotype, subtype, quasispecies, or isolate of any of the foregoing. Where the flavivirus is HCV, the HCV is any of a number of genotypes, subtypes, or quasispecies, including, e.g., genotype 1, including 1a and 1b, 2, 3, 4, 6, etc. and subtypes (e.g., 2a, 2b, 3a, 4a, 4c, etc.), and quasispecies.

By "heterologous" is meant that a first entity and second entity are provided in an association that is not normally found in nature.

The term "interaction", such as used in the context of interaction between a TBC1D20 and NS5A, refers to binding or other association between polypeptides which facilitates replication of a Flaviridae viral genome in a host cell under suitable conditions. Interaction can be detected directly (e.g., by detecting binding of TBC1D20 and NS5A) or indirectly by assaying a product of a reaction that occurs as a result of the interaction (e.g., increase in Rab-GTPase activity, particularly Rab1 GTPase activity, or induction of viral replication).

By "test agent" or "candidate agent", "candidate", or "candidate modulator", or grammatical equivalents herein, which terms are used interchangeably herein, is meant any molecule (e.g. proteins (which herein includes proteins, polypeptides, and peptides), small (i.e., 5-1000 Da, 100-750 Da, 200-500 Da, or less than 500 Da in size), or organic or inorganic molecules, polysaccharides, polynucleotides, etc.) which are to be tested for activity in modulating an activity associated with TBC1D20 transcription, translation, or expression, TBC1D20 and NS5A interaction or binding, Rab1 expression and/or activity, and/or Arf1 expression and/or activity. In certain embodiments, the test agent binds to a nucleic acid encoding the TBC1D20 polypeptide. In certain embodiments, the test agent binds to the TBC1D20 polypeptide. In certain embodiments, the test agent binds to the NS5A polypeptide. In other embodiments, the test agent affects Rab1 and/or Arf1 activity, e.g, by reducing Rab1 and/or Arf1 expression. Further exemplary test agents are described herein.

By "screen" or "screening" (as used in the context of the methods to identify a test agent having a desired activity) is meant that a test agent is subjected to an assay to determine the presence of absence of an activity of interest (e.g., modulation of interaction between TBC1D20 and NS5A; modulation of expression of TBC1D20, Rab1, and/or Arf1; and the like).

By "modulate" is meant that a viral phenotype or cellular phenotype (e.g., viral replication or Rab-GTPase activation) and/or activity of a gene product increased (e.g., up-regulated) or decreased (e.g., down-regulated) in the presence of a modulator (e.g., test agent, e.g., siNA), such that cellular phenotype, gene expression, mRNA or protein level, or gene product activity is greater than or less than that observed in the absence of the modulator. The context of use of the term will make it apparent as to whether increase or decrease in the relevant phenomenon is desired. For example, in the context of inhibiting viral replication (e.g., as in inhibiting replication of HCV) through modulating binding of NS5A and TBC, a desired "modulator" is one that inhibits the NS5A-TBC interaction, reduces TBC (e.g., TBC1D20) activity (e.g., by reducing TBC1D20 expression), reduces Rab1 activity (e.g., by reducing Rab1 expression), and/or reduces Arf1 activity (e.g., by reducing Arf1 expression). In another example, in the context of increasing viral replication (e.g., as in increasing replication of HCV for purposes of producing more research material or a viral protein for producing a vaccine) through modulating binding of NS5A and TBC, a desired "modulator" is one that increases activity TBC, Rab1, and/or Arf1 in a cell (e.g., a cell line used for HCV virus replication).

By "inhibit", "down-regulate", or "reduce", it is meant that the cellular phenotype, gene expression, or mRNA level, protein level, or activity of one or more proteins or protein subunits (e.g., GAP activity, GTPase activity), in the presence of a test agent is reduced below that observed in the absence of the test agent. In general, an inhibitory agent generally reduces an activity of interest (e.g., viral replication, expression of a target gene) by at least 20%, e.g., at least 30%, at least 40%, at least 50%, at least 60%, at least 70%, at least 80%, at least 90%, at least 95%, up to about 99% or 100% in an assay, as compared to the same assay performed in the absence of the compound. In some embodiments, e.g., where inhibition of viral replication using a siNA is involved, inhibition, down-regulation or reduction with an siNA molecule is below that level observed in the absence of the siNA molecule or in the presence of a negative control (e.g., an inactive or attenuated molecule, or an siNA molecule with scrambled sequence and/or mismatches).

By "in vitro" is meant a cell-free or cell-based assay that does not involve a whole animal (e.g., is not conducted in vivo).

By "nucleic acid" herein is meant either DNA or RNA, or molecules which contain both deoxy- and ribonucleotides. The nucleic acids include genomic DNA, cDNA and oligonucleotides including sense and anti-sense nucleic acids. Also siNAs, such as siRNAs, are included. Such nucleic acids may also contain modifications in the ribose-phosphate backbone to increase stability and half life of such molecules in physiological environments.

The nucleic acid may be double stranded, single stranded, or contains portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes herein. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes herein.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

Where a nucleic acid is said to hybridize to a recited nucleic acid sequence, hybridization is under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment.

Similarly, "polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived. It should be noted that, as will be clear from the context, reference to TBC, NS5A, Rab1, and Arf1 can refer to polypeptides or to the corresponding polynucleotide encoding such polypeptides.

As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of an polypeptide. Polypeptides suitable for use can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, particularly rat or human, from any source whether natural, synthetic, semi-synthetic or recombinant. In general, polypeptides comprising a sequence of a human polypeptide are of particular interest. For example, "TBC1D20 polypeptide", "Rab1 polypeptide" and "Arf1 polypeptide" can refer to the amino acid sequences of TBC1D20 polypeptide, Rab 1 polypeptide, and Arf1 polypeptide obtained from a human, and is meant to include all naturally-occurring allelic variants, and is not meant to limit the amino acid sequence to the complete, native amino acid sequence associated with the recited protein molecule.

The term "derived from" indicates molecule that is obtained directly from the indicated source (e.g., when a protein directly purified from a cell, the protein is "derived from" the cell) or information is obtained from the source, e.g. nucleotide or amino acid sequence, from which the molecule can be synthesized from materials other than the source of information (e.g., when the nucleotide sequence of the TBC1D20 gene is used in the chemical synthesis of an oligonucleotide, the oligonucleotide is derived from the TBC1D20 gene).

The term "isolated" indicates that the recited material (e.g, polypeptide, nucleic acid, etc.) is substantially separated from, or enriched relative to, other materials with which it occurs in nature (e.g., in a cell). A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. As will be evidence from the context in which the term is used, subject and patient refer to a subject or patient susceptible to infection by a a Flaviviridae virus, particularly HCV.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "antibody" and "functional fragment thereof" refers to an immunoglobulin molecule that specifically binds to, or is immunologically reactive with a particular antigen, and includes both polyclonal and monoclonal antibodies. The term also includes genetically engineered or otherwise modified forms of immunoglobulins, such as chimeric antibodies, humanized antibodies, heteroconjugate antibodies (e.g., bispecific antibodies, diabodies, triabodies, and tetrabodies), and antigen binding fragments of antibodies, including e.g., Fab', F(ab')$_2$, Fab, Fv, rIgG, and scFv fragments. The term "scFv" refers to a single chain Fv antibody in which the variable domains of the heavy chain and of the light chain of a traditional two chain antibody have been joined to form one chain. Exemplary antigens include TBC, particularly TBC1D20; NS5A, particularly NS5A of HCV; Rab1 (e.g., Rab1a, Rab1b); and Arf1.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the novel unit dosage forms depend on the particular compound (e.g., phenylglycine-containing compound or sulfonamide containing compound) employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

Other definitions of terms appear throughout the specification.

DETAILED DESCRIPTION OF EXEMPLARY EMBODIMENTS

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Introduction

The disclosure provides methods and compositions for identifying agents for treating infection by viruses that encode a NS5A protein, or functional equivalent thereof, e.g., hepatitis C virus (HCV) or other members of the family Flaviviridae, or encode a viral protein that inhibits a TBC protein in activation of a Rab-GTPase. In general, the methods involve contacting a test agent with a NS5A polypeptide, or functional equivalent thereof, and a TBC polypeptide, and determining the effect of the test agent on NS5A-mediated activity of a TBC polypeptide. For example, a test agent that inhibits binding between the NS5A polypeptide, or functional equivalent thereof, and the TBC polypeptide is an antiviral agent, e.g., an anti-HCV agent. In another example, a test agent that reduces expression of TBC polypeptide is an anti-viral agent. In a further examples, a test agent that reduces activity (e.g., through reducing expression) of Rab1 and/or Arf1 is an antiviral agent. The subject methods and compositions find use in a variety of therapeutic and screening applications.

As set out in the Examples below, it has been found that HCV NS5A polypeptide binds TBC1D20 polypeptide, and that this interaction is essential for viral replication. In addition, NS5A actually enhances TBC1D20-mediated GAP activity. Furthermore, GTPase activity of Rab1 and Arf1 are modulated by TBC1D20. Decreasing expression of Rab1 was found to decrease HCV viral replication, thus indicating that Rab1 and Arf1 are both targets for antiviral agents. Further, neither reduction of TBC1D20 expression nor Rab1 expression adversely or obviously affects cell viability. Accordingly, the interaction between the HCV NS5A polypeptide and TBC1D20 polypeptide, as well as TBC1D20 activity and activity Rab1 and Arf1, the GTPases modulated by TBC1D20, can serve as targets for antiviral therapy. Modulating "activity" of a target polypeptide can involve, for example, direct inhibition (or stimulation) by disrupting a polypeptide-polypeptide interaction (e.g., TBC1D20-NS5A interaction, TBC1D20-Rab1 interaction, TBC1D20-Arf1 interaction), as well as decreasing expression of a polypeptide (e.g., decreasing expression of TBC1D20, Rab1, and/or Arf1).

In addition, because other viruses, e.g., viruses of the family Flaviviridae etc., also have NS5A polypeptides, the methods also encompass identification of antiviral agents that inhibit replication by other viruses. Furthermore, since TBC1D20 is an example of a large family of host cell proteins containing a TBC/rabGAP consensus domain, other TBC proteins can also be useful as antiviral targets.

In some embodiments, the method involves contacting a test agent with a NS5A polypeptide, or functional equivalent thereof, and a TBC1D20 polypeptide, and determining the effect of the test agent on the binding activity between the NS5A polypeptide, or functional equivalent thereof, and the TBC1D20 polypeptide. A test agent that inhibits binding between the NS5A polypeptide, or functional equivalent thereof, and the TBC1D20 polypeptide is an anti-viral agent, e.g., an anti-HCV agent.

In some embodiments, the methods involve contacting a test agent with the TBC1D20 polypeptide, and determining the effect of the test agent on the Rab-GTPase activating activity of the TBC1D20 polypeptide. A test agent that reduces the Rab-GTPase activating activity of the TBC1D20 polypeptide is an anti-viral agent, e.g., an anti-HCV agent. In specific embodiments, the Rab-GTPase activating activity is assessed by assessing GTPase activity of Rab1, by assessing GTPase activity of Arf1, or both.

In some embodiments, the methods involve contacting a test agent with a nucleic acid that encodes a TBC1D20 polypeptide, a Rab1 polypeptide, or an Arf1 polypeptide, and determining the effect of the test agent on the expression of the TBC1D20 polypeptide, Rab1 polypeptide, or Arf1 polypeptide. A test agent that inhibits expression of these target polypeptides is an anti-viral agent, e.g., an anti-HCV agent.

The methods and compositions for identifying agents for inhibiting viral replication can be targeted to identify agents that inhibit viral replication of a NS5A-encoding virus, with HCV and Flaviviridae viruses being of particular interest. Such antiviral compositions can be applied to the treatment of virus infection (e.g., to inhibit replication, reduce viral load, and the like). In general, the methods for identifying a test agent that reduces the binding between NS5A and TBC1D20. In some embodiments, the reduction of binding between NS5A and TBC1D20 is brought about by the direct competition of the test agent with binding either NS5A or TBC1D20. In some embodiments, the test agent directly binds NS5A. In one embodiment, the test agent has a binding affinity with NS5A that is greater than the binding affinity of TBC1D20 for NS5A. In some embodiments, the test agent directly binds TBC1D20. In another embodiment, the test agent has a binding affinity with TBC1D20 that is greater than the binding affinity of NS5A for TBC1D20. In other embodiments, the reduction of binding between NS5A and TBC1D20 is brought about by the reduction of expression of TBC1D20. A test agent that reduces binding between NS5A and TBC1D20 is an anti-viral agent, e.g., an anti-HCV agent.

Methods of inhibiting cellular replication of any virus encoding an NS5A protein, or functional equivalent thereof, are contemplated by the present disclosure. For example, Flaviviridae virus, particularly HCV, replication may be inhibited using the subject methods. The disclosure also provides kits for use in the subject methods are provided. The subject methods and compositions find use in a variety of therapeutic and screening applications.

NS5A encoding viruses include Flaviviridae family viruses, include, but are not limited to flaviviruses, pestiviruses and hepatitis C viruses that include, yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Hepatitis C virus; Kunjin virus; Central European encephalitis virus; Russian spring-summer encephalitis virus; Powassan virus; Kyasanur Forest disease virus; and Omsk hemorrhagic fever virus. HCV is of particular interest.

Identification of anti-HCV agents, and their use in inhibiting HCV replication and treating HCV infection, is of particular interest. The HCV contemplated by the invention may be of any genotype (genotype 1, 2, 3, 4, 5, 6, and the like), as well as subtypes of an HCV genotype (e.g., 1a, 1b, 2a, 2b, 3a, etc.)). Because currently HCV genotype 1 is normally the most difficult to treat, HCV genotype 1 and genotype 1 subtypes are of particular interest.

While the disclosure below refers to HCV, such is only for clarity and is not intended to limit the invention as described in more detail below to HCV. As noted above, the invention can be applied to any virus encoding a NS5A protein, e.g., a Flaviviridae virus having an NS5A polypeptide.

For convenience, the compositions suitable for use in the methods are described first, followed by a discussion of methods for screening for anti-HCV agents. This discussion is followed by a description of methods of inhibiting HCV in a cell, a review of representative applications in which the subject methods find use, and subject kits provided for practicing the subject methods.

NS5A Polypeptides

An "NS5A polypeptide" is any polypeptide having an amino acid sequence of a Flaviviridae NS5A polypeptide and that is capable of binding a TBC1D20 polypeptide. In one embodiment, the NS5A polypeptide binds to the TBC1D20 polypeptide. Of particular interest are NS5A polypeptides that interact with a specific region of TBC1D20 (amino acids 269 to 403) (see FIG. 3).

In some embodiments, the NS5A polypeptide comprises the amino acid sequence 1-100 of the NS5A protein of HCV. In other words, an NS5A polypeptide is any polypeptide that is the functional equivalent of the NS5A of HCV (e.g., in another virus, e.g., in a virus of the Flaviviridae virus family (e.g., HCV, BVDV, and the like), a fusion protein containing a functional fragment of the NS5A polypeptide operably linked to a fusion partner, a naturally-occurring NS5A protein, or the like. Such polypeptides find use in, e.g., screening assays for anti-viral agents. Functional equivalents of the NS5A polypeptide can be determined by a binding assay, such as the GAL4-based yeast two-hybrid analysis described in Example 2 ("TBC1D20 interacts with the N-terminus of NS5A"). Exemplary NS5A amino acid sequences are found in the following Genbank Accession NOs: BAA14233.1, ABF49964.1, ABF49910.1, ABF49964.1, ABF49910.1, ABF49974.1, ABF49900.1, AAV83515.1, ABF49898.1, ABF50027.1, AAB87527.2, ABF49936.1, AAG22692.2, ABF49978.1, ABF50008.1, AAY23031.1, AAY23071.1, AAQ86518.1, AAQ86475.1, AAQ86468.1, AAQ86479.1, AAQ85565.1, AAQ86511.1, AAQ86419.1, AAQ86534.1, AAQ86036.1, AAQ86287.1, AAQ85335.1, AAY23087.1, AAQ86512.1, AAQ86538.1, each of which are incorporated by reference herein.

Provided with the NS5A amino acid sequences exemplified herein, as well as others available in the art, one of ordinary skill in the art would readily recognize based on an alignment of these amino acid sequences the residues that are identical, conserved (e.g., by conservative amino acid substitution), or non-conserved between between NS5A polypeptides of all HCV isolated, among particular HCV genotypes (e.g., NS5A polypeptides of HCV of genotype 1, NS5A polypeptides of HCV of genotype 2, etc.), among HCV subtypes ((e.g., NS5A polypeptides of HCV of genotype 1a, NS5A polypeptides of HCV of genotype 1b, etc.), among HCV quasispecies, and the like. Provided with this guidance, production of NS5A variants and fragments of NS5A useful in the methods described herein will be readily apparent and within the skill in the art.

In some embodiments, the NS5A polypeptide is provided as a fusion protein. The fusion partner attached to the NS5A polypeptide may be any heterologous protein of interest reporter protein, e.g., a light emitting reporter such as a fluorescent or luminescent polypeptide (e.g., GFP or luciferase), may contain sequences from another nucleotide-binding polypeptide (e.g., a G-protein), or may contain sequence from any other polypeptide. In particular embodiments, an NS5A polypeptide is a fusion protein between an NS5A and a partner such as GST, poly-histidine, or avidin. These fusions are convenient for assay formats using glutathione, nickel, or biotin coupled to solid supports (using beads or a microtiter plate well, etc.).

Variant NS5A polypeptides that retain TBC- or TBC1D20-binding activity typically comprise a sequence that has at least 50% sequence similarity with the amino acid sequence of residues 1-100 of the HCV NS5A. Usually there is at least 70% sequence similarity. More usually, there is at least 80% sequence similarity or at least 90% sequence similarity, or at least 95% sequence similarity.

The disclosure further provides for in vivo screening assays comprising the use of nucleic acids that encode the NS5A polypeptide or the TBC polypeptide which are capable of expressing the polypeptide(s) in a suitable host cell. In some embodiments, suitable vectors comprise the subject nucleic acid. In many embodiments, the subject nucleic acid sequences may be expressed in a host after the sequences have been operably linked to an expression control sequence, including, e.g. a promoter. The subject nucleic acids are also typically placed in an expression vector that can replicate in a host cell either as an episome or as an integral part of the host chromosomal DNA. Commonly, expression vectors will contain selection markers, e.g., tetracycline or neomycin, to permit detection of those cells genetically modified with the desired DNA sequences (see, e.g., U.S. Pat. No. 4,704,362, which is incorporated herein by reference). Vectors, including single and dual expression cassette vectors are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Suitable vectors include viral vectors, plasmids, cosmids, artificial chromosomes (human artificial chromosomes, bacterial artificial chromosomes, yeast artificial chromosomes, etc.), mini-chromosomes, and the like. Retroviral, adenoviral and adeno-associated viral vectors may be used.

TBC Polypeptides

A "TBC polypeptide" is meant a protein characterized by at least one of 1) a TBC/Rab-GAP consensus domain (Reczek et al., 2001, *J. Cell Bid.* 153(1):191-205); 2) an amino acid sequence of SEQ ID NO:4, SEQ ID NO:5 or SEQ ID NO:6 (FIG. 11); 3) the amino acid sequences of DLHRQFPFHEMF (SEQ ID NO:12), GYCQAQAPXAAVLLMHMFAEQA FWC (SEQ ID NO:8), LYMTEWFMC (SEQ ID NO:9) or WDMFFCEG (SEQ ID NO: 10); and 4) ability to bind NS5A, wherein the TBC protein is capable of activating Rab-GTPase. Exemplary amino acid sequences of TBC proteins are found in the following GenBank Accession Nos.: NP_653229.1, BAC86808.1, AAI11320.1, AAH79383.1, BAE42961.1, AAH40089.1, XP 861927.1, BAE22209.1, XP 855768.1 XP_618002.2, AAH57027.1, NP_055945.1, XP_855810.1, each of which are incorporated by reference herein. With the TBC amino acid sequences exemplified herein, as well as others available in the art, one of ordinary skill in the art would readily recognize based on an alignment of these amino acid sequences the residues that are identical, conserved (e.g., by conservative amino acid substitution), or non-conserved between TBC polypeptides. With this guidance, production of TBC variants and fragments of TBC useful in the methods described herein will be readily apparent and within the skill in the art.

TBC are discussed in the following literature, e.g., Itoh et al., "Identification of EP164 as a GTPase-activating protein specific for Rab27A," 2006, *J. Biol. Chem.* Aug. 21 [epub ahead of print]; Itoh et al., 2006, *Genes Cells* 11(9):1023-37; Pan et al., 2006, *Nature* 442(7100):303-6; and Reczek et al., 2001, which are incorporated by reference herein in their entirety. In embodiments of particular interest, the TBC polypeptide is a mammalian TBC polypeptide, with human TBC polypeptide being of particular interest.

An example of a TBC protein of particular interest is a TBC1 protein. An example of a TBC1 protein of particular interest is a TBC1D20 or TBC1D20 polypeptide. TBC1D20 polypeptides include the peptides of the sequences described above. The references cited above provide descriptions of the sources of some of these TBC1D20 polypeptides and the methods to identify the functional fragments. Also, by "TBC1D20" or "TBC1D20 polypeptide" is meant a TBC1D20 protein. In embodiments of particular interest, the TBC1D20 polypeptide is a mammalian TBC1D20 polypeptide, with human TBC1D20 polypeptide being of particular interest. The amino acid sequence of TBC1D20 is depicted in FIG. 12, and the nucleotide sequence which encodes TBC1D20 is depicted in FIG. 13. TBC1D20 is an exemplary embodiment of TBC, and when TBC1D20 is mentioned within this specification, the teaching can be equally applied to TBC.

Figures 3, 4:
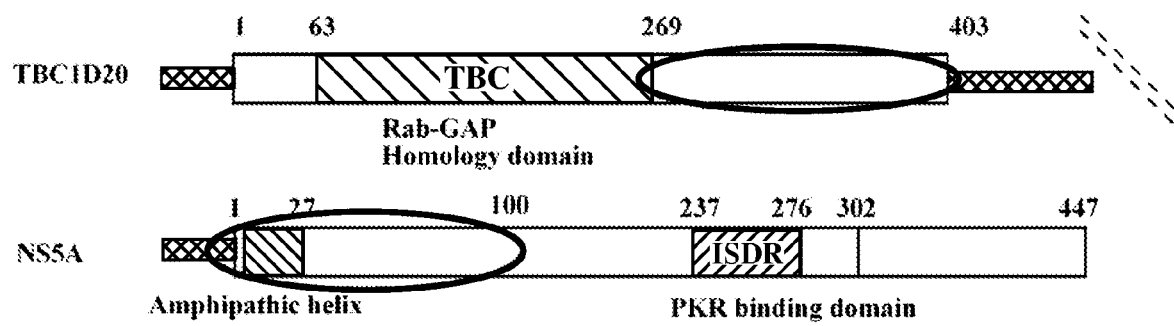
FIG. 3 depicts a schematic representation of both interacting proteins and various important domains are highlighted.
FIG. 4 is a table showing the results of the deletion analysis where a series of deletion mutants is prepared for each of the binding partners and their interactions are tested in a two-hybrid assay. The numbers represent the amino acid present in the mutants. "V" indicates that growth on selective media is consistent with an interaction between the two partner proteins, NS5A and TBC1D20. Three mutants are non-informative (Δ4-27, m3 237-447 and m4 237-302) as they exhibit self-activation.

In some embodiments, the TBC polypeptide comprises the amino acid sequence 269-403 of the human TBC1D20 protein (see FIGS. 3 and 12). In other words, an TBC polypeptide is any polypeptide that is the functional equivalent of the human TBC1D20 of HCV (e.g., in another human TBC protein, e.g., in a TBC protein of a non-human mammal), a fusion protein containing a functional fragment of the TBC polypeptide operably linked to a fusion partner, a naturally-occurring TBC protein, or the like. Such polypeptides find use in, e.g., screening assays for anti-viral agents.

Provided with the TBC1D20 amino acid sequences exemplified herein, as well as others available in the art, one of ordinary skill in the art would readily recognize based on an alignment of these amino acid sequences the residues that are identical, conserved (e.g., by conservative amino acid substitution), or non-conserved between between TBC1D20 polypeptides. Provided with this guidance, production of TBC1D20 variants and fragments of TBC1D20 useful in the methods described herein will be readily apparent and within the skill in the art.

In some embodiments, the TBC1D20 polypeptide is provided as a fusion protein. The fusion partner attached to the TBC1D20 polypeptide may be amy heterologous protein of interest reporter protein, e.g., a light emitting reporter such as a fluorescent or luminescent polypeptide (e.g., GFP or luciferase), may contain sequences from another nucleotide-binding polypeptide (e.g., a G-protein), or may contain sequence from any other polypeptide. In particular embodiments, a TBC1D20 polypeptide is a fusion protein between an TBC1D20 and a partner such as GST, poly-histidine, or avidin. These fusions are convenient for assay formats using glutathione, nickel, or biotin coupled to solid supports (using beads or a microtiter plate well, etc.).

RAB1 Polypeptides X

"Rab1" refers to a small GTPase that controls vesicle traffic from the endoplasmic reticulum (ER) to the Golgi apparatus. Rab1 belongs to the Ras superfamily of GTPases that cycle between inactive GDP-bound and active GTP-bound forms. "Rab1" is meant to encompass Rab1 isoforms, Rab1a and Rab1b. Mammalian Rab1s, particularly human Rab1s, are of particular interest. Exemplary human Rab1 nucleotide and amino acid sequences are described at GenBank Accession Nos. DQ894084 (gi|123994816|gb|DQ894084.2| [123994816]); AM392684 (gi|117646893|emb|AM392684.1|[117646893]); BT019529 (gi|54695927|gb|BT019529.1|[54695927]); BT019528 (gi|54695925|gb|BT019528.1|[54695925]

Provided with the Rab1 nucleic acid and amino acid sequences exemplified herein, as well as others available in the art, one of ordinary skill in the art would readily recognize based on an alignment of these amino acid sequences the residues that are identical, conserved (e.g., by conservative amino acid substitution), or non-conserved between Rab1 polypeptides. Provided with this guidance, production of Rab1 variants and fragments of Rab1 useful in the methods described herein will be readily apparent and within the skill in the art.

In some embodiments, the Rab1 polypeptide is provided as a fusion protein. The fusion partner attached to the Rab1 polypeptide may be any heterologous protein of interest reporter protein, e.g., a light emitting reporter such as a fluorescent or luminescent polypeptide (e.g., GFP or luciferase), may contain sequences from another nucleotide-binding polypeptide (e.g., a G-protein), or may contain sequence from any other polypeptide. In particular embodiments, a Rab1 polypeptide is a fusion protein between a Rab1 and a partner such as GST, poly-histidine, or avidin. These fusions are convenient for assay formats using glutathione, nickel, or biotin coupled to solid supports (using beads or a microtiter plate well, etc.).

ARF1 Polypeptides

"Arf1" refers to an ADP-ribosylation factors (ARF) that is a small guanine nucleotide-binding protein. ARFs are involved in vesicular transport and functioning as activators of phospholipase D. The functions of ARF proteins in membrane traffic and organelle integrity are intimately tied to their reversible association with membranes and specific interactions with membrane phospholipids. A common feature of these functions is their regulation by the binding and hydrolysis of GTP. Mammalian Arf1s, particularly human Arf1s are of interest. Exemplary human Arf1 nucleotide and amino acid sequences are described at GenBank Accession Nos. AM393712 (gi|11764624|emb|AM393712.1|[117646241]); AM393595 (gi|117646009|emb|AM393595.1| [117646009]); AM393462 (gi|117645743|emb|AM393462.1|[117645743]); and AM393261 (gi|117645345|emb|AM393261.1| [117645345]).

Provided with the Arf1 nucleic acid and amino acid sequences exemplified herein, as well as others available in the art, one of ordinary skill in the art would readily recognize based on an alignment of these amino acid sequences the residues that are identical, conserved (e.g., by conservative amino acid substitution), or non-conserved between Arf1 polypeptides. Provided with this guidance, production of Arf1 variants and fragments of Arf1 useful in the methods described herein will be readily apparent and within the skill in the art.

In some embodiments, the Arf1 polypeptide is provided as a fusion protein. The fusion partner attached to the Arf1 polypeptide may be any heterologous protein of interest reporter protein, e.g., a light emitting reporter such as a fluorescent or luminescent polypeptide (e.g., GFP or luciferase), may contain sequences from another nucleotide-binding polypeptide (e.g., a G-protein), or may contain sequence from any other polypeptide. In particular embodiments, a Arf1 polypeptide is a fusion protein between an Arf1 and a partner such as GST, poly-histidine, or avidin. These fusions are convenient for assay formats using glutathione, nickel, or biotin coupled to solid supports (using beads or a microtiter plate well, etc.).

Host Cells

E. coli is a prokaryotic host useful for cloning the nucleic acid sequences. Other microbial hosts suitable for use include bacilli, such as Bacillus subtilus, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Polypeptides may be expressed in prokaryotes or eukaryotes in accordance with conventional ways, depending upon the purpose for expression. Such methods are provided in WO 2002/089731 and U.S. application Ser. No. 10/528,377, filed Jan. 4, 2006, which are incorporated by reference herein in their entirety.

In embodiments of particular interest, the host cell is a mammalian cell useful in a screening assay as described herein. Where the screening methods involves detection of TBC polypeptide—NS5A polypeptide interaction, and/or assessing Rab1 and/or Arf1 activity, the host cell can be any appropriate host cell in which such interactions occur, including host cells that can be made recombinant for one or both of the TBC and/or NS5A polypeptide. In such embodiments, the host cells are usually any of a variety of cells, usually eukaryotic cells (e.g., yeast, insect, mammalian, etc.), more usually mammalian cells.

Use of mammalian cells, such as human cells, is of particular interest. In embodiments of particular interest, the cell can support HCV replication and, optionally, is susceptible to HCV infection. In certain embodiments the human cell is a CHOP cell, a Huh-7 cell or a H9C2 cell, B-cell lines including B-cell lymphoma cells, and the cell is chosen because it is susceptible to infection by HCV or can support the replication of HCV or HCV replicons. The latter include a wide variety of cells (including but not limited to primary human, mouse, or rat liver cells, or cell lines originally derived from primary cells such as HeLa, Hepa-6, MDCK, etc.).

In some embodiments, where HCV viral replication is to be detected, the cell is susceptible to infection by a HCV virion and/or which can support HCV viral replication (e.g., such as in a cell genetically modified to provide an assay system for HCV replication). Exemplary cells include human cells susceptible to HCV infection and which support HCV replication, and models thereof. Further exemplary cells susceptible to HCV infection, as well as models of HCV replication, useful in the methods disclosed herein include those described in U.S. Pat. No. 5,679,342; U.S. Pat. No. 5,922,857; U.S. Pat. No. 5,968,775; U.S. Pat. No. 6,057,093; U.S. Pat. No. 6,706,874; and U.S. Pat. No. 7,018,984.

In addition, the disclosure contemplates use of animal models of viral infection, particularly HCV infection, which can be used to assess activity of an agent in vivo following identification of an activity of interest in an assay described herein. Furthermore. NS5A-TBC1D20 binding may be detected in such animal models by measuring hepatitis C disease progression by methods well known to those of ordinary skill in the art. Exemplary animal models for HCV replication include the chimeric liver animal model described in U.S. Pat. No. 6,509,514.

Nucleic Acid Molecules, Polypeptide Production Methods, Expression Vectors, Fusion Proteins NS5A polypeptides, TBC1D20 polypeptides, Rab1 polypeptides, and Arf1 polypeptides for use in the assays and complexes described herein can be produced according to methods known in the art. In general, such methods involve production either in any host cell (e.g., for production of proteins for use in a cell-free assay) or may be expressed in a host cell in which the assay is to be conducted. In such embodiments, the TBC1D20, Rab1, and/or Arf1 polypeptides may be encoded by a gene endogenous to the host cell or may be encoded by a gene exogenous to the host cell. The NS5A polypeptide may be provided due to HCV infection of the host cell, or may be provided as a recombinant nucleic acid (e.g., in an expression system) in the host cell. Either one or both of a recombinant host cell polypeptide (TBC1D20, Rab1, and/or Arf1) and an NS5A polypeptide may be present in a transient expression system, in an episomal expression system, or as a genomically integrated nucleic acid wherein integration provides expression.

Exemplary expression systems and methods are described in more detail below.

Nucleic Acids

The disclosure provides nucleic acid compositions encoding the NS5A polypeptides, as well as the TBC1D20, Rab1 and Arf1 polypeptides described herein. Exemplary nucleic acid and amino acid sequences for each of these polypeptides are provided herein.

Nucleic acid compositions of particular interest comprise a sequence of DNA having an open reading frame that encodes a protein of interest (e.g., NS5A, TBC1D20, Rab1, Arf1) and is capable, under appropriate conditions, of being expressed as a protein.

In general, nucleic acids encoding a polypeptide of interest may be present in an appropriate vector for extrachromosomal maintenance or for integration into a host genome, as described in greater detail below. Where the regions associated with biological activity of the polypeptide is known, the nucleic acid may encode all or part of the polypeptide, with the proviso that the polypeptide provides the desired biological activity (e.g., binding between NS5A and TBC1D20, GTP Activating Protein (GAP) activity of TBC1D20, GTPase activity of Rab1 or Arf1).

The polynucleotides of interest and constructs containing such polynucleotides can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual,* 2nd Ed., (1989) Cold Spring Harbor Press, Cold Spring Harbor, N.Y.

Modified nucleic acids can be generated by random mutagenesis or targeted mutagenesis of a parent nucleic acid molecule, using well-known techniques that are routine in the art. The regions of the sequence that tolerate modification (e.g., conservative or non-conservative substitution) can be identified both from the results of the functional assays provided in the Examples below and/or by sequence alignment of isoforms and homologs of a sequence to be modified. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more amino acid residues. Techniques for in vitro mutagenesis (e.g., site-specific mutation) of cloned genes are known. In general, nucleic acids encoding a polypeptide of interest may be present in an appropriate vector for extrachromosomal maintenance or for integration into a host genome, as described in greater detail below. Where the regions associated with biological activity of the polypeptide is known, the nucleic acid may encode all or part of the polypeptide, with the proviso that the polypeptide provides the desired biological activity (e.g., binding between NS5A and TBC1D20, TBC1D20 GAP activity, GTPase activity of Rab1 and/or Arf1).

Vectors

In general, nucleic acids encoding a polypeptide of interest may be present in an appropriate vector for extrachromosomal maintenance or for integration into a host genome, as described in greater detail below. The nucleic acid may encode all or part of the polypeptide, with the proviso that the polypeptide provides the desired biological activity (e.g., binding between NS5A and TBC1D20, TBC1D20 GAP activity, GTPase activity of Rab1 or Arf1). The expression vector may be either self-replicating extrachromosomal vectors or vectors which integrate into a host genome.

Nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading frame. However, enhancers do not have to be contiguous. Linking is accomplished by ligation at convenient restriction sites. If such sites do not exist, the synthetic oligonucleotide adapters or linkers are used in accordance with conventional practice. The transcriptional and translational regulatory nucleic acid will generally be appropriate to the host cell used to express the protein; for example, transcriptional and translational regulatory nucleic acid sequences from *Bacillus* can be used to express the protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In one embodiment, the regulatory sequences include a promoter and transcriptional start and stop sequences.

Promoter sequences contemplated include constitutive promoters and inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, usually two homologous sequences, which flank the expression construct. The integrating vector may be directed to a specific locus in the host cell by selecting the appropriate homologous sequence for inclusion in the vector. Constructs for integrating vectors are well known in the art.

In addition, in one embodiment, the expression vector contains a selectable marker gene to allow the selection of transformed host cells. Selection genes are well known in the art and will vary with the host cell used.

Viral and non-viral vectors may be prepared and used, including plasmids, which provide for replication of DNA of interest and/or expression in a host cell. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transformation and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector.

Alternatively, the desired nucleotide sequence can be inserted by homologous recombination in a cell. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide is expressed in any convenient expression system, including, for example, bacterial, yeast, insect, amphibian and mammalian systems. In the expression vector, a subject polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive.

In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Promoters may be constitutive or regulatable (e.g, inducible). Inducible promoter elements are DNA sequence elements that act in conjunction with promoters and may bind either repressors (e.g. lacO/LAC Iq repressor system in *E. coli*) or inducers (e.g. gal1/GAL4 inducer system in yeast). In such cases, transcription is virtually "shut off" until the promoter is derepressed or induced, at which point transcription is "turned-on."

Expression vectors generally have convenient restriction sites located near the promoter sequence to provide for the insertion of nucleic acid sequences encoding heterologous proteins. A selectable marker operative in the expression host may be present. Expression vectors may be used for, among other things, the screening methods described in greater detail below.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

Specific expression systems of interest include bacterial, yeast, insect cell and mammalian cell derived expression systems. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

Where expression in a bacterial host cell is desired (e.g., for polypeptide production), a suitable bacterial promoter is included in the vector, any nucleic acid sequence capable of binding bacterial RNA polymerase and initiating the downstream (3') transcription of the coding sequence of a protein into mRNA. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon. Bacterial expression vectors may also include a signal peptide sequence that provides for secretion of the protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

In one embodiment, proteins are produced in insect cells. Expression vectors for the transformation of insect cells, and in particular, baculovirus-based expression vectors, are well known in the art. In another embodiment, proteins are produced in yeast cells. Yeast expression systems are well known in the art, and include expression vectors for *S. cerevisiae, Candida albicans* and *C. maltosa, Hansenula polymorpha, Kluyveromyces fragilis* and K lactis, *Pichia guillerimondii, P. methanolica* and *P. pastoris, Schizosaccharomyces pombe,* and *Yarrowia lipolytica*. Promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TW1, and ALG7, which confers resistance to tunicamycin; the neomycin phosphotransferase gene, which confers resistance to G418; and the CUP 1 gene, which allows yeast to grow in the presence of copper ions.

Mammalian expression can be accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

Methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Protein Production Methods

Proteins can be produced by culturing a host cell transformed with an expression vector containing nucleic acid encoding the protein, under the appropriate conditions to induce or cause expression of the protein. The conditions appropriate for protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction.

In a one embodiment, the proteins are expressed in mammalian cells, especially human cells, with cancerous cells, particularly human cancerous cells, being of interest. Mammalian expression systems are also known in the art, and include retroviral systems. A mammalian promoter (i.e., a promoter functional in a mammalian cell) is any DNA sequence capable of binding mammalian RNA polymerase and initiating the downstream (3') transcription of a coding sequence for a protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

The protein may also be made as a fusion protein, using techniques well known in the art. Thus, for example, the protein may be made fusion nucleic acid encoding the peptide or may be linked to other nucleic acid for expression purposes. Similarly, proteins can be linked to tags that are protein labels, such as an immunodetectable label (e.g., FLAG), a enzymatically detectable label (e.g., GST), and/or an optically detectable label (e.g., green fluorescent protein (GFP), red fluorescent protein (RFP), blue fluorescent protein (BFP), yellow fluorescent protein (YFP), luciferase, etc.)

Proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the protein. In some instances no purification will be necessary.

Covalently Modified Proteins

NS5A, TBC1D20, Rab1 and Arf1 polypeptides having covalent modifications, particularly those that confer a feature useful in a screening assay as described below, are also provided herein. Of particular interest are polypeptides modified so as to incorporate a detectable tag.

Detectably Tagged Polypeptides

Polypeptides modified to comprises a tag and useful in the screening methods disclosed herein. By "tag" is meant an attached molecule or molecules useful for the identification or isolation of the attached molecule(s), which can be substrate binding molecules. For example, a tag can be an attachment tag or a label tag. Components having a tag are referred to as "tag-X", wherein X is the component.

The terms "tag", "detectable label" and "detectable tag" are used interchangeably herein without limitation. Usually, the tag is covalently bound to the attached component. By "tag", "label", "detectable label" or "detectable tag" is meant a molecule that can be directly (i.e., a primary label) or indirectly (i.e., a secondary label) detected; for example a label can be visualized and/or measured or otherwise identified so that its presence or absence can be known. As will be appreciated by those in the art, the manner in which this is performed will depend on the label. Exemplary labels include, but are not limited to, fluorescent labels (e.g. GFP) and label enzymes.

Exemplary tags include, but are not limited to, an optically-detectable label, a partner of a binding pair, and a surface substrate binding molecule (or attachment tag). As will be evident to the skilled artisan, many molecules may find use as more than one type of tag, depending upon how the tag is used. In one embodiment, the tag or label as described below is incorporated into the polypeptide as a fusion protein.

As will be appreciated by those in the art, tag-components can be made in various ways, depending largely upon the form of the tag. Components and tags can be attached by a covalent bond. Examples of tags are described below.

Exemplary Tags

In one embodiment, the tag is a polypeptide which is provided as a portion of a chimeric molecule comprising a first polypeptide fused to another, heterologous polypeptide or amino acid sequence. In one embodiment, such a chimeric molecule comprises a fusion of a first polypeptide with a tag polypeptide. The tag is generally placed at the amino- or carboxyl-terminus of the polypeptide. In embodiments in which the tagged polypeptide is to be used in a cell-based assay and is to be expressed a recombinant protein, the tag is usually a genetically encodable tag (e.g., fluorescent polypeptide, immunodetectable polypeptide, and the like).

The tag polypeptide can be, for example, an immunodetectable label (i.e., a polypeptide or other moiety which provides an epitope to which an anti-tag antibody can selectively bind), a polypeptide which serves as a ligand for binding to a receptor (e.g., to facilitate immobilization of the chimeric molecule on a substrate); an enzyme label (e.g., as described further below); or a fluorescent label (e.g., as described further below). Tag polypeptides provide for, for example, detection using an antibody against the tag polypeptide, and/or a ready means of isolating or purifying the tagged polypeptide (e.g., by affinity purification using an anti-tag antibody or another type of receptor-ligand matrix that binds to the tag). The production of tag-polypeptides by recombinant means is within the knowledge and skill in the art.

Production of immunodetectably-labeled proteins (e.g., use of FLAG, HIS, and the like, as a tag) is well known in the art and kits for such production are commercially available (e.g., from Kodak and Sigma). See, e.g., Winston et al., *Genes and Devel.* 13:270-283 (1999), incorporated herein in its entirety, as well as product handbooks provided with the above-mentioned kits. Production of proteins having His-tags by recombinant means is well known, and kits for producing such proteins are commercially available. Such a kit and its use is described in the QIAexpress Handbook from Qiagen by Joanne Crowe et al., hereby expressly incorporated by reference.

Production of polypeptides having an optically-detectable label are well known. An "optically detectable label" includes labels that are detectably due to inherent properties (e.g., a fluorescent label), or which any be reacted with a substrate or act as a substrate to provide an optically detectable (e.g., colored) reaction product (e.g., HRP).

By "fluorescent label" is meant any molecule that may be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 2002 Molecular Probes Handbook, 9th Ed., by Richard P. Haugland, hereby expressly incorporated by reference.

Suitable fluorescent labels include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), -galactosidase (Nolan, et al., Proc Natl Acad Sci USA 85(8):2603-2607 (April 1988)) and *Renilla* WO 92/15673; WO 95/07463; WO 98/14605; WO 98/26277; WO 99/49019; U.S. Pat. No. 5,292,658; U.S. Pat. No. 5,418, 155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925, 558), and *Ptilosarcus* green fluorescent proteins (pGFP) (see WO 99/49019). All of the above-cited references are expressly incorporated herein by reference.

In some instances, multiple fluorescent labels are employed. In one embodiment, at least two fluorescent labels are used which are members of a fluorescence resonance energy transfer (FRET) pair. FRET can be used to detect association/dissociation of NS5A and TBC1D20, TBC1D20 and Rab1, and/or TBC1D20 and Arf1. In general, such FRET pairs are used in in vitro assays.

FRET is phenomenon known in the art wherein excitation of one fluorescent dye is transferred to another without emission of a photon. A FRET pair consists of a donor fluorophore and an acceptor fluorophore (where the acceptor fluorophore may be a quencher molecule). The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Forster radius, which is typically 10-100 angstroms. Changes in the fluorescence emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity.

Binding of such molecules will result in an increased fluorescence emission of the acceptor and/or quenching of the fluorescence 15 emission of the donor. Exemplary FRET pairs (donor/acceptor) include, but are not limited to, EDANS/fluorescien, IAEDANS/fluorescein, fluoresceidtetramethylrhodamhe, fluoresceidLC Red 640, fluoresceidcy 5, fluoresceidCy 5.5 and fluoresceidLC Red.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, DABCYL, QSY 7 and QSY 33. Useful fluorescent donodquencher pairs include, but are not limited to EDANS/DABCYL, Texas RedLDABCYL, BODIPYDABCYL, Lucifer yellowDABCYL, coumarin/DABCYL and fluoresceidQSY 7 dye.

The skilled artisan will appreciate that FRET and fluorescence quenching allow for monitoring of binding of labeled molecules over time, providing continuous information regarding the time course of binding reactions. It is important to remember that attachment of labels or other tags should not interfere with active groups on the interacting polypeptides. Amino acids or other moieties may be added to the sequence of a protein, through means well known in the art and described herein, for the express purpose of providing a linker and/or point of attachment for a label. In one embodiment, one or more amino acids are added to the sequence of a component for attaching a tag thereto, with a fluorescent label being of particular interest.

In other embodiments, detection involves bioluminescence resonance energy transfer (BRET). BRET is a protein-protein interaction assay based on energy transfer from a bioluminescent donor to a fluorescent acceptor protein. The BRET signal is measured by the amount of light emitted by the acceptor to the amount of light emitted by the donor. The ratio of these two values increases as the two proteins are brought into proximity. The BRET assay has been amply described in the literature. See, e.g., U.S. Pat. Nos. 6,020,192; 5,968,750; and 5,874,304; and Xu et al. (1999) *Proc. Natl. Acad. Sci. USA* 96:151-6. BRET assays may be performed by analyzing transfer between a bioluminescent donor protein and a fluorescent acceptor protein. Interaction between the donor and acceptor proteins can be monitored by a change in the ratio of light emitted by the bioluminescent and fluorescent proteins.

Alternatively, binding may be assayed by fluorescence anisotropy. Fluorescence anisotropy assays are amply described in the literature. See, e.g., Jameson and Sawyer (1995) *Methods Enzymol.* 246:283-300.

By "label enzyme" is meant an enzyme which may be reacted in the presence of a label enzyme substrate which produces a detectable product. Label enzymes may also be optically detectable labels (e.g., in the case of HRP). Suitable and exemplary label enzymes include but are not limited to, horseradish peroxidase (HRP), alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzidine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989), which are each hereby incorporated by reference in their entirety.

By "radioisotope" is meant any radioactive molecule. Suitable exemplary radioisotopes include, but are not limited to $^{14}C$, $^{3}H$, $^{32}P$, $^{33}P$, $^{35}S$, $^{125}I$, and $^{131}I$. The use of radioisotopes as labels is well known in the art.

In addition, labels may be indirectly detected, that is, the tag is a partner of a binding pair. By "partner of a binding pair" is meant one of a first and a second moiety, wherein said first and said second moiety have a specific binding affinity for each other. Suitable exemplary binding pairs include, but are not limited to, antigendantibodies (for example, digoxigeninlanti-digoxigenin, dinitrophenyl (DNP)/anti-DNP, dansyl-X-anti-dansyl, Fluoresceidanti-fluorescein, Lucifer yellow/anti-lucifer yellow, and rhodamine anti-rhodamine), biotirdavid (or biotirdstreptavidin) and calmodulin binding protein (CBP)/calmodulin. Other suitable binding pairs include polypeptides such as the FLAG-peptide (Hopp et al., *BioTechnol.* 6:1204-1210 (1988)); the KT3 epitope peptide (Martin et al., Science, 255:192-194 (1992)); tubulin epitope peptide (Skinner et al., *J. Biol. Chem.*, 266: 15 163-15 166 (1991)); and the T7 gene 10 protein peptide tag (Lutz-Freyemuth et al., *Proc. Natl. Acad. Sci. USA,* a:6393-6397 (1990)) and the antibodies each thereto.

In one embodiment, the tag is surface substrate binding molecule. By "surface substrate binding molecule" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate (Field et al., Mol. Cell. Biol., 8:2159-2165 (1988)); the c-myc tag and the 8F9,3C7,6E107 G4, B7 and 9E10 antibody substrates thereto (Evan et al., Molecular and Cellular Biol, 5:3610-3616 (1985)]; and the Herpes Simplex virus glycoprotein D (gD) tag and its antibody substrate (Paborsky et al., Protein Engineering, 3(6): 547-553 (1990)). In general, surface binding substrate molecules can include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin et al., Bioconj, Chem. 2:342-348 (1991); Torchilin et al., supra; Trubetskoy et al., Bioconi. Chem. 33323-327 (1992); King et al., Cancer Res. 54:6176-6185 (1994); and Wilbur et al., Bioconjugate Chem. 5:220-235 (1994) (all of which are hereby expressly incorporated by reference), and attachment of or production of proteins with antigens is described above. Calmodulin-embedded substrates are commercially available and production of proteins with CBP is described in Simcox et al., Strategies 8:40-43 (1995), which is hereby incorporated by reference in its entirety.

Where appropriate, functionalization of labels with chemically reactive groups such as thiols, amines, carboxyls, etc. is generally known in the art. In one embodiment, the tag is functionalized to facilitate covalent attachment.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known. Methods for labeling of proteins with radioisotopes are known in the art. For example, such methods are found in Ohta et al., Molec. Cell 3:535-541 (1999), which is hereby incorporated by reference in its entirety.

The covalent attachment of the tag may be either direct or via a linker. In one embodiment, the linker is a relatively short coupling moiety that is used to attach the molecules. A coupling moiety may be synthesized directly onto a component, e.g. NS5A, and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer.

In one embodiment, the covalent attachment is direct, that is, no linker is used. In this embodiment, the component can contain a functional group such as a carboxylic acid which is used for direct attachment to the functionalized tag. It should be understood that the component and tag may be attached in a variety of ways, including those listed above. What is important is that manner of attachment does not significantly alter the functionality of the component. For example, in tag-TBC polypeptide or tag-NS5A, the tag should be attached in such a manner as to allow for interaction between the TBC polypeptide and the NS5A polypeptide.

In one embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag may depend on the site of attachment to either a linker. Thus, for example, for direct linkage to a carboxylic acid group of a TBC polypeptide or a NS5A polypeptide, amino modified or hydrazine modified tags will be used for coupling via carbodimide chemistry, for example using 1-ethyl-3-(3-dimethylaminopropyl)-carbodimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodimide is first attached to the tag, such as is commercially available for many of the tags described herein.

Host Cells for Use in Assays

Cells suitable for use in the assay methods disclosed herein are generally any higher eukaryotic cell which is capable of supporting HCV replication, e.g., a cell in which HCV is capable of infecting and replicating, or a cell which has been modified recombinantly to provide the necessary components. Usually the host cells in the assays are mammalian cells.

It will be desirable that the cells are an easily manipulated, easily cultured mammalian cell line, usually human cell lines. In other embodiments, cells suitable for use are non-transformed primary human cells.

Exemplary cell lines for use as cells in assays include, but are not necessarily limited to, mammalian cell lines (particularly human cell lines). Specific exemplary cells include, but are not limited to, HCT 116, SW480, T98G, CCD841 CoN, WI-38, NIH 3T3, U-2OS, and HE 293 cells, and the like.

Recombinant Cells

The cell line is most conveniently one that can be readily propagated in culture and is readily manipulated using recombinant techniques. The host cells used for production of such recombinant cells can be any cell discussed above, including cell lines, primary cells, and the like, including primary cancer cells and cancer cell lines. Exemplary cell lines, include, but are not necessarily limited to, mammalian cell lines (particularly human cell lines), such as HCT 116, SW480, T98G, CCD841 CoN, WI-38, NIH 3T3, U-2 OS, and HE 293 cells, and the like.

In general, the recombinant cells can be produced as described above. The constructs can be introduced into the host cell using standard methods practiced by one with skill in the art. Where one or more recombinant polypeptides are to be introduced into the cell as a polynucleotides encoding the one or more polypeptides and an expression cassette, optionally carried on one or more transient expression vectors (e.g., the vector is maintained in an episomal manner by the cell), which comprise the polynucleotides encoding the desired polypeptides. Alternatively, or in addition, the one or more expression constructs encoding one or more polypeptides can be stably integrated into the cell line. In addition or alternatively, one or more of polynucleotides encoding one or more desired polypeptides can be stably integrated into the cell, while one or more other desired polypeptides expressed from one or more transient expression vectors. For example, a polynucleotide encoding a NS5A polypeptide may be stably integrated in the cell line, while a polynucleotide encoding a TBC is expressed from a transient expression vector, or vice versa.

Test Agents

The assays disclosed herein can be adapted to facilitate identification of test agents that act as modulators of NS5A and TBC binding. By "modulator" is meant a compound which can facilitate an increase or decrease in the amount of NS5A and TBC binding, increase Rab-GPTase activity, expression of TBC, or viral replication, or a combination of these and/or other biological activities.

By "test agent" or "candidate agent", "candidate", "candidate modulator", "candidate TBC-NS5A interaction modulator", "candidate TBC expression modulator" or grammatical equivalents herein, which terms are used interchangeably herein, is meant any molecule (e.g. proteins (which herein includes proteins, polypeptides, and peptides), small (i.e., 5-1000 Da, 100-750 Da, 200-500 Da, or less than 500 Da in size), or organic or inorganic molecules, polysaccharides, polynucleotides, etc.) which are to be tested for activity in modulating an activity associated with viral replication and mediated through binding of NS5A and TBC1D20, inhibition of activity (e.g., expression) of TBC1D20, Rab1, and/or Arf1.

In another embodiment, the candidate modulators are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

Assays to Identify Agents that Modulate Viral Replication

The disclosure provides methods for identifying agents that modulate viral replication. The screening methods may be designed a number of different ways, where a variety of assay configurations and protocols may be employed, as are known in the art. In general, the assay methods provide for identification of agents that modulate binding between NS5A and TBC, for identification of agents that modulate expression of one or more of TBC (e.g., TBC1D20), Rab1, and Arf1, and/or for identification of agents that provide for a reduction in stimulated GAP activity of TBC1D20 in the presence of NS5A (e.g, by assessing GTPase activity of Rab1 or Arf1). It will be appreciated that the assays can be performed alone, in series or parallel, and in some instances can be performed in a single assay (e.g., NS5A and TBC binding, and TBC expression can be assessed in the same assay).

It will be readily apparent to the ordinarily skilled artisan upon reading the present disclosure that appropriate positive and/or negative controls may be included in the inventive assays. Exemplary positive controls include an assay performed with an agent which is known to modulate the parameter being tested. Exemplary negative controls include an assay performed in the absence of a component essential for the activity (e.g., NS5A or TBC).

The assays can be used to identify test agents having a desired activity; to confirm activity of agents known to have activity in modulation of viral replication, Rab-GTPase activity, TBC expression and/or NS5A and TBC binding.

The screening methods provided herein include assays to identify a test agent that modulates binding of a NS5A polypeptide with a TBC polypeptide (e.g., a TBC1D20 polypeptide). Such assays can be conducted in vitro (e.g., in vitro binding assays, also referred to as cell-free binding assays) or in vivo (e.g, using cells having detectably labeled NS5A, detectably labeled TBC1D20, or both). Where the assay is a cell-free assay, it may be desirable to provide TBCD12 in a synthetic membrane or cellular membrane isolate. Exemplary assays are described below.

The assay can involve, for example, contacting the NS5A polypeptide and the TBC1D20 polypeptide with a test agent, and directly determining the effect, if any, of the test agent on the binding of the NS5A polypeptide and the TBC1D20 polypeptide. This method can be conducted in vitro (i.e., cell-free) in a reaction mixture, using isolated polypeptides. Where desired or required, the in vitro assay reaction mixture can comprise cell extracts (e.g., cell cytoplasm extracts) so as to provide cellular components required for interaction between the NS5A polypeptide and the TBC1D20 polypeptide. The cell extract is prepared from a cell in which TBC1D20 polypeptide is naturally expressed (e.g., due to endogenous activity or activity as a result of genetic modification). Alternatively, the assay can be performed in a cell-based assay, where the cell can provide for assay components by expression from an endogenous or non-endogenous (recombinant) nucleic acid.

Formation of a binding complex between the NS5A polypeptide and the TBC1D20 polypeptide can be detected using any known method. Suitable methods include, but are not limited to: a FRET assay (including fluorescence quenching assays); a BRET assay; an immunological assay; and an assay involving binding of a detectably labeled protein to an immobilized protein (e.g., binding of detectably labeled TBC1D20 polypeptide to the NS5A polypeptide, or binding of a detectably labeled. NS5A polypeptide to the TBC1D20 polypeptide.

Immunological assays binding of a detectably labeled protein can be provided in a variety of formats. For example, immunoprecipitation assays can be designed, wherein the NS5A/TBC1D20 complex is detected by precipitating the complex with antibody specific for NS5A, TBC1D20, or antibody specific for an immunodetectable tag of a NS5A fusion protein and/or a TBC1D20 fusion protein. In some formats, either NS5A or TBC1D20 can be immobilized directly or indirectly (e.g., by binding to an immobilized antibody or other immobilized protein) on an insoluble support. Insoluble supports include, but are not limited to, plastic surfaces (e.g., polystyrene, and the like) such as a multi-well plate; beads, including magnetic beads, plastic beads, and the like; membranes (e.g., polyvinylpyrrolidone, nitrocellulose, and the like); etc. Bound complexes can be detected directly (e.g., by the presence of a detectable label of NS5A or TBC1D20 in a complex) or indirectly (e.g., by use of an antibody the specifically binds an immunodetectable tag present on one of the binding partners of the complex).

In cell-based embodiments, formation of complexes of NS5A and TBC1D20 can be detected in a variety of ways. For example, after contacting the cell with the agent and incubating for a sufficient amount of time, the presence or absence of complexes can be detected. This can be accomplished by producing cell extracts by, after allowing time for production of NS5A and TBC1D20, lysing the cells and examining lysates for the NS5A-TBC1D20 complexes (e.g., by detection of a detectable label(s) on the binding partners in the complex or use of antibodies that specifically bind a binding partner in the complex). Alternatively or in addition, formation of NS5A-TBC1D20 complexes can be detected in the cell cytoplasm (e.g., by detection of a detectable label(s) on the binding partners in the complex or use of antibodies that specifically bind a binding partner in the complex).

Cells used the assays can be genetically modified with expression vectors that provide for production of NS5A and/or TBC1D20 in a suitable eukaryotic cell, as described above, and may comprise genetically encodable detectable tags. In general, cell-based assays involve cells having NS5A and TBC1D20 and, optionally, at least one of Rab1 and Arf1 (depending upon the assay endpoint to be assessed). The host cell is a mammalian cell, and where HCV replication is to be assessed in parallel or in combination, the cells is a cell susceptible to HCV infection and/or which can support HCV replication (e.g., a human cell, e.g., a human cell line or primary human liver cell). The host cell can have endogenous TBC1D20, Rab1, and/or Arf1, or express an exogenous TBC1D20, Rab1, and Arf1.

In some embodiments, which can be conducted in either cell-based or cell-free assays, the effect of the agent upon GTPase activity of a Rab-GTPase (e.g., Rab1 and/or Arf1) modulated by TBC1D20 is assayed. Methods for detection of GTPase activity, are known in the art. Exemplary GTPase enzymes and methods of detecting GTPase activity are described in U.S. Pat. No. 5,965,396; U.S. Pat. No. 6,242,214; U.S. Pat. No. 6,410,267; and U.S. Pat. No. 6,509,155, each of which are incorporated herein by reference. In some embodiments, the GTPase is Rab-GTPase. The GTPase is one that can be activated by a TBC protein, e.g., a TBC1D20 polypeptide. In particular embodiments, Rab1 GTPase activity and/or Arf1 GTPase activity is used as an indicator of TBC1D20 activity, and is detected as an indicator of a level of activity of TBC1D20. As discussed in the Examples below, NS5A stimulates TBC1D20 GAP activity. Thus candidate agents that decrease such NS5A-stimulated TBC1D20 GAP activity (as assessed by assessing GAP activity and/or by assessing Rab-GTPase activity (e.g., activity of Rab1 and/or Arf1), exhibit antiviral activity.

Where antiviral activity of a candidate agent is assessed by detecting the presence or absence of an effect on expression of one or more of TBC1D20, Rab1, and Arf1, expression can be detected using any suitable method known in the art. For example, mRNA levels of one or more of TBC1D20, Rab1, and Arf1 can be assessed using primers and/or probes that provide for specific detection of such sequences. Such primers can be readily designed based on the sequences of TBC1D20, Rab1, and Arf1, which are known in the art.

For example, a target sequence for TBC1D20, Rab1, or Arf1 can be amplified from mRNA, and the presence or absence of a change in mRNA levels assessed by assessing levels of the corresponding cDNA. An amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect TBC1D20, Rab1, and/or Arf1. Generally in PCR a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324: 163; as well as in U.S. Pat. Nos. 4,683,195, 4,683,202 and 4,889,818, all incorporated herein by reference in their entireties.

PCR generally uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs-DATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

The fluorogenic 5' nuclease assay, known as the TAQMAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of the TBC1D20, Rab1, and/or Arf1 sequence can be used in TAQMAN™ analyses to detect the presence or absence of an affect of a candidate agent upon expression. Analysis is performed in conjunction with thermal cycling by monitoring the generation of fluorescence signals. The assay system dispenses with the need for gel electrophoretic analysis, and has the capability to generate quantitative data allowing the determination of target copy numbers.

Amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

Other methods of detection of expression of a target sequence that can be adapted to the screening methods described herein include, but are not necessarily limited to, hybridization protection assays (HPA) (see, e.g., See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090); nucleic acid sequence-based amplification (NASBA) (see, e.g., EP 329,822, International Patent Application No. WO 91/02814, and U.S. Pat. Nos. 6,063,603, 5,554,517 and 5,409,818, all of which are incorporated herein in their entireties); and other assays available in the art.

In general, a decrease in expression of at least one of TBC1D20, Rab1, and/or Arf1 in the presence of a candidate agent (as compared to a level of expression in the absence of the candidate agent) indicates the candidate agent has antiviral activity.

Screening methods for antiviral activity of candidate agents can also be assessed by detecting an affect of intracellular localization of TBC1D20. For example, candidate agents that affect localization of TBC1D20 with endoplasmic reticulum (ER) membranes are indicated as having antiviral activity. Such assays can be conducted by detection of detectably labeled TBC1D20 in whole cells prior to and following exposure to a candidate agent, and detecting a change in TBC1D20 localization. In one example, TBC1D20 can be detectably labeled with a first detectable label, and an ER marker (such as calnexin) can be detectably labeled with a second detectable label that emits a detectably distinct signal from that of the first detectable label. The presence or absence of a change in ER localization associated with exposure to a candidate agent can be detected by assessing colocalization of the TBC1D20 and ER marker detectable signals. A candidate agent that disrupts co-localization of the TBC1D20 and ER marker detectable signals is identified as having antiviral activity.

Variations of the above assay methods will be readily apparent upon reading the present disclosure. Assays disclosed herein can be readily adapted to assess binding between TBC1D20 and Rab1, as well as to assess binding between TBC1D20 and Arf1 in the presence or absence of a candidate agent.

Agents that Modulate Binding Between TBC1D20 and NS5A

Agents that modulate HCV replication through modulating binding TBC1D20 and NS5A can be provided in pharmaceutical formulations and administered to a subject for treatment of an appropriate condition. For example, where the agent provides for a decrease in TBC1D20 expression (e.g., by inhibiting synthesis of the TBC1D20 in the host cell), the agent has activity in reducing binding between TBC1D20 and NS5A, and reducing replication of the Flaviviridae virus in the host cell. Such agents are of interest for use in treatment of diseases caused by infection by Flaviviridae virus, such as hepatitis caused by HCV. Where the agent provides for a reduction of TBC1D20 expression, the agent has activity in reducing viral replication.

Antibodies, and functional fragments thereof, can be produced that bind TBC and/or NS5A and inhibit binding between TBC and NS5A. Methods for making and producing antibodies are well known to one of ordinary skill in the art (see Harlow et al., Using Antibodies—A Laboratory Manual, Cold Spring Harbor Lab. Press, Cold Spring Harbor, N.Y. (1999), which is incorporated by reference herein).

The inventors have identified siRNAs as exemplary agents that provide for reducing viral replication. These exemplary agents are described in more detail below, as are methods of formulation and delivery of agents of interest.

siNAs as Agents for Expression-Based Inhibition of Viral Infection

In one embodiment, inhibition of viral replication is accomplished through RNA interference (RNAi) by contacting a cell with a small nucleic acid molecule, such as a short interfering nucleic acid (siNA), a short interfering RNA (siRNA), a double-stranded RNA (dsRNA), a micro-RNA (miRNA), or a short hairpin RNA (shRNA) molecule, or modulation of expression of a small interfering RNA (siRNA) so as to provide for decreased levels of expression of TBC (e.g., TBC1D20), Rab1, and/or Arf1 (e.g., through a decrease in mRNA levels and/or a decrease in polypeptide levels).

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression, for example by mediating RNA interference "RNAi" or gene silencing in a sequence-specific manner. Design of RNAi molecules when given a target gene are routine in the art. See also US 2005/0282188 (which is incorporated herein by reference) as well as references cited therein. See, e.g., Pushparaj et al. Clin. Exp. Pharmacol. Physiol. 2006 33(5-6):504-10; Lutzelberger et al. Handbk. Exp. Pharmacol. 2006 173: 243-59; Aronin et al. Gene Ther. 2006 13(6):509-16; Xie et al. Drug Discov. Today 2006 11(1-2):67-73; Grunweller et al. Curr. Med. Chem. 2005 12(26):3143-61; and Pekaraik et al. Brain Res. Bull. 2005 68(1-2):115-20.

Methods for design and production of siRNAs to a desired target are known in the art, and their application to the TBC1D20, Rab1, and Arf1 genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., U.S. Application Pub. Nos. 2005/0282188; 2005/0239731; 2005/0234232; 2005/0176018; 2005/0059817; 2005/0020525; 2004/0192626; 2003/0073640; 2002/0150936; 2002/0142980; and 2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html) and Henschel et al. Nucleic Acids Res. 2004 32:W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Non limiting examples of target sites for design of siNA molecules for TBC1D20 and Rab1 are provided in the Examples below. Specifically, the following TBC1D20 siRNA oligonucleotides target sites were selected to knockdown endogenous expression: 5'-AAACC CUCAG CUGCA CUACU A-3' (SEQ ID NO:1), and siRNA1:5-AAGAU ACACC AGGCU CUGAA C-3' (SEQ ID NO:2). Target sites in the open reading frame of the TBC1D20, Rab1, and/or Arf1 genes can be readily identified (e.g., for TBC1D20, by analysis for the open reading frame found within the nucleotide sequence of SEQ ID NO:3, and any complementary sequences thereof). Additional target sites can be readily identified using the tools available to the ordinarily skilled artisan as discussed above.

It should be understood that the sequences provided above are the target sequences of the mRNAs encoding the target gene, and that the siRNA oligonucleotides used would comprise a sequence complementary to the target.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell* 110:563-74 and Schwarz et al., 2002, *Mol. Cell,* 10: 537-68), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules lack 2'-hydroxy (2'-OH) containing nucleotides. siNAs do not necessarily require the presence of nucleotides having a 2'-hydroxy group for mediating RNAi and as such, siNA molecules of optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules can be used to epigenetically silence a target gene at both the post-transcriptional level or the pre-transcriptional level. In a non-limiting example, epigenetic regulation of gene expression by siNA molecules can result from siNA mediated modification of chromatin structure or methylation pattern to alter gene expression (see, e.g., Verdel et al., 2004, *Science* 303:672-6; Pal-Bhadra et al., 2004, *Science* 303:669-72; Allshire, 2002, *Science* 297:1818-9; Volpe et al., 2002, *Science* 297:1833-7; Jenuwein, 2002, *Science* 297:2215-8; and Hall et al., 2002, *Science* 297:2232-7).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, e.g., two regions within TBC1D20.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., WO 92/07065; Perrault et al., 1990 *Nature* 344:565; Pieken et al., 1991, Science 253:314; Usman et al., 1992, Trends in Biochem. Sci. 17:334; WO 93/15187; and WO 91/03162; U.S. Pat. No. 5,334,711; U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, e.g., 2'-amino, 2'-C-allyl, 2'-fluoro, 2'-O-methyl, 2'-O-allyl, 2'-H, nucleotide base modifications (for a review see Usman et al., 1992, *TIBS* 17:34; Usman et al., 1994, *Nucleic Acids Symp. Ser.* 31:163; Burgin et al., 1996, *Biochem.* 35:14090). Sugar modification of nucleic acid molecules have been extensively described in the art (see WO 92/07065; Perrault et al. *Nature*, 1990, 344: 565-8; Pieken et al. *Science*, 1991, 253:314-7; Usman et al., 1992, *TIBS* 17:334-9; WO 93/15187; U.S. Pat. No. 5,334,711 and Beigelman et al., 1995, *J. Biol. Chem.*, 270:25702; WO 97/26270; U.S. Pat. No. 5,716,824; U.S. Pat. No. 5,627,053; WO 98/13526; U.S. Application Ser. No. 60/082,404, filed on Apr. 20, 1998; Karpeisky et al., 1998, *Tetrahedron Lett.*, 39:1131; Eamshaw et al., 1998, *Biopolymers* (*Nucleic Acid Sciences*) 48:39-55; Verma et al., 1998, *Ann. Rev. Biochem.* 67:99-134; and Burlina et al., 1997, *Bioorg. Med. Chem.* 5:1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, *Nucleic Acids Res.* 23:2677; Caruthers et al., 1992, *Meth. Enzymol.* 211:3-19, incorporated by reference herein. In one embodiment, nucleic acid molecules include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al., 1998, *J. Am. Chem. Soc.*, 120:8531-2). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Administration and Formulation of Agents

Formulation of an agent of interest for delivery to a subject, as well as method of delivery of agents (including siNA molecules as described above), are available in the art. These include formulations and delivery methods to effect systemic delivery of an agent, as well as formulation and delivery methods to effect local delivery of an agent (e.g., to effect to a particular organ or compartment (e.g., to effect delivery to any tissue such as breast tissue, colon tissue, liver tissue, central nervous system (CNS), etc.)). Agents (such as an siNA) can be formulated to include a delivery vehicle for administration to a subject, carriers and diluents and their salts, and/or can be present in pharmaceutically acceptable formulations.

Suitable formulations at least in part depend upon the use or the route of entry, for example parenteral, oral, or transdermal. The term "parenteral" as used herein includes percutaneous, subcutaneous, intravascular (e.g., intravenous), intramuscular, or intrathecal injection or infusion techniques and the like. Formulations include pharmaceutically acceptable salts of an agent of interest, e.g., acid addition salts.

In one embodiment, compounds (such as siNA molecules) are administered to a subject by systemic administration in a pharmaceutically acceptable composition or formulation. By "systemic administration" is meant in vivo systemic absorption or accumulation of drugs in the blood stream to facilitate distribution through the body. Systemic administration routes include, e.g., intravenous, subcutaneous, portal vein, intraperitoneal, inhalation, oral, intrapulmonary and intramuscular.

Formulations of agents can also be administered orally, topically, parenterally, by inhalation or spray, or rectally in dosage unit formulations containing pharmaceutically acceptable carriers, adjuvants and/or vehicles. Pharmaceutically acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated herein by reference. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom at least to some extent) of a disease state. The pharmaceutically effective dose depends on the type of disease, the composition used, the route of administration, the type of subject being treated, subject-dependent characteristics under consideration, concurrent medication, and other factors that those skilled in the medical arts will recognize. Generally, an amount between 0.1 mg/kg and 100 mg/kg body weight/day of active ingredients is administered.

Formulations and methods of delivery of agents (including nucleic acid molecules) to the liver are known in the art, see, e.g., Wen et al., 2004, *World J. Gastroenterol.* 10:244-9; Murao et al., 2002, *Pharm. Res.* 19:1808-14; Liu et al., 2003, *Gene Ther.* 10:180-7; Hong et al., 2003, *J. Pharm. Pharmacol.* 54; 51-8; Herrmann et al., 2004, *Arch. Virol.* 149:1611-7; and Matsuno et al., 2003, *Gene. Ther.* 10:1559-66.

Where pulmonary delivery is desired, agents (e.g., nucleic acid molecules) can be administered by, e.g., inhalation of an aerosol or spray dried formulation administered by an inhalation device (e.g., nebulizer, insufflator, metered dose inhaler, and the like), providing uptake of the agent into pulmonary tissues. Solid particulate compositions containing respirable dry particles of micronized compositions containing a compound of interest (e.g., nucleic acid) can be prepared by standard techniques. A solid particulate composition can optionally contain a dispersant which serves to facilitate the formation of an aerosol. A suitable dispersant is lactose, which can be blended with the agent in any suitable ratio, such as a 1 to 1 ratio by weight. The active ingredient typically in about 0.1 to 100 w/w of the formulation. The agent can be delivered as a suspension or solution formulation, and may involve use of a liquified propellant, e.g., a chlorofluorocarbon compound such as dichlorodifluoromethane, trichlorofluoromethane, dichlorotetrafluoroethane and mixtures thereof. Aerosol formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, e.g., US 2004/0037780, and U.S. Pat. No. 6,592,904; U.S. Pat. No. 6,582,728; U.S. Pat. No. 6,565,885, each of which are incorporated herein by reference.

Formulations and methods of delivery of agents (including nucleic acid molecules) to hematopoietic cells, including monocytes and lymphocytes, are known in the art, see, e.g., Hartmann et al., 1998, *J. Pharmacol. Exp. Ther.* 285(2):920-8; Kronenwett et al., 1998, *Blood* 91(3):852-62; Filion et al., 1997, *Biochim. Biophys. Acta.* 1329(2):345-56; Ma et al., 1996, *Leuk. Res.* 20(11/12):925-30; and Bongartz et al., 1994, *Nucleic Acids Res.* 22(22):4681-8. Such methods, as described above, include the use of free compound (e.g., oligonucleotide), cationic lipid formulations, liposome formulations including pH sensitive liposomes and immunoliposomes, and bioconjugates including oligonucleotides conjugated to fusogenic peptides, for delivery of compounds into hematopoietic cells.

Formulations and methods of delivery of agents (including nucleic acid molecules) to the skin or mucosa are known in the art. Such delivery systems include, e.g., aqueous and nonaqueous gels, creams, multiple emulsions, microemulsions, liposomes, ointments, aqueous and nonaqueous solutions, lotions, patches, suppositories, and tablets, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Oral administration can be accomplished using pharmaceutical compositions containing an agent of interest (e.g., an siNA) formulated as tablets, lozenges, aqueous or oily suspensions, dispersible powders or granules, emulsion, hard or soft capsules, or syrups or elixirs. Such oral compositions can contain one or more such sweetening agents, flavoring agents, coloring agents or preservative agents in order to provide pharmaceutically elegant and palatable preparations. Tablets, which can be coated or uncoated, can be formulated to contain the active ingredient in admixture with non-toxic pharmaceutically acceptable excipients, e.g., inert diluents; such as calcium carbonate, sodium carbonate, lactose, calcium phosphate or sodium phosphate; granulating and disintegrating agents, for example, corn starch, or alginic acid; binding agents, e.g., starch, gelatin or acacia; and lubricating agents, for example magnesium stearate, stearic acid or talc. Where a coating is used, the coating delay disintegration and absorption in the gastrointestinal tract and thereby provide a sustained action over a longer period.

Where the formulation is an aqueous suspension, such can contain the active agent in a mixture with a suitable excipient(s). Such excipients can be, as appropriate, suspending agents (e.g., sodium carboxymethylcellulose, methylcellulose, hydropropyl-methylcellulose, sodium alginate, polyvinylpyrrolidone, gum tragacanth and gum acacia); dispersing or wetting agents; preservatives; coloring agents; and/or flavoring agents.

Suppositories, e.g., for rectal administration of agents, can be prepared by mixing the agent with a suitable non-irritating excipient that is solid at ordinary temperatures but liquid at the rectal temperature and will therefore melt in the rectum to release the drug. Such materials include cocoa butter and polyethylene glycols.

Dosage levels can be readily determined by the ordinarily skilled clinician, and can be modified as required, e.g., as required to modify a subject's response to therapy. In general dosage levels are on the order of from about 0.1 mg to about 140 mg per kilogram of body weight per day. The amount of active ingredient that can be combined with the carrier materials to produce a single dosage form varies depending upon the host treated and the particular mode of administration. Dosage unit forms generally contain between from about 1 mg to about 500 mg of an active ingredient.

The agents (including siNAs) can be administered to a subject in combination with other therapeutic compounds, e.g., so as to increase the overall therapeutic effect. For example, in the context of hepatitis therapy, it may be beneficial to administer the agent with another chemotherapy regimen (e.g., antibody-based therapy) and/or with agents that diminish undesirable side-effects. Examples of chemotherapeutic agents for use in combination therapy include, but are not limited to interferon and/or ribavarin.

Of particular interest are agents that a siNAs, as described above. Exemplary formulations and methods for the delivery of nucleic acid molecules are known in the art. For example, nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see, e.g., Gonzalez et al., 1999, $Bioconjugate\ Chem.$ 10: 1068-74; WO 03/47518 and WO 03/46185), poly(lactic-co-glycolic)acid (PLGA) and PLCA microspheres (see, e.g., U.S. Pat. No. 6,447,796 and US 2002/130430), biodegradable nanocapsules, and bioadhesive microspheres, or by proteinaceous vectors (WO 00/53722). In another embodiment, the nucleic acid molecules can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules are formulated as described in US 2003/0077829, incorporated by reference herein in its entirety.

In one embodiment, a siNA molecule is complexed with membrane disruptive agents such as those described in US 2001/0007666, incorporated by reference herein in its entirety. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety. In one embodiment, a siNA molecule is complexed with delivery systems as described in US 2003/077829, WO 00/03683 and WO 02/087541, each incorporated herein by reference.

Alternatively, certain siNA molecules can be expressed within cells from eukaryotic promoters (e.g., Izant et al., 1985, $Science$ 229:345; McGarry et al., 1986, $Proc.\ Natl.\ Acad.\ Sci.\ USA$ 83:399; Scanlon et al., 1991, $Proc.\ Natl.\ Acad.\ Sci.\ USA$ 88:10591-5; Kashani-Sabet et al., 1992, $Antisense\ Res.\ Dev.$ 2:3-15; Dropulic et al., 1992, $J.\ Virol.$ 66:1432-41; Weerasinghe et al., 1991, $J.\ Virol.$ 65: 5531-4; Ojwang et al., 1992, $Proc.\ Natl.\ Acad.\ Sci.\ USA$ 89:10802-6; Chen et al., 1992, $Nucleic\ Acids\ Res.$ 20:4581-9; Sarver et al., 1990 $Science$ 247:1222-5; Thompson et al., 1995, $Nucleic\ Acids\ Res.$ 23:2259; Good et al., 1997, $Gene\ Therapy$ 4:45. Those skilled in the art realize that any nucleic acid can be expressed in eukaryotic cells from the appropriate DNA/RNA vector. The activity of such nucleic acids can be augmented by their release from the primary transcript by an enzymatic nucleic acid (WO 93/23569; WO 94/02595; Ohkawa et al., 1992, $Nucleic\ Acids\ Symp.\ Ser.$ 27:15-6; Taira et al., 1991, $Nucleic\ Acids\ Res.$ 19:5125-30; Ventura et al., 1993, $Nucleic\ Acids\ Res.$ 21:3249-55; Chowrira et al., 1994, $J.\ Biol.\ Chem.$ 269: 25856.

Where the siNA is an RNA molecule, the siNA can be expressed from transcription units inserted into a vector. The recombinant vectors can be DNA plasmids, non-viral vectors or viral vectors. siNA expressing viral vectors can be constructed based on, but not limited to, adeno-associated virus, retrovirus, adenovirus, or alphavirus. The recombinant vectors capable of expressing the siNA molecules can be delivered as described above, and provide for transient or stable expression. For example, such vectors can include: 1) a transcription initiation region; 2) optionally, a transcription termination region; and 3) a nucleic acid sequence encoding at least one strand of an siNA molecule, wherein the sequence is operably linked to the initiation region and the termination region in a manner that allows expression and/or delivery of the siNA molecule.

Subjects Amenable to Therapy

Agents that inhibit viral replication (e.g., through inhibition of the binding of NS5A and TBC1D20, decreasing activity (e.g., by decreasing expression) of TBC1D20, Rab1, and/or Arf1) are useful in treatment of any suitable viral infection in which the virus replicates in a TBC1D20-mediated manner. Exemplary viral infections include hepatitis C.

Subjects suspected of having a Flaviviridae viral infection can be screened prior to therapy. Further, subjects receiving therapy may be tested in order to assay the activity and efficacy of the agent administered, e.g., the siNA of TBC1D20, siNA of Rab1, siNA of Arf1. Significant improvements in one or more parameters is indicative of efficacy. It is well within the skill of the ordinary healthcare worker (e.g., clinician) to adjust dosage regimen and dose amounts to provide for optimal benefit to the patient according to a variety of factors (e.g., patient-dependent factors such as the severity of the disease and the like, the compound administered, and the like). For example, HCV infection in an individual can be detected and/or monitored by the presence of HCV RNA in blood, and/or having anti-HCV antibody in their serum. Other clinical signs and symptoms that can be useful in diagnosis and/or monitoring of therapy include assessment of liver function and assessment of liver fibrosis (e.g., which may accompany chronic viral infection).

Subjects for whom the therapy described herein can be administered include individuals naïve individuals (e.g., individuals who are diagnosed with HCV infection, but who have not been previously treated for HCV, particularly those who have not previously received IFN-α-based and/or ribavirin-based therapy) and individuals who have failed prior treatment for HCV ("treatment failure" patients). Previous HCV therapy includes, for example, treatment with IFN-α monotherapy (e.g., IFN-α and/or PEGylated IFN-α) or IFN-α combination therapy, where the combination therapy may include administration of IFN-α and an antiviral agent such as ribavirin. Treatment failure patients include non-responders (i.e., individuals in whom the HCV titer was not significantly or sufficiently reduced by a previous treatment for HCV to provide a clinically significant response, e.g., a previous IFN-α monotherapy, a previous IFN-α and ribavirin combination therapy, or a previous pegylated IFN-α and ribavirin combination therapy); and relapsers (i.e., individuals who were previously treated for HCV (e.g., who received a previous IFN-α monotherapy, a previous IFN-α and ribavirin combination therapy, or a previous pegylated IFN-α and ribavirin combination therapy), in whom the HCV titer decreased to provide a clinically significant response, but in whom the decreased HCV titer was not maintained due to a subsequent increase in HCV titer).

Other subjects for whom the therapy disclosed herein is of interest include subject who are "difficult to treat" subjects due to the nature of the HCV infection. "Difficult to treat" subjects are those who 1) have high-titer HCV infection, which is normally defined as an HCV titer of at least about $10^5$, at least about $5 \times 10^5$, or at least about $10^6$ or more genome copies of HCV per milliliter of serum, 2) are infected with HCV of a genotype that is recognized in the field as being associated with treatment failure (e.g., HCV genotype 1, subtypes thereof (e.g., 1a, 1b, etc.), and quasispecies thereof or 3) both.

In particular embodiments of interest, individuals have an HCV titer of at least about $10^5$, at least about $5 \times 10^5$, or at least about $10^6$, or at least about $2 \times 10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Kits

Kits with unit doses of the subject compounds, usually in topical, oral or injectable doses, are provided. In such kits, in addition to the containers containing the unit doses will be an informational package insert describing the use and attendant benefits of the drugs in treating pathological condition of interest. Representative compounds and unit doses are those described herein above.

In one embodiment, the kit comprises components for carrying out the in vitro assays or in vivo assays described above. In other embodiments, the kit comprises a siNA formulation in a sterile vial or in a syringe, which formulation can be suitable for injection in a mammal, particularly a human.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Materials and Methods

The following materials and methods were used in Examples 1-6.

Cell Cultures. Cell monolayers of the human hepatoma cell line Huh-7 are routinely grown in complete medium consisting of equal volumes of Dulbecco's modified minimal essential medium (DMEM, Gibco) and Roswell Park Memorial Institute 1640 (RPMI1640, Gibco), supplemented with 1% L-glutamine (Gibco), 1% penicillin, 1% streptomycin and 10% fetal bovine serum (FBS). Cell lines are passaged twice weekly after treatment with 0.05% trypsin-0.02% EDTA and seeding at a dilution of 1:10.

Antibodies. A Rabbit polyclonal antibody against GFP and an anti-rabbit secondary antibody are purchased from Molecular Probes (Oregon).

Plasmids. Standard recombinant DNA technology is used to construct and purify all plasmids. All regions that are amplified by PCR are analyzed by automated DNA sequencing. Plasmid DNAs are prepared from large-scale bacterial cultures and purified by a Maxiprep kit (Marligen Biosciences). Restriction enzymes are purchased from New England Bio Labs (Massachusetts).

The plasmid Bart79I was described previously. Briefly, it is made by PCR mutagenesis of HCVrep1bBartMan/AvaII such that nucleotide 5336 is changed from a G to T resulting in a change in NS5A codon 1179 from serine to isoleucine. This mutation results in a dramatic increase in replication efficiency of the HCV subgenomic replicon.

GAL4-based yeast two-hybrid screen. A suitable GAL4-based yeast two-hybrid screen for isolating TBC1D20 is the CheckMate™ Mammalian Two-Hybrid System (Promega Corp., Madison, Wis.). The screen is performed accordingly to ther manufacturers protocol.

Immunoprecipitation of labeled NS5A-GFP. To identify the [$\gamma^{32}$P]GTPγAA-labeled NS5A-GFP, membrane preparations are incubated in 1 ml of TDB buffer (2.5% Triton X-100, 25 mM TEA-Cl, pH 8.6, 20 mM NaCl, 0.5 M EDTA and 0.2% NaN3) followed by ultracentrifugation at 100,000×g for 10 minutes. The supernatants are incubated overnight with a rabbit polyclonal antibody directed against GFP (Molecular Probes), and Protein A-Sepharose (Amersham Biosciences). Following three washes in NET buffer (150 mM NaCl, 0.5 mM EDTA and 50 mM Tris-Hcl, pH 8.0) immunoprecipitates are solubilized in sample buffer and analyzed by SDS-polyacrylamide gel electrophoresis (SDS-PAGE), and autoradiography. Nitrocellulose membranes are also subjected to western analysis with mouse anti-GFP antibodies (Roche), and horseradish peroxidase-conjugated donkey anti mouse IgG, followed by chemiluminescence (Amersham) development.

Transfection. DNA constructs are transfected into Huh-7 cells using Lipofectamine 2000 (Invitrogen, USA) according to the manufacturer's protocol.

Fluorescence microscopy. Cells expressing GFP fusion proteins are fixed in 4% formaldehyde eighteen hours post transfection and mounted using mowiol mounting media. Fluorescence images are captured using a Nikon E600 fluorescence microscope equipped with a SPOT digital camera and the Openlab (Improvision, UK) image acquisition software.

Colony formation assays. The standard replicon colony formation assay is performed as previously described (3, 6). Briefly, subconfluent Huh-7 cells are trypsinized and collected by centrifugation at 700×g for 5 minutes. The cells are then washed three times in ice-cold RNase-free PBS (Bio-Whitaker), and resuspended at $1 \times 10^7$ cells/ml in PBS. Five micrograms of in-vitro transcribed RNA are mixed with 0.4 ml of washed Huh-7 cells in a 2-mm gap cuvette (BTX) and immediately pulsed (0.68 kV, 5×99 μs) using a BTX-830 Electroporator. After 10 minutes recovery at room temperature, pulsed cells are then diluted into 10 ml pre-warmed growth medium. Cells are plated in 10 cc tissue culture dishes at different densities ($4\times10^6$, $4\times10^5$, $8\times10^4$ and $4\times10^4$, cells per dish) to permit accurate colony counting. Twenty-four hours post electroporation, the cells are supplemented with plain Huh-7 to a final density of $1\times10^6$ cells/plate. Following an additional 24 hours, the selecting drug, G418 (Invitrogen) is added to the medium to a final concentration of 1 mg/ml. Growth medium supplemented with G-418 is replaced every 4 days for 3 weeks. The plates are then washed twice with PBS, incubated in 1% crystal violet made in 20% ethanol for 5 minutes, followed by 3 washes with $H_2O$ to facilitate colony counting. The G418 transduction efficiency is calculated based on the number of G418 resistant colonies relative to the number of Huh-7 cells plated after electroporation. Results are expressed as colony forming units (number of colonies per μg transfected RNA) of each mutant relative to the wild type replicon.

Protein assays. Concentrations of purified protein and protein content in membrane preparations are determined by the Bradford dye binding procedure using a Bio-Rad (Richmond, Calif.) protein assay kit.

Example 1

NS5A Interacts with TBC1D20

Since NS5A has been implicated in membrane-associated replication of HCV, it was hypothesized that among the host cell factors that associate with NS5A may be components of host cell membrane trafficking machinery. In order to test this hypothesis, full length NS5A from genotype 1b is used as a bait to screen a human liver cDNA prey library in a GAL4-based yeast two-hybrid screen. Positive clones are isolated and sequenced. One of the clones isolated encodes a protein previously termed TBC1D20 (accession no. BC014983 (SEQ ID NO:3)). TBC1D20 derives its name because it contains a TBC Rab-GTPase-activating protein (GAP) homology domain found in all known Rab activating proteins (Pan et al., 2006, *Nature* 442:303).

The authenticity of the TBC1D20-NS5A interaction is confirmed in a variety of ways. Using a GAL4-based yeast two-hybrid analysis, the full length NS5A interacts with TBC1D20 as shown by the growth of yeast containing both protein partners on selective media. The interaction is confirmed by switching the bait and prey plasmids. Any artifactual false-positive reading due to potential self-activation of either NS5A or TBC1D20 is ruled out by co-transformation with the empty reciprocal plasmid. Transfection of each of these protein partners into yeast alone (with the empty reciprocal plasmid) or in the presence of an irrelevant bait (lamin C) serves as a negative control as they do not yield growth on the selective media. The co-transfection of lamin C and T-antigen served as a negative control while the interaction between P53 and T antigen served as a positive control (FIG. 1). This demonstrates that neither NS5A nor TBC1D20 can self-activate the system.

Figure 2:
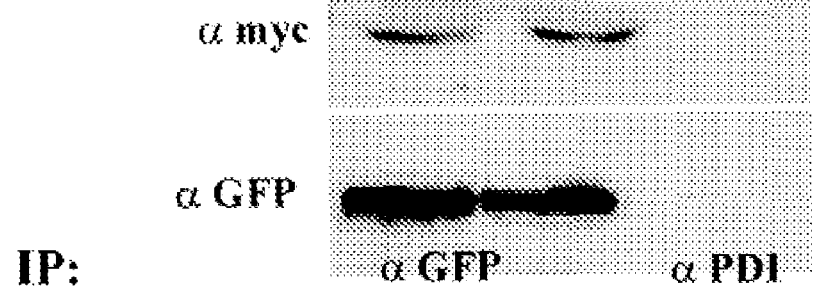
FIG. 2 depicts a western blot of immunoprecipitated (IP) wild-type GFP-NS5A (first lane) and GFP-NS5A with a mutated amphipathic helix (GFP-NS5A mAH, second lane) probed with a myc monoclonal antibody (Santa Cruz Biotechnology, sc-40) (top panel), or with an anti-GFP antibody (bottom panel). The first and second lanes are the IP using rabbit polyclonal anti-GFP antibody (Molecular Probes, A6455), and the third lane is the IP using irrelevant rabbit polyclonal anti-PDI antibody (Stressgene, SPA-890).

The TBC1D20-NS5A interaction is further confirmed using a co-immunoprecipitation assay (FIG. 2). GFP-tagged NS5A and myc-tagged TBC1D20 are both transfected into human hepatoma cells (Huh-7) and from the lysates of the transfected cells rabbit polyclonal anti-GFP antibody is used to immunoprecipitate wild-type GFP-NS5A and GFP-NS5A AmAH. NS5A has an N-terminal amphipathic helix (AH) that is necessary and sufficient for membrane localization and whose genetic disruption impairs HCV replication (Elazar et al., 2003). NS5A AmAH is mutated at the AH region. The results from the western blot indicate that TBC1D20 co-precipitates with NS5A. The ability of such a genetically-altered version of NS5A to still co-immunoprecipitate with TBC1D20 (FIG. 2) indicates that membrane association per se is not required for NS5A to interact with TBC1D20.

Example 2

TBC1D20 Interacts with the N-Terminus of NS5A

To further characterize the domains essential for this NS5A-TBC1D20 interaction, a series of deletion mutants of both NS5A and TBC1D20 are prepared. Pairs of deletion mutants are then transformed into yeast to test for possible interactions (FIG. 4). Three of the NS5A deletion mutants (A4-27, M3 237-447 and M4 237-302) are non-informative as they are able to grow on selective media without a partner plasmid. This is indicative of self-activation. Of the remaining clones, only clones containing amino acids 1-100 of NS5A enable yeast growth. A mutant with the mutated AH of FIG. 2 is also tested. This mutation does not change the NS5A-TBC1D20 interaction (FIG. 4). This confirms the immunoprecipitation result. Within TBC1D20, the interaction is mapped to the region containing amino acids 269-403 (FIG. 3).

Example 3 siRNA Reduces TBC1D20 Expression

Figure 5:
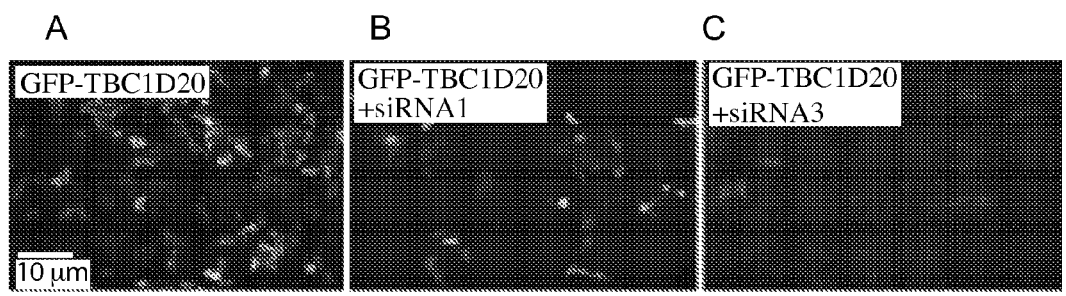
FIG. 5 depicts results for testing the effect of anti-TBC1D20 siRNA duplexes on the expression of GFP-TBC1D20. Huh-7 cells are transfected with 5 μg of GFP-TBC1D20-encoding plasmid in the absence (A panel) or presence (B and C panels) of siRNA duplexes (siRNA1 and siRNA3, respectively, each at 100 pmol) using lipofectamine 2000. Images are taken 24 hours following transfection.
Figure 6:
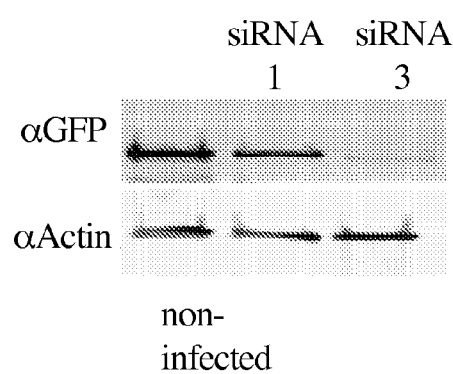
FIG. 6 depicts Western blots of the corresponding lysates probed with anti-GFP antibody or with anti-actin antibody (bottom left panel).
Figure 7:
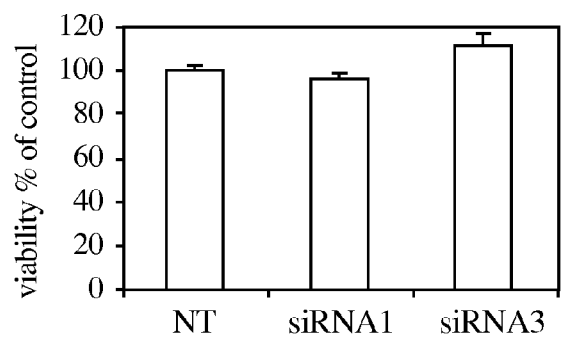
FIG. 7 depicts the effect of the siRNA transfection on cell viability tested using the Alamar blue assay (Biosource, Camarillo, Calif.). Viability is measured 24 hours following transfection of two different siRNAs duplexes (siRNA1 and siRNA3, 100 nM) using lipofectamine 2000 and compared to untreated control (NT).

To determine whether HCV replication is dependent on TBC1D20, siRNA technology is used to establish a means of inhibiting the level of TBC1D20 in cells. Two custom siRNA duplexes (siRNA3:5'-AAACCCUCAGCUGCACUACUA-3' (SEQ ID NO:1), and siRNA1:5-AAGAUACACCAGGCU-CUGAAC-3' (SEQ ID NO:2), Dharmacon, Chicago, Ill.) designed against TBC1D20 are tested for their efficacy at reducing the level of a GFP-TBC1D20 fusion protein expressed off of a plasmid transfected into the Huh-7 cell line. siRNA3 reduces most of the GFP signal compared to the non-treated control (FIG. 5, panel C vs. panel A) indicating that the siRNA does indeed efficiently knock down TBC1D20 expression. This result is verified by a Western blot of lysates from the above cells using anti-GFP antibodies (FIG. 6, compare untreated lane 1 to lane 3) and showed that siRNA1 is less efficient in reducing the GFP signal than siRNA3. Further, TBC1D20 depletion has no obvious effect on cell viability as measured by the alamar blue assay (FIG. 7).

Example 4

TBC1D20 Mediates HCV Replication

Figure 8:
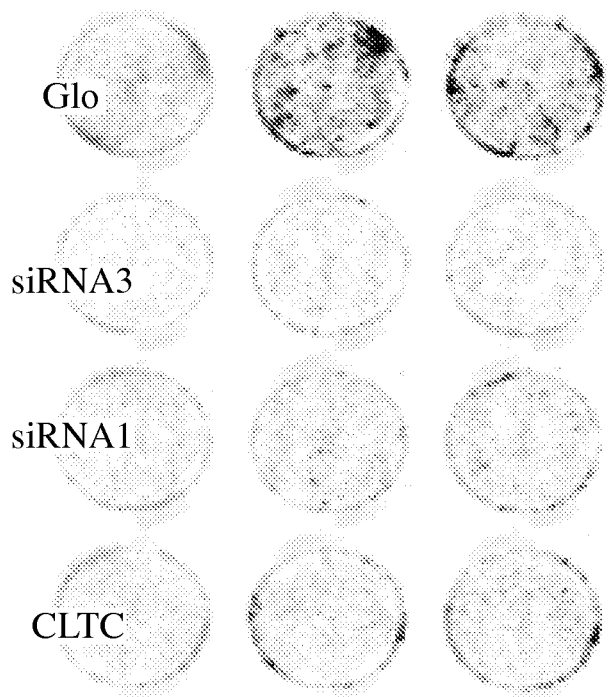
FIG. 8 depicts the results for testing the effect of TBC1D20 depletion on HCV infection. Huh-7 cells are infected with a mock inoculum (first column) or an infectious 2a inoculum (second and third columns) following prior treatment with siRNAs against TBC1D20 (middle rows), a negative control siRNA (top row), or a positive control siRNA against clathrin (bottom row). Infection and spread is monitored by in-cell western analysis using an antibody against the HCV core protein.

The dependence of HCV RNA replication on TBC1D20, is then assayed using a recently described infectious HCV clone (Lindenbach et al., 2005, *Science* 309(5734):623-6; Wakita et al. 2005, *Nature Med.*) Target cells are first treated with siRNA1 and siRNA3 to deplete endogenous TBC1D20 followed by infection with an inoculum of infectious HCV (genotype 2a, produced in vitro, as described (Tscherne et al., 2006, *J. Virol.* 80:1734-41)). After 5 days, the cells are fixed and processed using a modified in-cell Western assay (Counihan et al., 2006, *J. Virol. Meth.* 133:62) that employs a monoclonal antibody to the HCV core protein to detect infected cells. As shown in FIG. 8, siRNA3 dramatically reduces the ability of HCV to establish infection compared to cells treated with a control siRNA (compare second to top row). The inhibition is as least as potent as that due to an siRNA targeting clathrin, upon which HCV infection has been shown to depend (Blanchard et al., 2006, *J. Virol.* 80(14):6964-72). siRNA1, which is less efficient at depleting TBC1D20 expression (FIGS. 5 and 6), has a relatively less reduced level of HCV inhibition. This demonstrates that TBC1D20 is required for efficient HCV replication.

Example 5

Reducing TBC1D20 Expression Reduces HCV Replication

Figure 9:
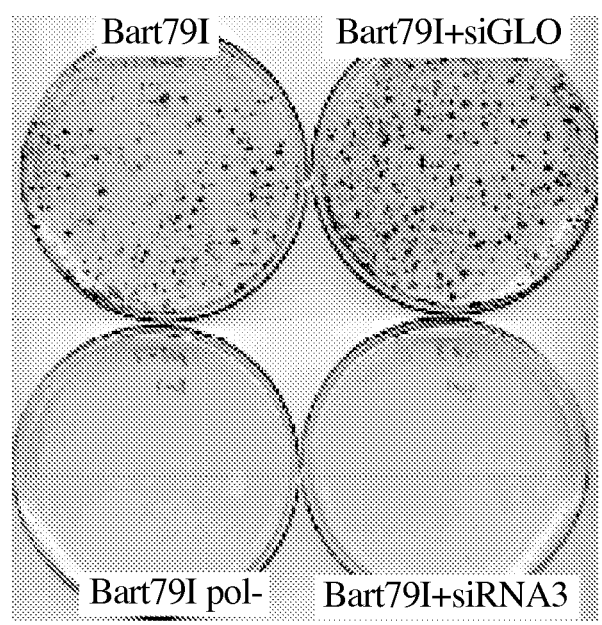
FIG. 9 depicts the results of the colony formation assay. Neomycin resistant Bart79I HCV replicons (100 ng) are co-electroporated into Huh-7 cells alone (top left), together with anti-TBC1D20 siRNA duplexes (150 nM, bottom right, siRNA3), or with siGLO (top right), a fluorescent RISC free siRNA (Dharmacon) which is used as a negative control. Bart79I with a mutated polymerase serves as another negative control (bottom left). G418 resistant colonies that supported replication are stained with crystal violet.

To further pinpoint the stage of the HCV life cycle that is dependent on TBC1D20, colony formation assays are performed using high efficiency second-generation genotype 1b HCV sub-genomic replicons, Bart 791 (Blight et al., 2000, *Science* 290:1972-4), which encodes the gene for neomycin resistance. The latter are fully competent for viral RNA genome replication, but lack the viral structural proteins and are unable to either form virus particles or infect new cells. The Bart 791 subgenomic replicons are electroporated into Huh-7 cells along with siRNA3 (FIG. 9, top left) or with siGLO (FIG. 9, top right). siGLO is a fluorescent RISC free siRNA (Dharmacon) that is serves as a negative control. Bart79I with a mutated polymerase serves as another negative control (FIG. 9, bottom left). Resulting G418-resistant colonies indicative of HCV RNA replication are stained with crystal violet. Again, HCV replication is dramatically inhibited as a result of impairing the expression of TBC1D20 (FIG. 9, bottom right). Moreover, these results identify the membrane-associated replication of the RNA genome as the target of impairment by TBC1D20 depletion, as opposed to virus assembly or entry. Because two different HCV genotypes are assayed, these results are also likely generalizable to all HCV infections.

Example 6

Colocalization of TBC1D20 and NS5A

Figure 10:
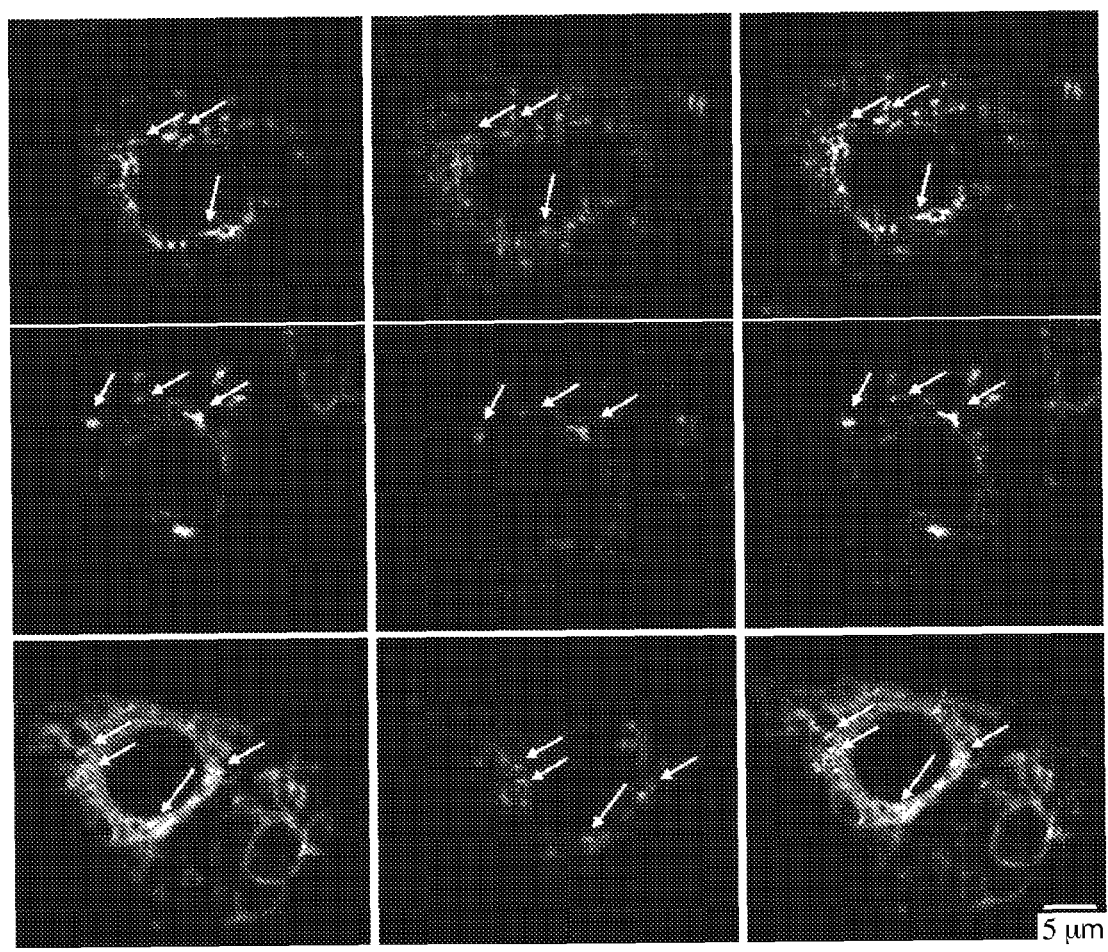
FIG. 10 depicts the confocal immunofluorescent analysis. Huh-7 cells are transfected with GFP-tagged TBC1D20 and DsRed-tagged NS5A and then subjected to confocal immunofluorescent analysis following fixation with paraformaldehyde. The white arrows indicate specific areas of colocalization.

Huh-7 cells transfected with GFP-tagged TBC1D10 and DsRed-tagged NS5A are subjected to confocal immunofluorescent analysis following fixation with paraformaldehyde. Several specific areas of colocalization are observed (FIG. 10). This provides further evidence for the binding of TBC1D20 and NS5A.

Methods and Materials

The following methods and materials were used in the Examples below.

Cell culture and transfections. Cell monolayers of the human hepatoma cell lines Huh7 and Huh7.5 (23) were routinely as described (24). Cells were passaged twice weekly after treatment with 0.05% trypsin-0.02% EDTA and seeded at a dilution of 1:10 (Huh7) or 1:3 (Huh7.5). BSC-1 cells were grown in α-MEM supplemented with 1% L-glutamine (Gibco), 1% penicillin, 1% streptomycin, 7.5% fetal bovine serum. BSC-1 cells were passaged twice weekly after treatment with 0.25% trypsin-0.02% EDTA and seeding at a dilution of 1:3. HeLa cells were grown in complete DMEM supplemented with 1% L-glutamine (Gibco), 1% penicillin, 1% streptomycin, 10% fetal bovine serum. Cells were passaged twice weekly and seeded at a dilution of 1:3.

Huh7 and Huh7.5 cells were transfected using lipofectamine 2000 (Invitrogen) according to the manufacturer. BSC-1 cells were transfected using Fugene 6 (Roche). Oligofectamine (Invitrogen) was used to transfect siRNAs into HeLa cells.

Plasmids Standard recombinant DNA technology was used to construct and purify all plasmids. All regions that were amplified by PCR were analyzed by automated DNA sequencing. Plasmid DNAs were prepared from large-scale bacterial cultures and purified by a Maxiprep kit (Marligen Biosciences). Restriction enzymes were purchased from New England Biolabs.

The plasmid pEGFP-TBC1D20 was made by cloning full length TBC1D20 (Genbank accession NM_144628) obtained from the yeast 2 hybrid positive clone into the pEGFP-Cl (Clontech). Rab constructs were described elsewhere (25). pDEST-17 for bacterial expression of TBC1D20 with a 6×HIS N-terminal tag was prepared from a Gateway system (Invitrogen) entry clone for TBC1D20 obtained from Human ORFeome Collection (Open Biosystems, OHS1771).

Bacterial Expression and purification.—Purification of Rab proteins was described in Pan et al. (2006) Nature 442 (7100):303. For the purification of TBC1D20 and TBC1D20 R66A, R105A, pDEST-17 containing both of these proteins was transformed into BL21(DE3)-Codon-Plus RIPL cells (Stratagene).

Overnight cultures of *E. coli* were diluted 1:100 in 500 ml of fresh medium and grown at 37° C. to an optical density of 1. Isopropyl-β-D-thiogalactopyranoside (IPTG; Invitrogen) was then added to a final concentration of 1 mM. After 3 h of growth, cells were pelleted and resuspended in 25 ml of lysis buffer (50 mM Tris [pH 8], 400 mM NaCl, 0.1% Fos-Choline-13 (Anatrace Inc.), 1 Protease Inhibitor Tablet (Complete Mini Protease Inhibitor Tablet, Roche)). After 15 min of incubation on ice, cells were lysed by two cycles in a French press at a pressure of 10,000 lb/in$^2$ for 1 min, followed by centrifugation at 27,000 g for 30 min at 4° C. The supernatant was then passed throw a 0.45 μm filter and loaded on HisTrap 1 ml Ni-NTA column (GE health care) in the presence of 20 mM Imidazole (Sigma). Following two washes in lysis buffer, TBC1D20 was eluted in 2 ml of elution buffer (50 mM Tris [pH 8], 400 mM NaCl, 0.1% Fos-Choline-13 and 400 mM Imidazole). The pooled eluates were loaded onto a Superdex 200 column (HiLoad Superdex 200 prep grade, 26/60; GE Health Care/Amersham Biosciences) pre-equilibrated with Superdex 200 buffer (20 mM Hepes pH 7.4, 200 mM NaCl, 1 mM MgCl$_2$). Fractions containing TBC1D20 monomer were pooled and stored at −80° C. Expression and purification were monitored by SDS-PAGE, followed by Coomassie staining or Western blot analysis with an anti-6×HIS antibody (1:5000, BD Biosciences Pharmingen). There were no differences in yield or purity between the mutant proteins and wild-type TBC1D20.

Immunofluorescence. BSC-1, Huh7, and HeLa cells were grown on coverslips. The cells were fixed 18 h posttransfection using 4% formaldehyde. For calnexin staining, cells were permeabilized with saponin, and stained with a primary anti-calnexin (1:200, StressGen). GM130 mAb was from (1:1000, Transduction Labs) and β-COP and p115 were used at 1:1000. Secondary goat anti-mouse antibodies conjugated to Alexa 594. Coverslips were mounted with polyvinyl alcohol (Mowiol) mounting medium.

Fluorescence images were captured with a Nikon E600 fluorescence microscope equipped with a SPOT digital camera and the Openlab (Improvision) image acquisition software. Confocal images were taken using a Bio-Rad confocal microscope.

GAP assays. GAP assays were conducted as previously described in Pan et al. (2006) *Nature* 442(7100), 303(25). Briefly, Rab GTPases were loaded with GTP by incubating 2-3 mg of protein with a 25-fold molar excess of GTP at 25° C. for 1 h in 20 mM HEPES pH7.5, 150 mM NaCl, 5 mM EDTA, 1 mM dithiothreitol. Free nucleotide was then removed using D-Salt columns (Pierce Biotechnology) pre-equilibrated with 20 mM HEPES pH 7.5, 150 mM NaCl. The kinetics of intrinsic and GAP-accelerated GTP hydrolysis were measured by a continuous enzyme-coupled optical assay for the release of inorganic phosphate with the use of reagents from the EnzChek Phosphate Assay Kit (Invitrogen). GTP-loaded Rab GTPases were mixed with solutions containing the assay reagents and GAPs, and dispensed into 96-well half-area microplates (Corning) using a Precision 2000 pipetting system (Bio-Tek). The final solutions contained 20 mM HEPES pH 7.5, 150 mM NaCl, 0.15 mM 2-amino-6-mercapto-7-methylpurine ribonucleoside, 0.75 U/mL purine nucleoside phosphorylase, 10 mM $MgCl_2$, 20 mM GTP-loaded Rab GTPases and various concentrations of GAPs. Absorbance at 360 nm was monitored with a Safire microplate spectrometer (Tecan).

Data were analysed by fitting them simultaneously to the pseudo-first-order Michaelis-Menten model function (Pan et al. (2006) Nature 442(7100), 303-306). The catalytic efficiency (kcat/Km) and intrinsic rate constant for GTP hydrolysis (k intr) were treated as global parameters.

Digestion of $^{35}$S-methionine labeled α1-antitrypsin with Endoglycosidase H. Huh7 cells ($6\times10^6$) were transfected with non-targeting control, TBC1D20, or Rab1 siRNAs and a plasmid expressing a non-active mutant of TBC1D20 (R66A, R105A). One million cells from each treatment were replated in 60 mm dishes 48 h after transfection. Three days posttransfection, the cells were washed twice in PBS and placed in 2.5 ml of methionine-free media. After 20 minutes, cells were pulsed with 40 μCi $^{35}$S-methionine for 10 minutes.

The cells were than washed twice with PBS and 3 ml chase media (growth media with 1 mM methionine) was added. At various time points, cells were washed twice with cold PBS and lysed with 1 ml RIPA buffer (150 mM NaCl, 50 mM Tris pH 8, 1 mM EDTA, 1% NP-40, 0.1% SDS) containing protease inhibitors (complete mini, Roche). Lysates were cleared by centrifugation at 500 g for 10 minutes at 4° C. The lysates were then incubated at 4° C. with polyclonal antibody against α1-antitrypsin (dilution 1:125) for 2 h followed by incubation with protein A-Sepharose for 30 min. Bound immune complexes were resuspended in 20 μl of resuspension buffer (0.1 M sodium acetate [pH 5.6], 0.3% SDS, 0.3 M β-mercaptoethanol) and heated at 95° C. for 6 minutes followed by a 2 minute centrifugation (14,000×g). Supernatants were collected and 20 μl of a solution containing 0.1 M NaOAc (pH 5.6), with or without Endoglycosidase H (endo H, 20 U/μl) was added to each tube. The tubes were then incubated overnight at 37° C. Samples were then heated at 95° C. for 6 min, centrifuged at 14,000×g for 2 min, and analyzed by SDS-PAGE followed by autoradiography.

siRNAs. All siRNAs were purchased from Dharmacon as duplexes. The sequences of the siRNAs designed against TBC1D20 were siRNA3: 5CCAGCAGAGGC-CUGAUAUGU U-3 (SEQ ID No. 13) antisense 5'-CAUAU-CAGGCCUCUGCUGGUU-3' (SEQ ID No. 14). Rab1A siRNA was an ON-TARGETplus SMARTpool purchased from Dharmacon (L-008283-00). siCONTROL Non-Targeting siRNA #1 (Dharmacon) was used as a negative control. siRNA transfections were done using 100 nM of siRNA per well in a 6 well plate. Sense sequences of the Rabib siRNAs 9, 10, 11, and 12 were as follows:

| duplex 9  | UGCAGGAGAGAUUGACCGCUAUU | (SEQ ID No. 15) |
| duplex 10 | ccagcgagaacgucaauaauu   | (SEQ ID NO. 16) |
| duplex 11 | cggugggaucugaguauauuu   | (SEQ ID No. 17) |
| duplex 12 | gaauaugacuaccuguuuauu   | (SEQ ID No. 18) |

Carbonate extraction of Membranes. A confluent 10 cc dish of Huh7 cells was transfected with GFP-TBC1D20. The cells were trypsinized 24 h posttransfection, washed twice with PBS supplemented with protease inhibitors and homogenized with 50 passes through a 25-gauge needle. Breakage of the cells was confirmed using trypan blue exclusion. The supernatants were cleared at 500 g, and split into two equal volumes. Membranes were then pelleted by a 30 min centrifugation at 100,000 g in a Beckman TL-100 ultracentrifuge. The supernatant was saved as the cytosolic fraction and the membranes were and resuspended in 10 volumes of 0.3M sucrose in 10 mM Tris pH 7. An additional 10 volumes containing 10 mM Tris pH 7 or 0.2M of sodium carbonate pH 11 (27) were added to the control and treated tube respectively followed by a 30 min incubation on ice. The homogenates were then spun at 100,000×g for 1 h at 4° C. Membranes were resuspended directly in sample buffer and the supernatants were precipitated using methanol-chloroform precipitation and resuspended in sample buffer. Equivalent volumes of each sample were loaded on the gel and analyzed by immunoblot with anti-GFP antibodies (molecular probes, 1:1000).

Real-time PCR. For real-time PCR experiments, Huh 7.5 cells were transfected with siCONTROL or TBC1D20 siRNA. The cells were trypsinized 24 h after transfection and $2\times10^5$ cells were plated in a 12 well plate. The cells were allowed to adhere and were infected with cell culture-grown HCV titered at TCID501.4×104/ml, as described (28,29). 3 h after infection, cells were washed twice with media. For each time point, RNA was extracted from three wells using 0.5 ml of TRIzol Reagent (Invitrogen), then subjected to reverse transcription using random hexamers and Superscript II reverse transcriptase (Invitrogen, Carlsbad, Calif.). Real-time PCR was performed on the resulting cDNA to quantify the amount of TBC1D20, HCV and actin RNA (in separate reactions) in each sample, as compared to an in vitro-transcribed HCV RNA standard and human actin standard (Applied Biosystems, Foster City, Calif.), respectively. HCV was quantified using primers AGAGCCATAGTGGTCT (SEQ ID No. 19) and CCAAATCTCCAGGCATTGAGC (SEQ ID No. 20), and probe FAMCACCGGAATTGCCAGGACGAC-CGG-TAMRA (SEQ ID No. 21). Actin was quantified using betaactin control reagents (Applied Biosystems) according to manufacturer's instructions. TBC1D20 was quantified using TaqMan Gene Expression Assays probe and primer set for TBC1D20 (Applied biosystems, Hs00299060_ml). Rab1A was quantified using TaqMan® Gene Expression Assays probe and primer set for Rab1A (Applied biosystems, Hs00366313 ml).

Example 7

TBCID20 is a RAB1 GAP

Human cells are predicted to have as many as 70 Rabs. To narrow down the number of potential substrates for the TBC1D20 GAP, the subcellular distribution of TBC1D20 was characterized. When BSC-1 cells were transfected with a plasmid expressing TBC1D20 with an N-terminal GFP tag, a reticular pattern typical of ER localization was observed (data not shown).

Confocal microscopy showed that in all the TBC1D20 expressing cells most of the TBC1D20 signal co-localized with the ER marker calnexin, confirming its ER localization. Based on this apparent ER-localization, we predicted that the Rab(s) regulated by TBC1D20 are likely to be those associated with the ER. Since some Rabs are known to be activated by more then one GAP, a broader screen including 27 mammalian Rabs was performed. In addition, that ability of TBC1D20 to activating several different ARFs was tested. Arfs, which like Rabs also regulate vesicular trafficking, can sometimes be regulated by Rab GAPs.

Figure 14:
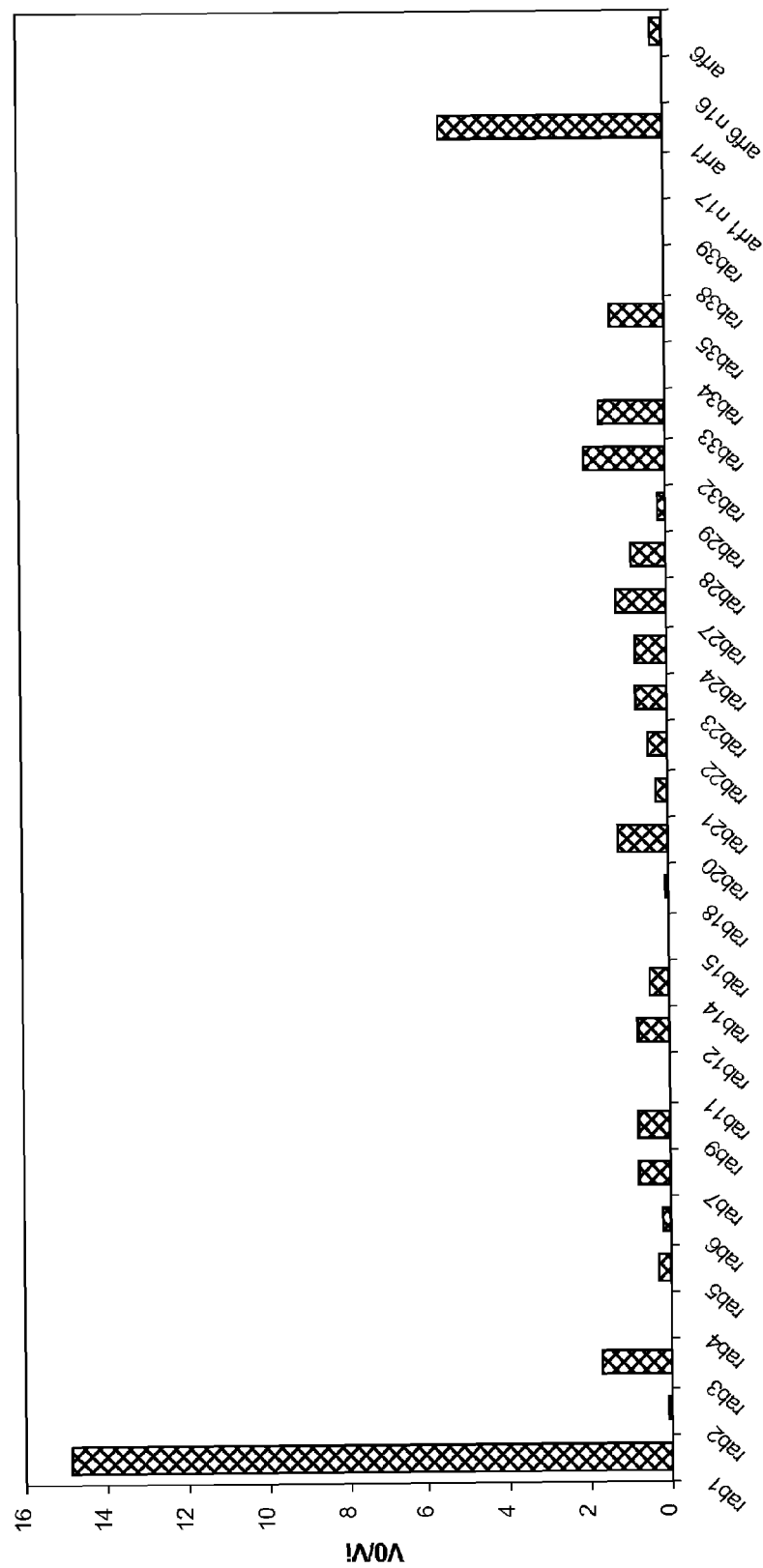
FIG. 14 is graph showing the results of assay to determine the ability of TBC1D20 to activate a panel of Rabs and Arfs. Catalytic efficiency (Km/kcat) relative to the intrinsic rate constant for GTP hydrolysis was determined. Values represent the mean and s.d. from duplicate wells. Note that only Rab1 displays significant activation by TBC1D20.

Among the Rabs tested, TBC1D20 had a high selectivity for activating the Rab1 GTPase (FIG. 14). In addition, TBC1D20 facilitated activation of Arf1, suggesting that TBC1D20-Arf1 interaction may also be involved in facilitated viral replication of HCV.

Figure 15:
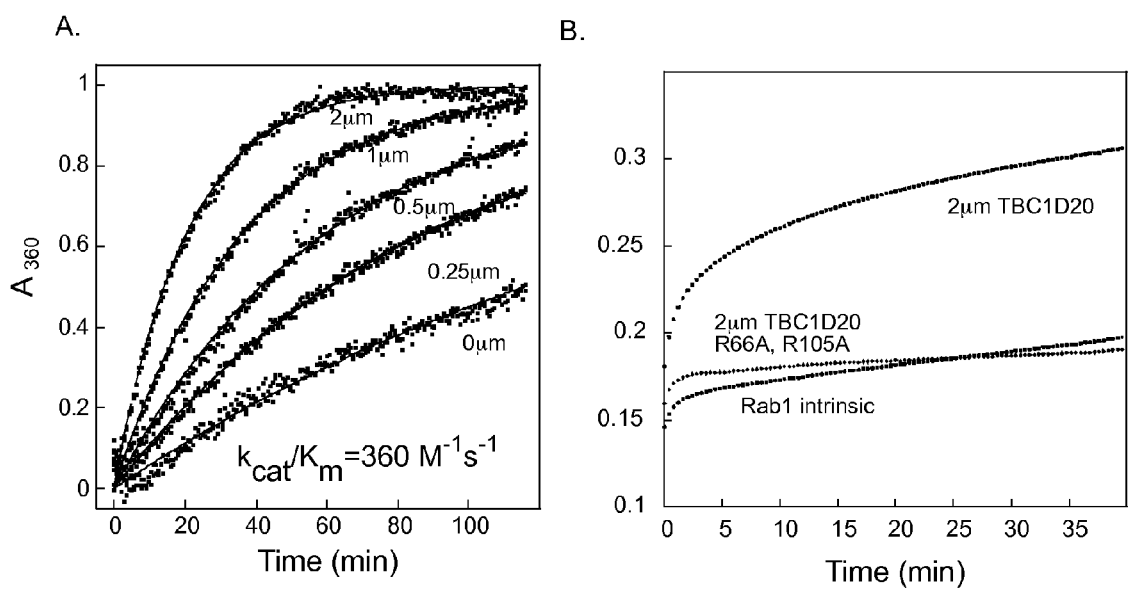
FIG. 15 is a set of graphs showing that: (Panel A) GTP hydrolysis for Rab1 in the presence of increasing concentrations of TBC1D20 (solid lines represent a simultaneously fitted pseudo-first-order Michaelis-Menten model function from which catalytic efficiency values were extracted; and (Panel B) Kinetics of GTP hydrolysis for Rab1 in the presence of wild type or TBC domain mutant forms of TBC1D20.

TBC1D20's activity was further investigated by simultaneous fitting of the data to a pseudo-first-order Michaelis-Menten model function. Activation of Rab1GTP hydrolysis by TBC1D20 has an apparent catalytic efficiency (kcat/Km) of 360 $M^{-1}s^{-1}$ (FIG. 15, Panel A). A recent crystallographic study revealed that TBC domain Rab-GAPs accelerate the GTPase activity of their corresponding GAP TBC domain indicate that Rab-GAPs activate their Rab GTPase substrates via a so-called "dual finger" mechanism involving two critical catalytic residues supplied in trans by the TBC domain (Pan et al. (2006) Nature 442(7100), 303). Two point mutations were introduced into the TBC domain of TBC1D20 designed to disrupt one of the above "fingers," and the ability of the resulting mutant TBC1D20 (R66A, R105A) to activate Rab1 GTPase activity was tested. As shown in FIG. 15, Panel B, the GTPase activating activity of TBC1D20 on Rab1 was abolished when these conserved arginine residues were mutated to alanine. These mutant TBC1D20 s could thus serve as negative controls in screening assays to assess the effect of a candidate compound upon TBC1D20-mediated GTPase activity.xxx Example 8

TBC1D20 Depletion Affects ER—to Golgi Transport

Given that Rab1 is essential for ER-to-Golgi vesicle trafficking, we next examined the effect of TBC1D20 knockdown on this pathway. For this purpose, the accumulation of Golgi-specific forms of α1-antitrypsin in cells previously treated with TBC1D20 siRNAs was examined. α1-antitrypsin is the major circulating serine protease inhibitor secreted by hepatocytes into the serum. The transport of α1-antitrypsin from the ER to the Golgi results in processing of the high mannose, endoglycosidase H (Endo H)-sensitive oligosaccharides found in the ER to a complex, Endo H-resistant form present in the Golgi and plasma membrane.

Post-siRNA transfection (72 h), the cells were pulsed with $^{35}$S-methionine for 15 min followed by a chase period with cold methionine. The cells were lysed at different time points during the chase period and α1-antitrypsin was immunopercipited. The immunoprecipitates were digested with Endo H and detected using SDS-PAGE and autoradiography. In addition to transfection with anti-TBC1D20 siRNAs, parallel cultures of Huh7 cells were transfected with a non-targeting siRNA control (siControl), Rab1A siRNAs, or a plasmid expressing a non-active mutant of TBC1D20 (R66A, R105A). At time zero in control cells, all of the α1-antitrypsin was found to be sensitive to EndoH cleavage (FIG. 16, Panel A, lanes 1 and 2 at left). The upper band (asterisk) is a background band that was present in the immunoprecipitates. In the next reactions shown, we analyzed only EndoH-cleaved products at various times of chase. Thus, higher molecular weight forms detected represent those bearing complex oligosaccharides. In control siRNA treated cells, α1-antitrypsin was converted to a higher molecular weight, complex oligosaccharide-containing form that was readily detected at 60 minutes of chase ("Golgi"). Compared with the amount of radiolabel detected as the ER form at time zero, 70% of the protein was converted to the Golgi form (FIG. 16, Panels A, B). In contrast, Rab1A depletion blocked generation of the Golgi form by 90% (FIG. 16, Panel A, far right; FIG. 16, Panel B).

siRNA directed against TBC1D20 only partially inhibited (60%) the generation of the Golgi form of α1-antitrypsin. Mutant TBC1D20 (R66A, R105A) was more efficient in inhibiting this pathway (80%) than the TBC1D20 siRNAs. These results thus provide functional data to complement the biochemical assays of FIG. 16 in support of a role for TBC1D20 in regulating Rab1-mediated ER to Golgi transport.

Since Rab1 mutants affect the structural integrity of the Golgi the morphology of the Golgi complex after TBC1D20 depletion was examined. HeLa cells were co-transfected with a "RISC free" green fluorescent siRNA together with either siControl or siRNA against TBC1D20. Cells that had taken up the siRNA mixtures were identified by their green fluorescent staining. No apparent changes in Golgi morphology were detected under these conditions as monitored by the distribution of known Rab1 effectors (GM130 and p115) and a protein known to be modulated by Rab1 activity (β-COP) (data not shown).

Example 9

TBC1D20 is a Transmembrane Protein

Hydropathy analysis of TBC1D20's primary sequence using the SOSUI prediction system (Hirokawa et al. (1998) Bioinformatics 14(4), 378-379) revealed a C-terminal hydrophobic domain of 26 residues (FIG. 17, Panels A and B). The latter represents a transmembrane domain within TBC1D20. Experimental support for this analysis came during its purification. The amount of protein purified was extremely low without the presence of a detergent. Alkaline stripping was used to further confirm that TBC1D20 associates with membranes in a manner characteristic of integral membrane proteins. For this, Huh7 cells expressing GFP-TBC1D20 were homogenized and lysates were separated into cytosol and membrane fractions by centrifugation. Membranes were then washed with either sodium carbonate or buffer, and incubated on ice for 30 min. Membranes were pelleted by centrifugation and analyzed by SDS-PAGE and immunobloting. The GFP-tagged TBC1D20 was found exclusively in the membrane fraction and was resistant to alkaline extraction (FIG. 17, Panel C), consistent with the notion that it is an integral membrane protein.

Example 10

Depletion oF RAB1 Inhibits Accumulation of HCV RNA

TBC1D20 depletion inhibits HCV RNA accumulation. If TBC1D20 is indeed a Rab1-GAP, the effect of Rab1 depletion on viral RNA accumulation should be similar or greater. To test this prediction, treated Huh7.5 cells were treated with control, TBC1D20, or Rab1A siRNAs, followed by infection with an inoculum of infectious HCV (genotype 2a, produced in vitro, as described (Lindenbach et al. (2005) Science 309 (5734), 623-626)).

The efficiency of these siRNAs in knocking down endogenous TBC1D20 and Rab1A RNA levels was determined (FIG. 7A). Endogenous TBC1D20 RNA levels were significantly reduced (60%) within 48 hours of siRNA transfection. Inhibition decreased to 20% at 120 h due to the transient nature of the siRNA transfection. Rab1A inhibition reached similar levels after 48 h (60%) but stayed stable throughout the experiment.

Figure 18:
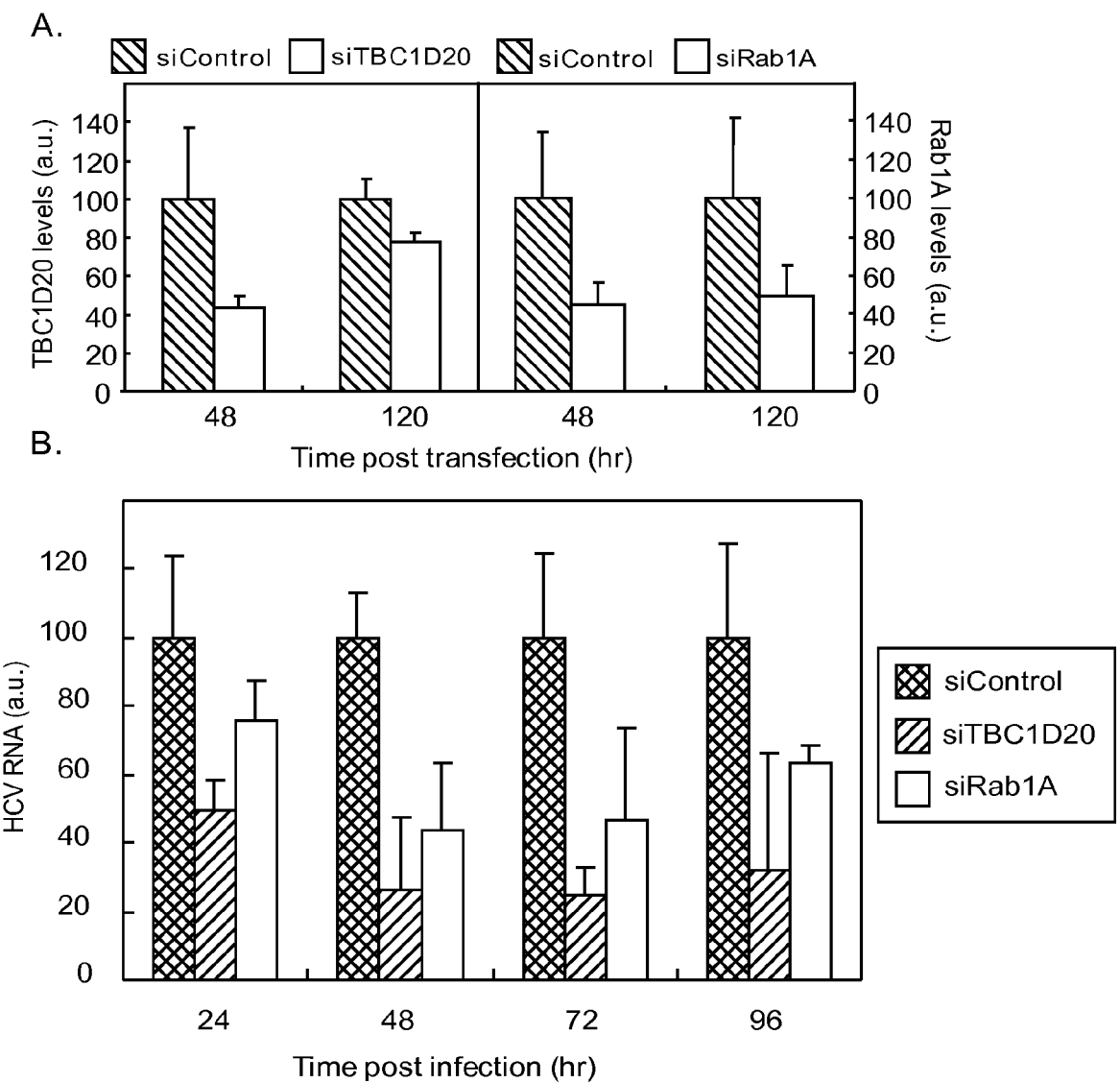
FIG. 18 is a set of graphs illustrating that Rab1 depletion reduces HCV RNA levels. Huh7.5 cells were transfected with either TBC1D20 and Rab1A targeting siRNAs, or a control non-targeting siRNA. After transfections (24 h), cells were trypsinized and plated in 12 wells plates. The cells were allowed to adhere and were infected with tissue culture grown HCV. Total cellular RNA was harvested every 24 h followed by real-time PCR assays. Panel A. Endogenous TBC1D20 or Rab1A levels detected 48 and 120 hr after transfection to assess the knockdown efficiency of the respective siRNAs. Panel B. Following infection, HCV RNA levels were detected every 24 h by quantitative real-time PCR. Values (mean±SD) from three independent wells are shown. Results were normalized to actin RNA levels.

RNA from the same samples was then assayed for HCV RNA levels (FIG. 18, Panel B). Viral RNA levels in TBC1D20 siRNA treated cells was reduced by 50% 24 h after infection compared to the control, reaching a maximum inhibition level of 80% after 48 h. The extent of HCV inhibition as a result of TBC1D20 depletion was equal to or greater than that observed with inhibition of other host targets reported to play a role in HCV replication (Xue et al. (2007) Archives of virology 152(5), 955; Stone et al. (2007) J. Virol., JVI.01366-01306). In Rab1A depleted cells, viral RNA levels were reduced by 25% 24 h after infection, reaching a maximum inhibition level of 60% after 48 h. This effect was not seen in the cells transfected with the control siRNA, consistent with a role for TBC1D20 and Rab1 in HCV RNA production.

The effects of Rab1b depletion on HCV replication and on cell viability was assessed using different siRNA. Huh7.5 cells were transfected with four different Rab1b targeting siRNAs (referred to as 9-12), or a control non-targeting siRNA. After transfections cells were trypsinized and plated in 12 wells plates. The cells were allowed to adhere and were infected with tissue culture grown HCV. Total cellular RNA was harvested after 24 h followed by real-time PCR assays.

To assess the effects on HCV replication, following infection, HCV RNA levels were detected after 72 h by quantitative real-time PCR. Cell viability was assessed using Alamar blue assays at 72 h following transfection of anti-rab1b or control (siCt) siRNAs. Values (mean±SD) from three independent wells were determined, and results normalized to actin RNA levels.

Figure 19:
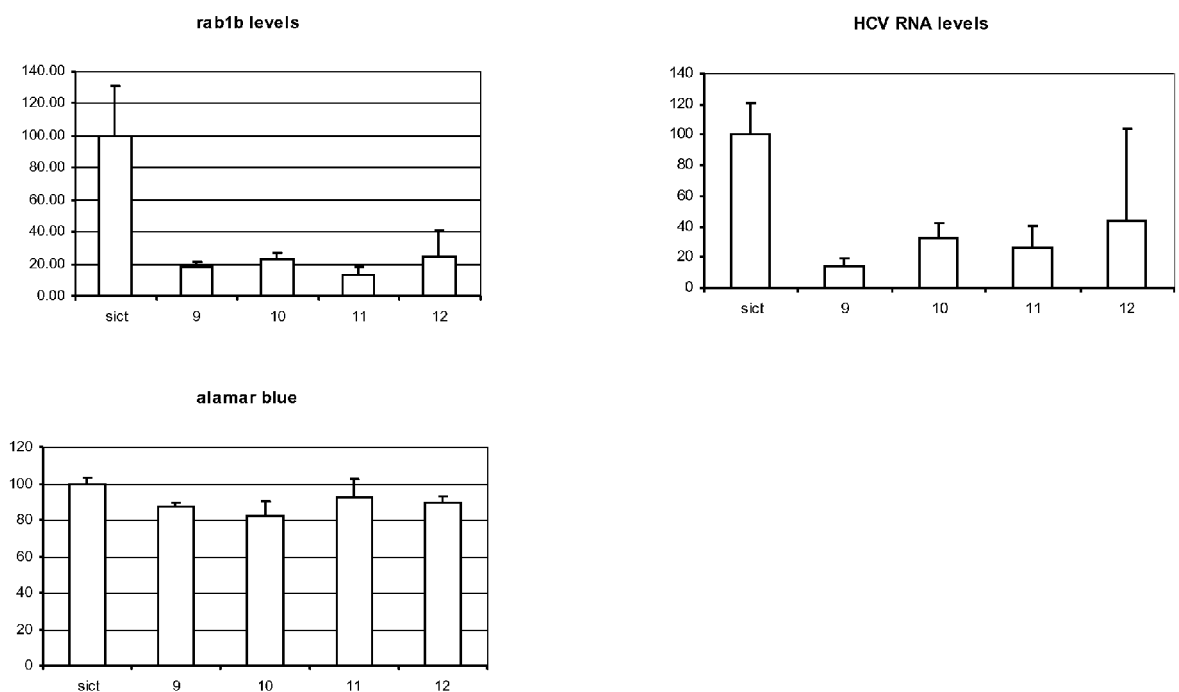
FIG. 19 is a set of graphs showing the effects of four Rab1b siRNAs on rab1b levels (Panel A), HCV RNA levels (Panel B), and cell viability (as assessed by Alamar blue assay).

As shown in FIG. 19, Panel A, as expected endogenous Rab1b levels were decreased by all four Rab1b siRNAs, but not by control at 72 after transfection. As shown in FIG. 19, Panel B shows that each of the 4 test siRNAs to Rab1b decreased HCV replication as assessed by RNA levels. However, as shown in FIG. 19, Panel C, none of the siRNAs substantially affected cell viability, indicating that Rab1b can serve as an anti-viral target while reducing the likelihood of cell toxicity. Stated differently, down-regulation of Rab1b activity (e.g., by decreasing Rab1b expression) does not affect cell viability, but yet can inhibit HCV replication.

Example 11

NS5A Mediates Stimulation of TBC1D20 RAB GAP Activity

The effect of NS5A on the catalytic activity of TBC1D20 was assessed in the presence of increasing concentrations of rab1b in the presence of TBC1D20 alone, TBC1D20 with 0.5 µM NS5a, or TBC1D20 with 1 µM NS5A. Velocities were measured as a function of the concentration of Rab1. The data was analyzed by fitting to the Michaelis-Menten model function.

Figure 20:
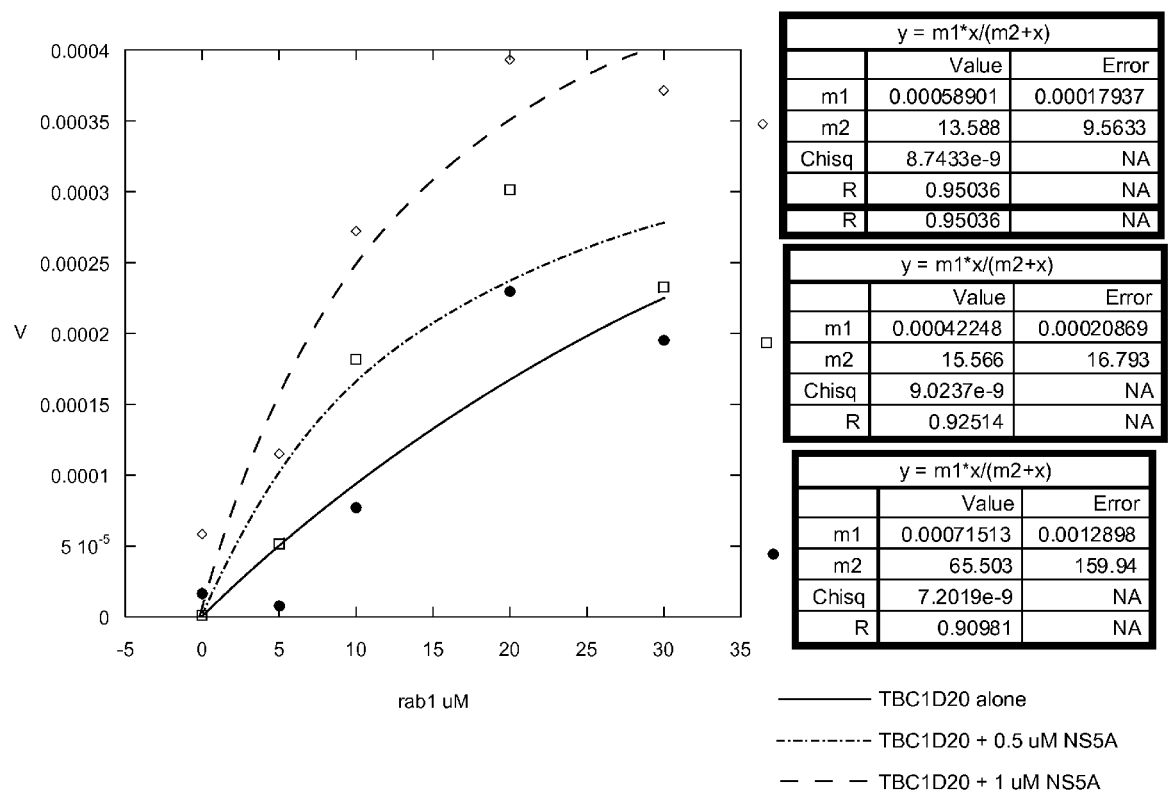
FIG. 20 is a graph and set of tables showing the effect of NS5A on the catalytic activity of TBC1D20. Velocities were measured as a function of the concentration of Rab1 in presence (0.5 μM or 1 μM) or absence (TBC1D20 alone) of NS5A. The data was analyzed by fitting to the Michaelis-Menten model function.

The data are shown in FIG. 20. These data demonstrate that not only do TBC1D20 and NS5A interact, NS5A actually serves to enhance rab GAP activity of TBC1D20. Thus, decreasing elevated rab GAP activity of TBC1D20 can serve as the basis for screening candidate agents for anti-HCV activity. Stated differently, an agent need not necessarily completely inhibit TBC1D20 activity, or rab1 activity, in order to provide an antiviral effect against HCV.

A novel cellular binding partner of NS5A, TBC1D20, has been identified and isolated using a yeast two-hybrid screen. TBC1D20 interacts with the N-terminal segment of NS5A. This is the first demonstration of interaction between a Rab-GTPase-activating protein family member and a viral protein. This highlights a novel mechanism whereby viruses may subvert host cell membrane trafficking machinery. In the case of HCV, replication occurs on a specialized membrane structure triggered by the virus within the host cell cytoplasm. These results indicate a new model whereby the establishment of this membranous replication platform is mediated by the hijacking of TBC1D20 and the Rab-GTPase(s) under the control of NS5A. Finally, since inhibition of TBC1D20 severely impairs HCV RNA replication with no obvious effect on cell viability, pharmacologic disruption of TBC1D20, or its interaction with NS5A, is a potential antiviral strategy.

These results reveal that inhibition of TBC1D20 and NS5A interaction represents an attractive new target for anti-HCV therapy. Inhibitors can be readily screened for their capability to reduce TBC1D20 and NS5A interaction, decrease TBC1D20 activity in enhanced GTPase activity of Rab1, and/or decrease Rab1 activity (e.g., by inhibition of expression).

It is evident from the above results and discussion that the present disclosure provides an important new tool for discovery of anti-HCV agents. In particular, the disclosure provides systems for identifying anti-HCV agents based on their ability to inhibit binding of TBC1D20 and HCV-encoded NS5A protein. As such, the methods and systems disclosed herein find use in a variety of different applications, including research, medical, therapeutic and other applications.

What is claimed is:

1. A method of screening a test agent for activity in modulating the replication of a Flaviviridae virus, the method comprising:

contacting a test agent with a NS5A polypeptide, a TBC1D20 polypeptide, and, optionally, a Rab1 polypeptide and/or an Arf1 polypeptide, said contacting being under conditions suitable for TBC1D20 to activate a GTPase; and detecting the presence or absence of a change in an activity of at least one of the TBC1D2 polypeptide, the Rab1 polypeptide, and the Arf1 polypeptide;

wherein the presence in a change in activity of at least one of the TBC1D20 polypeptide, the Rab1 polypeptide, and the Arf1 polypeptide indicates the test agent has activity as an antiviral agent.

2. The method of claim 1, wherein said detecting step comprises detecting an effect of the test agent on binding between the TBC1D20 polypeptide and the NS5A polypeptide.

3. The method of claim 2, wherein said activity is Rab-GTPase activity of TBC1D20.

4. The method of claim 1, wherein said activity is GTPase activity of the Rab1 polypeptide and/or the Arf1 polypeptide.

5. The method of claim 1, wherein said TBC1D20 polypeptide or said NS5A polypeptide is attached to a detectable label, and said detecting step comprises detecting said detectable label.

6. The method of claim 1, wherein said Flaviviridae virus is hepatitis C virus (HCV).

7. A method of screening a test agent for activity as an antiviral agent against a Flavivirdae virus, the method comprising:
   contacting a test agent with a cell expressing NS5A and at least one of a TBC1D20 polypeptide, a Rab1 polypeptide, and an Arf1 polypeptide, said contacting being under conditions suitable for TBC1D20 to activate a GTPase; and
   detecting the presence or absence of a change in an activity of at least one of the TBC1D20 polypeptide, the Rab1 polypeptide, and the Arf1 polypeptide;
   wherein the presence in a change in activity of at least one of the TBC1D20 polypeptide, the Rab1 polypeptide, and the Arf1 polypeptide indicates the test agent has activity as an antiviral agent against a Flavivirdae virus.

8. The method of claim 7, wherein said detecting step comprises detecting an effect of the test agent on binding of TBC1D20 polypeptide to NS5A polypeptide.

9. The method of claim 7, wherein said detecting step comprises detecting an effect of the test agent on an activity of TBC1D20 polypeptide.

10. The method of claim 9, wherein said activity is activation of a GTPase.

11. The method of claim 10, wherein the GTPase is Rab1.

12. The method of claim 7, wherein said detecting is by assessing expression of TBC1D20, Rab1, and/or Arf1.

13. The method of claim 7, wherein said detecting is by assessing a change in activity of TBC1D20 as detected by reduction in co-localization of TBC1D20 with endoplasmic reticulum (ER).

14. The method of claim 7, wherein the method further comprises screening said agent for activity in reducing replication of a Flaviviridae virus in said cell-based assay.

15. A method of screening a test agent for activity as an antiviral agent against Hepatitis C virus, the method comprising:
   contacting an expression system expressing a NS5A polypeptide and a TBC1D20 polypeptide, and, optionally, a Rab1 polypeptide expression system with a test agent;
   detecting the presence or absence of a change in expression of the TBC1D20 polypeptide and/or the Rab1 polypeptide;
   wherein the presence of a change in expression of the TBC1D20 polypeptide or the Rab1 polypeptide in the presence of the test agent relative to a level of expression of the TBC1D20 polypeptide or the Rab1 polypeptide in the absence of a test agent indicates the test agent has activity in modulating expression of TBC1D20 or Rab1 expression, which is indicative of antiviral activity against hepatitis C virus.

\* \* \* \* \*

SEQUENCE LISTING

<160> NUMBER OF SEQ ID NOS: 21

<210> SEQ ID NO 1
<211> LENGTH: 21
<212> TYPE: RNA
<213> ORGANISM: Artificial Sequence
<220> FEATURE:

<223> OTHER INFORMATION: siRNA

<400> SEQUENCE: 1
aaacccucag cugcacuacu a                                              21

<210> SEQ ID NO 2
<211> LENGTH: 21
<212> TYPE: RNA
<213> ORGANISM: Artificial Sequence
<220> FEATURE:
<223> OTHER INFORMATION: SiRNA

<400> SEQUENCE: 2
aagauacacc aggcucugaa c                                              21

<210> SEQ ID NO 3
<211> LENGTH: 2020
<212> TYPE: DNA
<213> ORGANISM: Human

<400> SEQUENCE: 3

```
ccgatgccga gcgggtgcta cgtcccgcgg tcggagccgc gtcttctccc ggctccgcca      60
ccagccgggg ctcgggtggg ggcccggggc cccggggcat ggccctccgg agtgcgcagg     120
gcgacggccc cacctccggc cactgggacg gcggcgcgga gaaggcagac tttaacgcca     180
aaaggaaaaa gaaagtggca gagatacacc aggctctgaa cagtgatccc actgatgtgg     240
ctgcccttag acgcatggct atcagtgaag gagggtcct gactgatgag atcagacgaa     300
aagtgtggcc caagctcctc aatgtcaatg ccaatgaccc acctcctata tcagggaaga     360
acctacggca gatgagcaag gactaccaac aagtgttgct ggacgtccgg cggtcattgc     420
ggcggttccc tcctggcatg ccagaggaac agagagaagg gctccaggaa gaactgattg     480
acatcatcct cctcatcttg gagcgcaacc ctcagctgca ctactaccag ggctaccatg     540
acattgtggt cacatttctg ctggtggtag gcgagaggct ggcaacatcc ctggtagaaa     600
aattatctac ccaccacctc agggatttta tggatccaac aatggacaac accaagcata     660
tattaaacta tctgatgccc atcattgacc aggtgaatcc agagctccat gacttcatgc     720
agagtgctga ggtagggacc atcttttgccc tcagctggct catcacctgg tttgggcatg     780
tcctgtctga cttcaggcac gtcgtgcggt tatatgactt cttcctggcc tgccacccac     840
tgatgccgat ttactttgca gccgtgattg tgttgtatcg cgagcaggaa gtcctggact     900
gtgactgtga catggcctcg gtccaccacc tgttgtccca gatccctcag gacttgccct     960
atgagacact gatcagcaga gcaggagacc tttttgttca gtttccccca tccgaacttg    1020
ctcgggaggc cgctgcccaa cagcaagctg agaggacggc agcctctact ttcaaagact    1080
ttgagctggc atcagcccag cagaggcctg atatggtgct gcggcagcgg tttcggggac    1140
ttctgcggcc tgaagatcga acaaaagatg tcctgaccaa gccaaggacc aaccgctttg    1200
tgaaattggc agtgatgggg ctgacagtgg cacttggagc ggctgcactg gctgtggtga    1260
aaagtgccct ggaatgggcc cctaagtttc agctgcagct gtttccctga agccagaga    1320
agaccttcct cttacatcac attaaggcac ccactcacta ccttggcgtc gttttttggg    1380
tctgacttga ctcgtcaact gctggtctct cccacctggt tggaaatgtc gttgaaact    1440
tgcaaagact ctccagacct tagggaacaa gaggcatcac tcagtccttc tgggacagct    1500
tccctgcctc agaaaacgga atctctgtct gtgaccttct cctgccccat ttcacttgct    1560
caacaccaga cttttaatctg actgtagctc ataagaccct cattccagag agggtgctgc    1620
```

```
cccatacccg gaaggaggaa cgctgcacag agaggccaag aagcatctgg acagacaggc      1680
cttgctgggt ttagacctta tgcttttgt ccagtttcat ctcaacacag ctgccatgct       1740
tcagccatgc ctatccaatg acgtctccat aaaaggccca ggaacacggg agcttctgaa      1800
gagctgaaca tgtggaggga ggggaacgag aacttgtcca tgtgccaaga gggtggcgca      1860
cccccactcc atggggacag aagctccagc atttgcccag acccgtcca gacctcaccc       1920 tgtgtgtatc ttcatctggc tgtttactta tttgtatcct tttctaataa tgtttgtaat     1980
aaactggtaa acataaaaaa aaaaaaaaaa aaaaaaaaa                             2020
```

<210> SEQ ID NO 4
<211> LENGTH: 201
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 19, 20, 32, 33, 34, 60, 70, 78, 123, 135, 137, 151, 154,
      168, 176, 192
<223> OTHER INFORMATION: Xaa = Any or No Amino Acid

<400> SEQUENCE: 4

```
Gly Ile Pro Ser Ser Leu Arg Gly Arg Ala Trp Gln Tyr Leu Ser Gly
 1               5                  10                  15

Ser Lys Xaa Xaa Leu Glu Gln Asn Pro Gly Lys Phe Glu Glu Leu Xaa
            20                  25                  30

Xaa Xaa Pro Gly Asp Pro Lys Trp Leu Asp Val Ile Glu Lys Asp Leu
        35                  40                  45

His Arg Gln Phe Pro Phe His Glu Met Phe Val Xaa Arg Gly Gly His
 50                  55                  60

Gly Gln Gln Asp Leu Xaa Arg Val Leu Lys Ala Tyr Thr Xaa Tyr Arg
 65                  70                  75                  80

Pro Glu Glu Gly Tyr Cys Gln Ala Gln Ala Pro Ile Ala Ala Val Leu
                 85                  90                  95

Leu Met His Met Phe Ala Glu Gln Ala Phe Trp Cys Leu Val Gln Ile
            100                 105                 110

Cys Glu Lys Tyr Leu Pro Gly Tyr Tyr Ser Xaa Gly Leu Glu Ala Ile
            115                 120                 125

Gln Leu Asp Gly Glu Ile Xaa Phe Xaa Leu Leu Arg Lys Val Ser Pro
130                 135                 140

Val Ala His Lys His Leu Xaa Arg Gln Xaa Ile Asp Pro Val Leu Tyr
145                 150                 155                 160

Met Thr Glu Trp Phe Met Cys Xaa Phe Ser Arg Thr Leu Pro Trp Xaa
                165                 170                 175

Ser Val Leu Arg Val Trp Asp Met Phe Phe Cys Glu Gly Val Lys Xaa
            180                 185                 190

Ile Phe Arg Val Ala Leu Val Leu Leu
        195                 200
```

<210> SEQ ID NO 5
<211> LENGTH: 201
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 4, 8, 9, 13, 16, 17, 19, 20, 21, 22, 28, 29, 31, 32, 33,

```
           34, 35, 36, 38, 39, 40, 41, 42, 43, 46, 59, 60, 61, 64,
           70, 71, 72, 74, 77, 78, 80, 81, 82, 83, 92, 109, 111, 112,
           114, 115, 118, 121, 123, 124, 130, 133, 134, 135, 136, 137
<223> OTHER INFORMATION: Xaa = Any or No Amino Acid
<220> FEATURE:
<221> NAME/KEY: VARIANT
<222> LOCATION: 140, 141, 142, 144, 145, 147, 148, 151, 152, 153, 154,
           155, 156, 158, 168, 170, 174, 176, 177, 181, 190, 192, 196, 197,
           200
<223> OTHER INFORMATION: Xaa = Any or No Amino Acid

<400> SEQUENCE: 5

Gly Ile Pro Xaa Ser Leu Arg Xaa Xaa Ala Trp Gln Xaa Leu Ser Xaa
 1               5                  10                  15

Xaa Lys Xaa Xaa Xaa Xaa Gln Asn Pro Gly Lys Xaa Xaa Glu Xaa Xaa
                20                  25                  30

Xaa Xaa Xaa Xaa Asp Xaa Xaa Xaa Xaa Xaa Ile Glu Xaa Asp Leu
            35                  40                  45

His Arg Gln Phe Pro Phe His Glu Met Phe Xaa Xaa Xaa Gly Gly Xaa
 50                  55                  60

Gly Gln Gln Asp Leu Xaa Xaa Xaa Leu Xaa Ala Tyr Xaa Xaa Tyr Xaa
 65                  70                  75                  80

Xaa Xaa Xaa Gly Tyr Cys Gln Ala Gln Ala Pro Xaa Ala Ala Val Leu
                85                  90                  95

Leu Met His Met Phe Ala Glu Gln Ala Phe Trp Cys Xaa Val Xaa Xaa
                100                 105                 110

Cys Xaa Xaa Tyr Leu Xaa Gly Tyr Xaa Ser Xaa Xaa Leu Glu Ala Ile
            115                 120                 125

Gln Xaa Asp Gly Xaa Xaa Xaa Xaa Xaa Leu Leu Xaa Xaa Xaa Ser Xaa
        130                 135                 140

Xaa Ala Xaa Xaa His Leu Xaa Xaa Xaa Xaa Xaa Xaa Pro Xaa Leu Tyr
145                 150                 155                 160

Met Thr Glu Trp Phe Met Cys Xaa Phe Xaa Arg Thr Leu Xaa Trp Xaa
                165                 170                 175

Xaa Val Leu Arg Xaa Trp Asp Met Phe Phe Cys Glu Gly Xaa Lys Xaa
            180                 185                 190

Ile Phe Arg Xaa Xaa Leu Val Xaa Leu
            195                 200

<210> SEQ ID NO 6
<211> LENGTH: 167
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 6, 7, 8, 9, 10, 11, 12, 13, 14, 15, 16, 17, 18, 19, 20,
           21, 22, 23, 24, 37, 38, 39, 40, 41, 42, 48, 49, 50, 51, 52,
           53, 54, 55, 56, 57, 58, 59, 60, 61, 70, 87, 88, 89, 90,
           91, 92, 93, 94, 95, 96, 97, 98, 99, 100, 101, 102, 108,
           109
<223> OTHER INFORMATION: Xaa = Any or No Amino Acid
<220> FEATURE:
<221> NAME/KEY: VARIANT
<222> LOCATION: 110, 111, 112, 113, 114, 115, 116, 117, 118, 119, 120,
           121, 122, 123, 124, 125, 126, 127, 128, 129, 130, 131, 132, 133,
           134, 135, 136, 146, 147, 148, 149, 150, 151, 152, 153, 154,
           155, 156, 157, 158, 159
<223> OTHER INFORMATION: Xaa = Any or No Amino Acid

<400> SEQUENCE: 6

Gln Asn Pro Gly Lys Xaa Xaa Xaa Xaa Xaa Xaa Xaa Xaa Xaa Xaa
 1               5                  10                  15
```

-continued

Xaa Xaa Xaa Xaa Xaa Xaa Xaa Xaa Asp Leu His Arg Gln Phe Pro Phe
                20                  25                  30

His Glu Met Phe Xaa Xaa Xaa Xaa Xaa Gly Gln Gln Asp Leu Xaa
        35                  40                  45

Xaa Xaa Xaa Xaa Xaa Xaa Xaa Xaa Xaa Xaa Xaa Gly Tyr Cys
    50                  55                  60

Gln Ala Gln Ala Pro Xaa Ala Ala Val Leu Leu Met His Met Phe Ala
65                  70                  75                  80

Glu Gln Ala Phe Trp Cys Xaa Xaa Xaa Xaa Xaa Xaa Xaa Xaa
                85                  90                  95

Xaa Xaa Xaa Xaa Xaa Xaa Leu Glu Ala Ile Gln Xaa Xaa Xaa Xaa
        100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Leu Tyr Met Thr Glu Trp Phe Met
    130                 135                 140

Cys Xaa Xaa Xaa Xaa Xaa Xaa Xaa Xaa Xaa Xaa Xaa Xaa Trp
145                 150                 155                 160

Asp Met Phe Phe Cys Glu Gly
                165

<210> SEQ ID NO 7
<211> LENGTH: 399
<212> TYPE: PRT
<213> ORGANISM: Human

<400> SEQUENCE: 7

Met Ala Leu Arg Ser Ala Gln Gly Asp Gly Pro Thr Ser Gly His Trp
1               5                   10                  15

Asp Gly Gly Ala Glu Lys Ala Asp Phe Asn Ala Lys Arg Lys Lys Lys
                20                  25                  30

Val Ala Glu Ile His Gln Ala Leu Asn Ser Asp Pro Thr Asp Val Ala
        35                  40                  45

Ala Leu Arg Arg Met Ala Ile Ser Glu Gly Gly Leu Leu Thr Asp Glu
    50                  55                  60

Ile Arg Arg Lys Val Trp Pro Lys Leu Leu Asn Val Asn Ala Asn Asp
65                  70                  75                  80

Pro Pro Pro Ile Ser Gly Lys Asn Leu Arg Gln Met Ser Lys Asp Tyr
                85                  90                  95

Gln Gln Val Leu Leu Asp Val Arg Arg Ser Leu Arg Arg Phe Pro Pro
        100                 105                 110

Gly Met Pro Glu Glu Gln Arg Glu Gly Leu Gln Glu Glu Leu Ile Asp
    115                 120                 125

Ile Ile Leu Leu Ile Leu Glu Arg Asn Pro Gln Leu His Tyr Tyr Gln
    130                 135                 140

Gly Tyr His Asp Ile Trp Thr Phe Leu Leu Trp Gly Glu Arg Leu Ala
145                 150                 155                 160

Thr Ser Leu Val Glu Lys Leu Ser Thr His His Leu Arg Asp Phe Met
                165                 170                 175

Asp Pro Thr Met Asp Asn Thr Lys His Ile Leu Asn Tyr Leu Met Pro
        180                 185                 190

Ile Ile Asp Gln Val Asn Pro Glu Leu His Asp Phe Met Gln Ser Ala
    195                 200                 205

Glu Val Gly Thr Ile Phe Ala Leu Ser Trp Leu Ile Thr Trp Phe Gly

-continued

```
                210                 215                 220
His Val Leu Ser Asp Phe Arg His Trp Arg Leu Tyr Asp Phe Phe Leu
225                 230                 235                 240

Ala Cys His Pro Leu Met Pro Ile Tyr Phe Ala Ala Val Ile Val Leu
                245                 250                 255

Tyr Arg Glu Gln Glu Val Leu Asp Cys Asp Cys Asp Met Ala Ser Val
                260                 265                 270

His His Leu Leu Ser Gln Ile Pro Gln Asp Leu Pro Tyr Glu Thr Leu
                275                 280                 285

Ile Ser Arg Ala Gly Asp Leu Phe Val Gln Phe Pro Pro Ser Glu Leu
290                 295                 300

Ala Arg Glu Ala Ala Gln Gln Gln Ala Glu Arg Thr Ala Ala Ser
305                 310                 315                 320

Thr Phe Lys Asp Phe Glu Leu Ala Ser Ala Gln Gln Arg Pro Asp Met
                325                 330                 335

Val Leu Arg Gln Arg Phe Arg Gly Leu Leu Arg Pro Glu Asp Arg Thr
                340                 345                 350

Lys Asp Val Leu Thr Lys Pro Arg Thr Asn Arg Phe Val Lys Leu Ala
                355                 360                 365

Val Met Gly Leu Thr Val Ala Leu Gly Ala Ala Leu Ala Trp Lys
                370                 375                 380

Ser Ala Leu Glu Trp Ala Pro Lys Phe Gln Leu Gln Leu Phe Pro
385                 390                 395
```

<210> SEQ ID NO 8
<211> LENGTH: 25
<212> TYPE: PRT
<213> ORGANISM: Artificial Sequence
<220> FEATURE:
<223> OTHER INFORMATION: TBC Polypeptide Domain
<220> FEATURE:
<221> NAME/KEY: VARIANT
<222> LOCATION: 9
<223> OTHER INFORMATION: Xaa = Any Amino Acid

<400> SEQUENCE: 8

```
Gly Tyr Cys Gln Ala Gln Ala Pro Xaa Ala Ala Val Leu Leu Met His
1               5                   10                  15

Met Phe Ala Glu Gln Ala Phe Trp Cys
                20                  25
```

<210> SEQ ID NO 9
<211> LENGTH: 9
<212> TYPE: PRT
<213> ORGANISM: Artificial Sequence
<220> FEATURE:
<223> OTHER INFORMATION: TBC Polypeptide Domain

<400> SEQUENCE: 9

```
Leu Tyr Met Thr Glu Trp Phe Met Cys
1               5
```

<210> SEQ ID NO 10
<211> LENGTH: 14
<212> TYPE: PRT
<213> ORGANISM: Artificial Sequence
<220> FEATURE:
<223> OTHER INFORMATION: TBC Polypeptide Domain
<220> FEATURE:
<221> NAME/KEY: VARIANT
<222> LOCATION: 7, 8
<223> OTHER INFORMATION: Xaa = Any Amino Acid -continued

<400> SEQUENCE: 10

Pro Leu Pro Pro Pro Arg Xaa Xaa Pro Val Pro Pro Arg
1               5                   10

<210> SEQ ID NO 11
<211> LENGTH: 8
<212> TYPE: PRT
<213> ORGANISM: Artificial Sequence
<220> FEATURE:
<223> OTHER INFORMATION: TBC Polypeptide Domain

<400> SEQUENCE: 11

Trp Asp Met Phe Phe Cys Glu Gly
1               5

<210> SEQ ID NO 12
<211> LENGTH: 12
<212> TYPE: PRT
<213> ORGANISM: Artificial Sequence
<220> FEATURE:
<223> OTHER INFORMATION: TBC Polypeptide Domain

<400> SEQUENCE: 12

Asp Leu His Arg Gln Phe Pro Phe His Glu Met Phe
1               5                   10

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
ccagcagagg ccugauaugu u                                         21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
cauaucaggc cucugcuggu u                                         21

<210> SEQ ID NO 15
<211> LENGTH: 23
<212> TYPE: RNA
<213> ORGANISM: Artificial Sequence
<220> FEATURE:
<223> OTHER INFORMATION: siRNA

<400> SEQUENCE: 15
ugcaggagag auugaccgcu auu                                       23

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
ccagcgagaa cgucaauaau u                                         21

```
<210> SEQ ID NO 17
<211> LENGTH: 21
<212> TYPE: RNA
<213> ORGANISM: Artificial Sequence
<220> FEATURE:
<223> OTHER INFORMATION: siRNA

<400> SEQUENCE: 17 cgguggggauc ugaguauauu u                                              21

<210> SEQ ID NO 18
<211> LENGTH: 21
<212> TYPE: RNA
<213> ORGANISM: Artificial Sequence
<220> FEATURE:
<223> OTHER INFORMATION: siRNA

<400> SEQUENCE: 18
gaauaugacu accuguuuau u                                               21

<210> SEQ ID NO 19
<211> LENGTH: 16
<212> TYPE: DNA
<213> ORGANISM: Artificial Sequence
<220> FEATURE:
<223> OTHER INFORMATION: primer

<400> SEQUENCE: 19
agagccatag tggtct                                                     16

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
ccaaatctcc aggcattgag c                                               21

<210> SEQ ID NO 21
<211> LENGTH: 24
<212> TYPE: DNA
<213> ORGANISM: Artificial Sequence
<220> FEATURE:
<223> OTHER INFORMATION: probe

<400> SEQUENCE: 21
caccggaatt gccaggacga ccgg                                            24
```